United States Patent [19]

Castro Pineiro et al.

[11] Patent Number: 5,807,857
[45] Date of Patent: Sep. 15, 1998

[54] PIPERAZINE, PIPERIDINE AND TETRAHYDROPYRIDINE DERIVATIVE OF INDOL-3-ALKYL AS 5-HT$_{1D-\alpha}$AGONISTS

[75] Inventors: Jose Luis Castro Pineiro, Harlow; Mark Stuart Chambers, Ware; Sarah Christine Hobbs; Austin John Reeve, both of Great Dunmow; Graham Andrew Showell, Welwyn Garden City; Leslie Joseph Street, Harlow, all of Great Britain; Victor Giulio Matassa, Rome, Italy

[73] Assignee: Merck Sharp & Dohme Ltd., Hoddesdon, England

[21] Appl. No.: 737,769

[22] PCT Filed: May 18, 1995

[86] PCT No.: PCT/GB95/01129

§ 371 Date: Nov. 15, 1996

§ 102(e) Date: Nov. 15, 1996

[87] PCT Pub. No.: WO95/32196

PCT Pub. Date: Nov. 30, 1995

[30] Foreign Application Priority Data

| May 19, 1994 | [GB] | United Kingdom | 9410080 |
| Jun. 15, 1994 | [GB] | United Kingdom | 9411954 |
| Aug. 4, 1994 | [GB] | United Kingdom | 9415805 |
| Dec. 16, 1994 | [GB] | United Kingdom | 9425448 |

[51] Int. Cl.$^6$ .................. A61K 31/495; A61K 31/445; C07D 401/14; C07D 403/14

[52] U.S. Cl. .................. 514/253; 514/323; 514/339; 544/362; 544/364; 544/366; 544/368; 544/370; 546/201; 546/272.4

[58] Field of Search .................. 544/362, 364, 544/366, 370, 368; 514/253

[56] References Cited

U.S. PATENT DOCUMENTS

| 5,403,847 | 4/1995 | Ginchowski et al. |
| 5,432,177 | 7/1995 | Baker et al. .................. 514/253 |
| 5,494,910 | 2/1996 | North et al. .................. 514/233.5 |
| 5,552,402 | 9/1996 | Matassa et al. .................. 514/233.5 |
| 5,614,524 | 3/1997 | Matassa et al. .................. 514/253 |
| 5,618,816 | 4/1997 | Crenshaw et al. .................. 544/367 |

FOREIGN PATENT DOCUMENTS

| 0 438 230 | 7/1991 | European Pat. Off. |
| 0 497 512 | 8/1992 | European Pat. Off. |
| 0 548 813 | 6/1993 | European Pat. Off. |
| 91/18897 | 12/1991 | WIPO |
| 92/13856 | 8/1992 | WIPO |
| 94 02477 | 3/1993 | WIPO |
| 93/18029 | 9/1993 | WIPO |
| 9320073 | 10/1993 | WIPO |
| 94/02477 | 2/1994 | WIPO |

OTHER PUBLICATIONS

Aggarwal et al. *J. Med. Chem.* 33, p. 1505–1510, (1990).
Chambers et al, *Chemical Abstracts*, vol. 125, No. 33675, (1996).

*Primary Examiner*—Emily Bernhardt
*Attorney, Agent, or Firm*—Philippe L. Durette; Melvin Winokur

[57] ABSTRACT

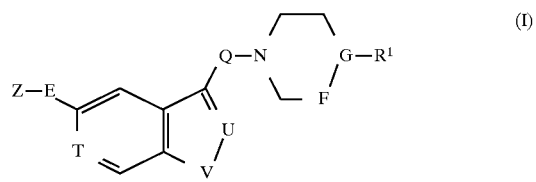

Compounds of formula (I), or a salt or prodrug thereof, wherein Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; E represents a chemical bond or a straight or branched alkylene chain containing from 1 to 4 carbon atoms; Q represents a straight or branched alkylene chain containing from 1 to 6 carbon atoms, optionally substituted in any position by a hydroxy group; T represents nitrogen or CH; U represents nitrogen or C—R$^2$; V represents oxygen, sulphur or N—R$^3$; —F—G— represents —CH2—N—, —CH2—CH— or —CH=C—; R$^1$ represents C$_{3-6}$alkenyl, C$_{3-6}$alkynyl, aryl(C$_{1-6}$)alkyl or heteroaryl(C$_{1-6}$)alkyl, any of which groups may be optionally substituted; and R$^2$ and R$^3$ independently represent hydrogen or C$_{1-6}$alkyl are selective agonists of 5-HT1D receptors, being potent agonists of the human 5-HT1Dalpha receptor subtype, while possessing at least a 10-fold selective affinity for the 5-HT1Dalpha receptor subtype, relative to the 5-HT1Dbeta subtype; they are therefore useful in the treatment and/or prevention of clinical conditions, in particular migraine and associated disorders, for which a subtype-selective agonist of 5-HT1D receptors is indicated, while eliciting fewer side-effects, notably adverse cardiovascular events, than those associated with non-subtype-selective 5-HT1D receptor agonists.

9 Claims, No Drawings

PIPERAZINE, PIPERIDINE AND TETRAHYDROPYRIDINE DERIVATIVE OF INDOL-3-ALKYL AS 5-HT$_{1D\text{-}\alpha}$AGONISTS The present invention relates to a class of substituted piperazine, piperidine and tetrahydropyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309-11).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D\text{-}1}$) and 5-HT$_{1D\beta}$ (or 5-HT$_{1D\text{-}2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861-2; and D. N. Bateman, *The Lancet*, 1993, 341, 221-4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666-9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT1D receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT1D receptor agonists.

Several distinct classes of substituted five-membered heteroaromatic compounds are described in published European patent applications 0438230, 0497512 and 0494774, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the piperazine, piperidine and tetrahydropyridine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with an optionally substituted alkenyl, alkynyl, aryl-alkyl or heteroaryl-alkyl substituent; nor is there any suggestion therein that the range of substituents specified at the 5-position of the indole moiety might be successfully replaced by an optionally substituted five-membered heteroaromatic ring.

Moreover, nowhere in the prior art available to date is there any disclosure of a subtype-selective 5-HT1D receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

In one aspect, therefore, the present invention provides a subtype-selective 5-HT1D receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype. In a preferred embodiment of this aspect, the present invention provides a subtype-selective 5-HT$_{1D}$ receptor agonist having a 5-HT$_{1D\alpha}$ receptor binding affinity (IC$_{50}$) below 10 nM and at least a 50-fold selective affinity for the 5-HT$_{1D\alpha}$ subtype relative to the 5-HT$_{1D\beta}$ subtype.

In another aspect, the present invention provides a compound of formula I, or a salt or prodrug thereof:

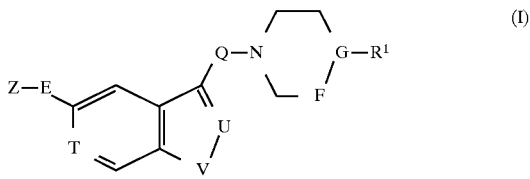

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms, optionally substituted in any position by a hydroxy group;

T represents nitrogen or CH;

U represents nitrogen or C—R$^2$;

V represents oxygen, sulphur or N—R$^3$;

—F—G— represents —CH$_2$—N—, —CH$_2$—CH— or —CH=C—;

R$^1$ represents C$_{3\text{-}6}$ alkenyl, C$_{3\text{-}6}$ alkynyl, aryl(C$_{1\text{-}6}$)alkyl or heteroaryl(C$_{1\text{-}6}$)alkyl, any of which groups may be optionally substituted; and R$^2$ and R$^3$ independently represent hydrogen or C$_{1\text{-}6}$ alkyl.

The present invention also provides compounds of formula I above wherein T represents CH; R$^1$ represents aryl($C_{1-6}$)alkyl or heteroaryl($C_{1-6}$)alkyl, either of which groups may be optionally substituted; and Z, E, Q, U, V, F and G are as defined above.

The present invention further provides compounds of formula I above wherein Q represents a straight or branched alkylene chain containing from 1 to 6 carbon atoms; T represents CH; $R^1$ represents aryl($C_{1-6}$)alkyl or heteroaryl ($C_{1-6}$)alkyl, either of which groups may be optionally substituted; and Z, E, U, V, F and G are as defined above.

The present invention still further provides compounds of formula I above wherein Q represents a straight or branched alkylene chain containing from 1 to 6 carbon atoms; T represents CH; —F—G— represents —$CH_2$—N—; $R^1$ represents aryl($C_{1-6}$)alkyl or heteroaryl($C_{1-6}$)alkyl, either of which groups may be optionally substituted; and Z, E, U and V are as defined above.

The present invention yet further provides compounds of formula I above wherein Q represents a straight or branched alkylene chain containing from 1 to 6 carbon atoms; T represents nitrogen; U represents C—$R^2$; V represents N—$R^3$; —F—G— represents —$CH_2$—N—; $R^1$ represents aryl($C_{1-6}$)alkyl or heteroaryl($C_{1-6}$)alkyl, either of which groups may be optionally substituted; and Z, E, $R^2$ and $R^3$ are as defined above.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano and trifluoromethyl.

The group $R^1$ may be optionally substituted by one or more substituents. Where $R^1$ represents aryl($C_{1-6}$)alkyl or heteroaryl($C_{1-6}$)alkyl, any optional substitution will suitably be on the aryl or heteroaryl moiety thereof, although substitution on the alkyl moiety thereof is an alternative possibility. Examples of optional substituents on the group $R^1$ include halogen, cyano, trifluoromethyl, triazolyl, tetrazolyl, $C_{1-6}$ alkyl-tetrazolyl, hydroxy, $C_{1-6}$alkoxy, $C_{1-6}$alkylthio, $C_{2-6}$ alkoxycarbonyl, $C_{2-6}$ alkylcarbonyl, $C_{1-6}$-alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$)alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by a hydroxy group giving rise, for example, to a 2-hydroxypropylene or 2-hydroxymethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene and 2-hydroxymethyl-propylene.

The compound of formula I in accordance with the present invention is suitably an indole, benzofuran or benzthiophene derivative of formula IA, an indazole derivative of formula IB, or a pyrrolo[2,3-c]-pyridine derivative of formula IC:

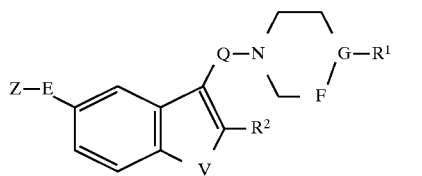
(IA)

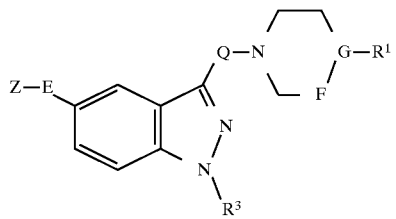
(IB)

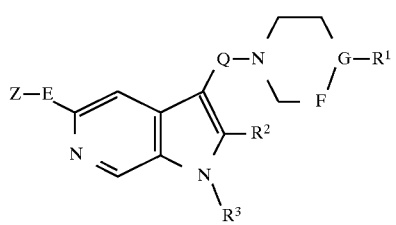
(IC)

wherein Z, E, Q, V, F, G, $R^1$, $R^2$ and $R^3$ are as defined above. Preferably, the compounds according to the invention are indole or pyrrolo[2,3-c]-pyridine derivatives of formula ID:

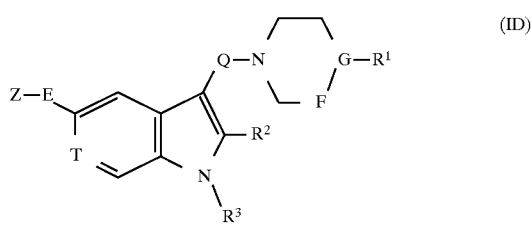
(ID)

wherein Z, E, Q, T, F, G, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, furylmethyl, thienylmethyl, imidazolylmethyl and pyridylmethyl, any of which groups may be optionally substituted by one or more substituents selected typically from halogen, cyano, triazolyl, tetrazolyl, $C_{1-6}$alkyl-tetrazolyl, $C_{1-6}$ alkoxy, amino, di($C_{1-6}$)alkylamino, di($C_{1-6}$) alkylaminomethyl, $C_{2-6}$ alkylcarbonylamino, $C_{2-6}$ alkoxycarbonylamino, N-($C_{1-6}$)alkyl-N-($C_{2-6}$) alkoxycarbonylamino, $C_{1-6}$ alkylsulphonylamino, aminocarbonylamino, aminocarbonyl, $C_{1-6}$alkylaminocarbonyl, di($C_{1-6}$)alkylaminocarbonyl, aminosulphonyl and $C_{1-6}$ alkylaminosulphonylmethyl.

Particular values of $R^1$ include allyl, dimethylallyl, butenyl, propargyl, benzyl, fluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, phenylethyl, cyano-phenylethyl, triazolyl-phenylethyl, amino-phenylethyl, dimethylamino-phenylethyl, acetylamino-phenylethyl, methoxycarbonylamino-phenylethyl, (N-methyl-N-methoxycarbonyl)amino-phenylethyl, aminocarbonylamino-phenylethyl, furylmethyl, thienylmethyl, imidazolylmethyl, pyridylmethyl and amino-pyridylmethyl.

Suitably, $R^2$ and $R^3$ independently represent hydrogen or methyl, especially hydrogen.

A particular sub-class of compounds according to the invention is represented by the compounds of formula IIA, and salts and prodrugs thereof:

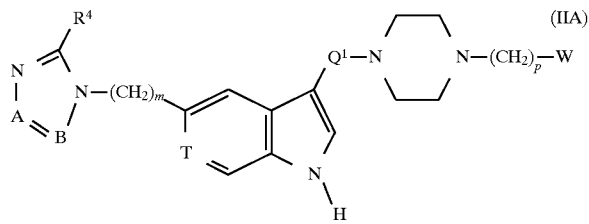
(IIA)

wherein
m is zero, 1, 2 or 3;
p is 1, 2 or 3;
$Q^1$ represents a straight or branched alkylene chain containing from 2 to 5 carbon atoms, optionally substituted in any position by a hydroxy group;
T represents nitrogen or CH;
A represents nitrogen or CH;
B represents nitrogen or C—$R^5$;
$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and W represents a group of formula (a), (b) or (c):

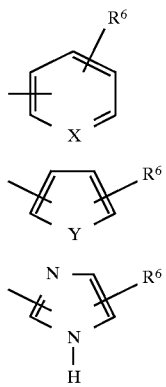

in which

X represents CH or nitrogen;

Y represents oxygen, sulphur or NH; and $R^6$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$) alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

Suitably, $Q^1$ represents a straight or branched 3 or 4 carbon alkylene chain, optionally substituted in any position by a hydroxy group. Particular alkylene chains for $Q^1$ include propylene, butylene, 2-hydroxypropylene and 2-(hydroxymethyl)-propylene.

Particular values of $R^4$ and $R^5$ include hydrogen, methyl, ethyl, benzyl and amino, especially hydrogen.

Particular values of $R^6$ include hydrogen, fluoro, cyano, triazolyl, tetrazolyl, methyl-tetrazolyl, methoxy, amino, dimethylaminomethyl, acetylamino, aminocarbonylamino, methylaminocarbonyl and aminosulphonyl.

Another sub-class of compounds according to the invention is represented by the compounds of formula IIB, and salts and prodrugs thereof:

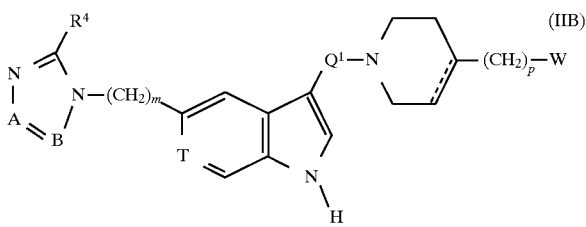

wherein the broken line represents an optional chemical bond; and m, p, $Q^1$, T, A, B, $R^4$ and W are as defined with reference to formula IIA above.

In the compounds of formula IIA and IIB as defined above, $Q^1$ may represent a group of formula —$(CH_2)_n$— wherein n is 2, 3, 4 or 5, preferably 3 or 4.

The present invention also provides compounds of formula IIA and IIB as defined above wherein T represents CH; and $R^6$ is other than $C_{1-6}$ alkyl-tetrazolyl, di($C_{1-6}$) alkylaminomethyl and $C_{1-6}$ alkylaminocarbonyl.

The present invention further provides compounds of formula IIA and IIB as defined above wherein $Q^1$ represents —$(CH_2)_n$—; T represents CH; and $R^6$ is other than tetrazolyl, $C_{1-6}$ alkyl-tetrazolyl, di($C_{1-6}$)alkylaminomethyl, $C_{1-6}$ alkylaminocarbonyl and aminosulphonyl.

The present invention additionally provides compounds of formula IIA as defined above wherein $Q^1$ represents —$(CH_2)_n$—; T represents CH; and $R^6$ is other than triazolyl, tetrazolyl, $C_{1-6}$ alkyl-tetrazolyl, di($C_{1-6}$)alkylaminomethyl, aminocarbonylamino, $C_{1-6}$ alkylaminocarbonyl and aminosulphonyl.

The present invention provides in addition compounds of formula IIA as defined above wherein $Q^1$ represents —$(CH_2)_n$—; T represents nitrogen; and $R^6$ is other than triazolyl, tetrazolyl, $C_{1-6}$ alkyl-tetrazolyl, di($C_{1-6}$) alkylaminomethyl, aminocarbonylamino, $C_{1-6}$ alkylaminocarbonyl and aminosulphonyl.

A further sub-class of compounds according to the invention is represented by the compounds of formula IIC, and salts and prodrugs thereof:

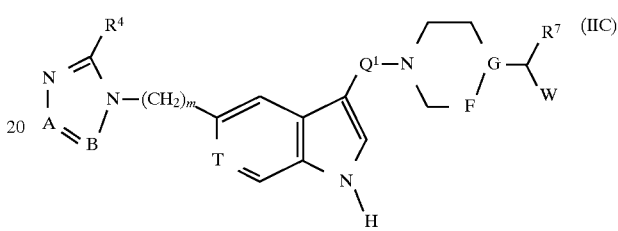

wherein

T, F and G are as defined with reference to formula I above;

m, $Q^1$, $R^4$, A, B and W are as defined with reference to formula IIA above; and $R^7$ represents hydrogen, aminomethyl, $C_{1-6}$ alkylaminomethyl, di($C_{1-6}$)alkylaminomethyl, $C_{2-6}$ alkoxycarbonylaminomethyl, [N-($C_{1-6}$)alkyl-N-($C_{2-6}$) alkoxycarbonyl]aminomethyl, aminocarbonyl, $C_{1-6}$ alkylaminocarbonyl or di($C_{1-6}$)alkylaminocarbonyl.

Particular values of $R^7$ include hydrogen, dimethylaminomethyl, methoxycarbonylaminomethyl, (N-methyl-N-methoxycarbonyl)aminomethyl, aminocarbonyl, methylaminocarbonyl and dimethylaminocarbonyl, especially hydrogen.

Specific compounds within the scope of the present invention include:

1-[3-(5-(1,2,4-triazol-4-yl)-1H-indol-3-yl)propyl]-4-[4-(acetylamino)phenyl]methylpiperazine;

1-[4-(5-(1,2,4-triazol-4-yl)-1H-indol-3-yl)butyl]-4-[4-(acetylamino)phenyl]methylpiperazine;

1-[3-(5-(1,2,4-triazol-4-yl)-1H-indol-3-yl)propyl]-4-(2-methoxyphenyl)methylpiperazine;

1-[3-(5-(1,2,4-triazol-4-yl)-1H-indol-3-yl)propyl]-4-benzylpiperazine;

1-[3-(5-(1,2,4-triazol-4-yl)-1H-indol-3-yl)propyl]-4-(pyridin-3-yl)methylpiperazine;

1-[3-(5-(1,2,4-triazol-4-yl)-1H-indol-3-yl)propyl]-4-(pyridin-2-yl)methylpiperazine;

1-[3-(5-(1,2,4-triazol-4-yl)-1H-indol-3-yl)propyl]-4-(pyridin-4-yl)methylpiperazine;

1-[3-(5-(1,2,4-triazol-4-yl)-1H-indol-3-yl)propyl]-4-(4-aminophenyl)methylpiperazine;

1-[4-(5-(1,2,4-triazol-4-yl)-1H-indol-3-yl)butyl]-4-benzylpiperazine;

1-[4-(5-(1,2,4-triazol-4-yl)-1H-indol-3-yl)butyl]-4-(pyridin-2-yl)methylpiperazine;

1-[4-(5-(1,2,4-triazol-4-yl)-1H-indol-3-yl)butyl]-4-(pyridin-3-yl)methylpiperazine;

1-[3-(5-(1,2,4-triazol-4-yl)-1H-indol-3-yl)propyl]-4-[2-(4-aminophenyl)ethyl]piperazine;

1-[3-(5-(1,2,4-triazol-4-yl)-1H-indol-3-yl)propyl]-4-[2-(4-(acetylamino)phenyl)ethyl]piperazine;

1-[3-(5-(1,2,4-triazol-4-yl)-1H-indol-3-yl)propyl]-4-(imidazol-2-yl)methylpiperazine;
1-[3-(5-(1,2,4-triazol-4-yl)-1H-indol-3-yl)propyl]-4-[3-(acetylamino)phenyl]methylpiperazine;
4-benzyl-1-[3-(5-(1,2,4-triazol-1-yl)-1H-pyrrolo[2,3-c]pyridin-3-yl)propyl]piperazine;
4-benzyl-1-[3-(5-(1,2,4-triazol-4-yl)-1H-pyrrolo[2,3-c]pyridin-3-yl)propyl]piperazine;
4-(4-acetylaminophenyl)methyl-1-[3-(5-(1,2,4-triazol-4-yl)-1H-indol-3-yl)propyl]piperidine;
4-benzyl-1-[3-(5-(1,2,4-triazol-4-yl)-1H-indol-3-yl)propyl]-1,2,5,6-tetrahydropyridine;
1-[3-(5-(1,2,4-triazol-4-yl)-1H-indol-3-yl)propyl]-4-(2-aminopyridin-5-yl)methylpiperazine;
1-[3-(5-(1,2,4-triazol-4-yl)-1H-indol-3-yl)propyl]-4-[2-(4-(aminocarbonylamino)phenyl)ethyl]piperazine;
1-[3-(5-(1,2,4-triazol-4-yl)-1H-indol-3-yl)propyl]-4-(4-cyanophenyl)methylpiperazine;
1-[3-(5-(1,2,4-triazol-4-yl)-1H-indol-3-yl)propyl)-4-[2-(4-cyanophenyl)ethyl]piperazine;
1-[3-(5-(1,2,4-triazol-4-yl)-1H-indol-3-yl)propyl]-4-[2-(4-(1,2,4-triazol-4-yl)phenyl)ethyl]piperazine;
1-[3-(5-(1,2,4-triazol-1-yl)-1H-indol-3-yl)propyl]-4-[2-(4-(acetylamino)phenyl)ethyl]piperazine;
1-[3-(5-(1,2,4-triazol-1-yl)-1H-indol-3-yl)propyl]-4-benzylpiperazine;
1-[3-(5-(1,2,4-triazol-1-ylmethyl)-1H-indol-3-yl)propyl]-4-benzylpiperazine;
1-[3-(5-(1,2,4-triazol-1-ylmethyl)-1H-indol-3-yl)propyl]-4-[2-(4-(acetylamino)phenyl)ethyl]piperazine;
1-[3-(5-(1,2,4-triazol-4-yl)-1H-indol-3-yl)propyl]-4-[2-(3-(acetylamino)phenyl)ethyl]piperazine;
1-[3-(5-(1,2,4-triazol-4-yl)-1H-indol-3-yl)propyl]-4-[4-(aminosulphonyl)phenyl]methylpiperazine;
1-[3-(5-(1,2,4-triazol-4-yl)-1H-indol-3-yl)propyl]-4-(furan-3-yl)methylpiperazine;
1-[3-(5-(1,2,4-triazol-4-yl)-1H-indol-3-yl)propyl]-4-(furan-2-yl)methylpiperazine;
1-[3-(5-(1,2,4-triazol-4-yl)-1H-indol-3-yl)propyl]-4-(thien-2-yl)methylpiperazine;
1-benzyl-4-[(R,S)-2-hydroxy-3-(5-(1,2,4-triazol-4-yl)-1H-indol-3-yl)propyl]piperazine;
1-[2-(4-(acetylamino)phenyl)ethyl]-4-[(R,S)-2-hydroxy-3-(5-(1,2,4-triazol-4-yl)-1H-indol-3-yl)propyl]piperazine;
1-benzyl-4-[(R,S)-2-hydroxymethyl-3-(5-(1,2,4-triazol-4-yl)-1H-indol-3-yl)propyl]piperazine;
1-[3-(5-(1,2,4-triazol-4-yl)-1H-indol-3-yl)propyl]-4-[2-(1H-tetrazol-5-yl)phenyl]methylpiperazine;
1-[3-(5-(1,2,4-triazol-4-yl)-1H-indol-3-yl)propyl]-4-(2-phenylethyl)piperazine;
4-benzyl-1-[3-(5-(1,2,4-triazol-4-yl)-1H-indol-3-yl)propyl] piperazine;
4-[2-(2-methyltetrazol-5-yl)phenyl]methyl-1-[3-(5-(1,2,4-triazol-4-yl)-1H-indol-3-yl)propyl]piperazine;
4-[2-(1-methyltetrazol-5-yl)phenyl]methyl-1-[3-(5-(1,2,4-triazol-4-yl)-1H-indol-3-yl)propyl]piperazine;
4-[2-(N-methylcarboxamido)phenyl]methyl-1-[3-(5-(1,2,4-triazol-4-yl)-1H-indol-3-yl)propyl]piperazine;
4-[2-(N,N-dimethylaminomethyl)phenyl]methyl-1-[3-(5-(1,2,4-triazol-4-yl)-1H-indol-3-yl)propyl]piperazine;
4-(but-3-enyl)-1-[3-(5-(1,2,4-triazol-4-yl)-1H-indol-3-yl)propyl]piperazine;
4-(3-methylbut-2-enyl)-1-[3-(5-(1,2,4-triazol-4-yl)-1H-indol-3-yl)propyl]piperazine;
4-(prop-2-enyl)-1-[3-(5-(1,2,4-triazol-4-yl)-1H-indol-3-yl)propyl]piperazine;
4-(prop-2-ynyl)-1-[3-(5-(1,2,4-triazol-4-yl)-1H-indol-3-yl)propyl]piperazine;
4-[(R,S)-1-(phenyl)carboxamidomethyl]-1-[3-(5-(1,2,4-triazol-4-yl)-1H-indol-3-yl)propyl]piperazine;
(+)-4-[1-(phenyl)carboxamidomethyl]-1-[3-(5-(1,2,4-triazol-4-yl)-1H-indol-3-yl)propyl]piperazine;
(−)-4-[1-(phenyl)carboxamidomethyl]-1-[3-(5-(1,2,4-triazol-4-yl)-1H-indol-3-yl)propyl]piperazine;
4-[1-(phenyl)-N-methylcarboxamidomethyl]-1-[3-(5-(1,2,4-triazol-4-yl)-1H-indol-3-yl)propyl]piperazine;
4-[1-(phenyl)-N,N-dimethylcarboxamidomethyl]-1-[3-(5-(1,2,4-triazol-4-yl)-1H-indol-3-yl)propyl]piperazine;
4-(2-methoxycarbonylamino-1-phenylethyl)-1-[3-(5-(1,2,4-triazol-4-yl)-1H-indol-3-yl)propyl]piperazine;
4-(2-dimethylamino-1-phenylethyl)-1-[3-(5-(1,2,4-triazol-4-yl)-1H-indol-3-yl)propyl]piperazine;
4-[2-(4-(acetylamino)phenyl)ethyl]-1-[3-(5-(1,2,4-triazol-1-yl)-1H-pyrrolo[2,3-c]pyridin-3-yl)propyl]piperazine;
4-[2-(4-(acetylamino)phenyl)ethyl]-1-[3-(5-(1,2,4-triazol-4-yl)-1H-pyrrolo[2,3-c]pyridin-3-yl)propyl]piperazine;
1-[3-(5-(1,2,4-triazol-4-yl)-1H-indol-3-yl)propyl]-4-(4-fluorophenyl)methylpiperazine;
4-[2-(N-methyl-N-methoxycarbonyl)amino-1-phenylethyl]-1-[3-(5-(1,2,4-triazol-4-yl)-1H-indol-3-yl)propyl] piperazine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein —F—G— represents —CH$_2$—N— may be prepared by a process which comprises attachment of the R$^1$ moiety to a compound of formula III:

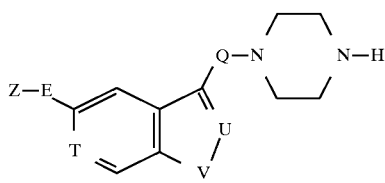

wherein Z, E, Q, T, U and V are as defined above; by conventional means including N-alkylation.

Attachment of the R$^1$ moiety to the compounds of formula III may conveniently be effected by standard alkylation techniques. One example thereof comprises treatment with an alkenyl halide such as 4-bromobut-1-ene, 4-bromo-2-methylbut-2-ene or allyl bromide, an alkynyl halide such as propargyl bromide, or an aryl(C$_{1-6}$)alkyl or heteroaryl(C$_{1-6}$)alkyl halide such as benzyl iodide, typically under basic conditions, e.g. sodium hydride or potassium carbonate in N,N-dimethylformamide, or triethylamine in acetonitrile. Another example comprises treatment of the compound of formula III with an aryl(C$_{1-6}$)alkyl or heteroaryl(C$_{1-6}$)alkyl mesylate such as 2-(4-cyanophenyl)ethyl methanesulphonate, typically in the presence of sodium carbonate and sodium iodide, in a suitable solvent such as 1,2-dimethoxyethane.

Alternatively, the R$^1$ moiety may conveniently be attached by reductive alkylation, which may be accomplished in a single step, or as a two-step procedure. The single-step approach suitably comprises treating the required compound of formula III as defined above with the appropriate aldehyde, e.g. benzaldehyde, furfuraldehyde or thiophene carboxaldehyde, in the presence of a reducing agent such as sodium cyanoborohydride. In a typical two-step procedure, for the preparation of a compound of formula I wherein R$^1$ corresponds to a group of formula —CH$_2$R$^{11}$, a carboxylic acid derivative of formula R$^{11}$—CO$_2$H is condensed with the required compound of formula III, suitably in the presence of 1-(3-dimethylaminopropyl)-3-ethylcarbodiimide hydrochloride and 1-hydroxybenzotriazole hydrate, to afford a compound corresponding to formula I wherein R$^1$ represents —COR$^{11}$; the carbonyl group thereof can then be reduced, for example by treatment with diisobutylaluminium hydride, and the required compound of formula I thereby obtained.

The compounds of formula III above wherein T represents CH, U represents C—R$^2$ and V represents N—R$^3$, corresponding to the indole derivatives of formula ID as defined above wherein T represents CH, —F—G— represents —CH$_2$—N— and R$^1$ is hydrogen, may be prepared by a process which comprises reacting a compound of formula IV:

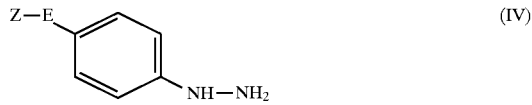

wherein Z and E are as defined above; with a compound of formula V, or a carbonyl-protected form thereof:

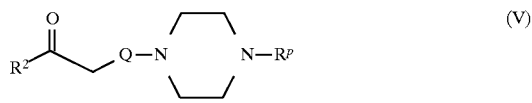

wherein R$^2$ and Q are as defined above, and R$^P$ represents an amino-protecting group; followed, where required, by N-alkylation by standard methods to introduce the moiety R$^3$; with subsequent removal of the amino-protecting group R$^P$.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group R$^P$ in the compounds of formula V is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

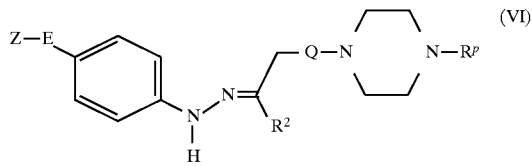

wherein Z, E, Q, R$^2$ and R$^P$ are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

wherein Q, R$^2$ and R$^P$ are as defined above, and L$^1$ represents a suitable leaving group.

The leaving group L$^1$ is suitably a halogen atom, e.g. chlorine or bromine.

Where L$^1$ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein T represents CH, U represents C—R² and V represents N—R³—i.e. the indole derivatives of formula ID as defined above—may alternatively be prepared by a process which comprises reacting a compound of formula IV as defined above with a compound of formula IX, or a carbonyl-protected form thereof:

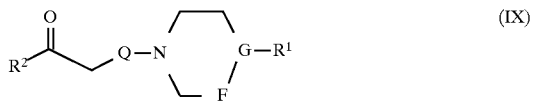

wherein Q, F, G, R¹ and R² are as defined above; under conditions analogous to those described above for the reaction between compounds IV and V; followed, where required, by N-alkylation by standard methods to introduce the moiety R³.

As for the compounds of formula V, suitable carbonyl-protected forms of the compounds of formula IX include the dimethyl acetal or ketal derivatives. Where the alkylene chain Q is substituted by a hydroxy group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

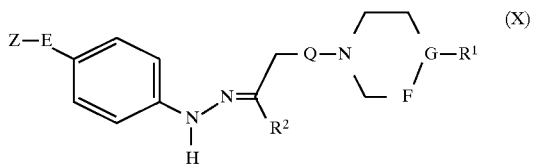

wherein Z, E, Q, F, G, R¹ and R² are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

wherein F, G and R¹ are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

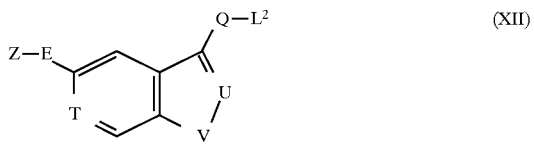

wherein Z, E, Q, T, U and V are as defined above, and L² represents a suitable leaving group; followed by removal of the amino-protecting group R^P.

Similarly, the compounds of formula I as defined above may be prepared by a process which comprises reacting a compound of formula XI as defined above with a compound of formula XII as defined above.

The leaving group L² is suitably an alkylsulphonyloxy or arylsulphonyloxy group, e.g. methanesulphonyloxy (mesyloxy) or p-toluenesulphonyloxy (tosyloxy).

Where L² represents an alkylsulphonyloxy or arylsulphonyloxy group, the reaction between compound XII and compound VIII or XI is conveniently carried out in a suitable solvent such as 1,2-dimethoxyethane or isopropyl alcohol, typically in the presence of a base such as sodium carbonate or potassium carbonate, optionally with the addition of a catalytic amount of sodium iodide.

In a representative embodiment, the compounds of formula XII wherein T and U both represent CH, V represents NH, Q represents a propylene chain and L² represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative IV or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds of formula III above wherein T represents CH, U represents nitrogen and V represents N—R³, corresponding to the indazole derivatives of formula IB as defined above wherein —F—G— represents —CH₂—N— and R¹ is hydrogen, may be prepared by a process which comprises cyclising a compound of formula XIII:

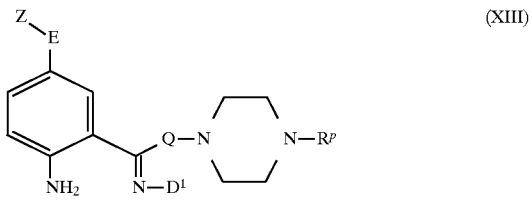

wherein Z, E, Q and R^P are as defined above, and D¹ represents a readily displaceable group; followed, where required, by N-alkylation by standard methods to introduce the moiety R³; with subsequent removal of the amino-protecting group R^P.

Similarly, the compounds of formula I wherein T represents CH, U represents nitrogen and V represents N—R³— i.e. the indazole derivatives of formula IB as defined above—may be prepared by a process which comprises cyclising a compound of formula XIV:

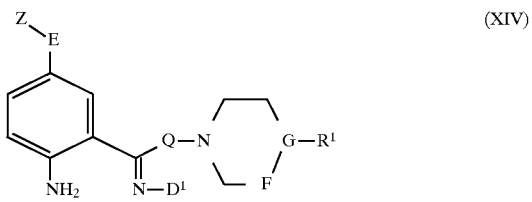

in which Z, E, Q, F, G, R¹ and D¹ are as defined above.

The cyclisation of compounds XIII and XIV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIII and XIV suitably represents a $C_{1-4}$ alkanoyloxy group, preferably acetoxy. Where $D^1$ represents acetoxy, the desired compound of formula XIII or XIV may be conveniently prepared by treating a carbonyl compound of formula XV:

wherein Z, E, Q, F and G are as defined above, and $R^x$ corresponds to the group $R^1$ as defined above, or $R^x$ represents an amino-protecting group as defined for $R^p$ when —F—G— represents —CH$_2$—N—; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XV may conveniently be prepared by ozonolysis of the corresponding indole derivative of formula XVI:

wherein Z, E, Q, F, G and $R^x$ are as defined above; followed by a reductive work-up, advantageously using dimethylsulphide.

The indole derivatives of formula XVI may be prepared by methods analogous to those described in the accompanying Examples, or by procedures well known from the art.

In a still further procedure, the compounds of formula III above wherein T represents CH, U represents C—$R^2$ and V represents oxygen or sulphur, corresponding to the benzofuran or benzthiophene derivatives of formula IA wherein V is oxygen or sulphur respectively, —F—G— represents —CH$_2$—N— and $R^1$ is hydrogen, may be prepared by a process which comprises cyclising a compound of formula XVII:

wherein Z, E, Q, $R^2$ and $R^p$ are as defined above, and VI represents oxygen or sulphur; followed by removal of the amino-protecting group $R^p$.

Similarly, the compounds of formula I wherein T represents CH, U represents C—$R^2$ and V represents oxygen or sulphur—i.e. the benzofuran or benzthiophene derivatives of formula IA above—may be prepared by a process which comprises cyclising a compound of formula XVIII:

wherein Z, E, Q, F, G, $R^1$, $R^2$ and $V^1$ are as defined above.

The cyclisation of compounds XVII and XVIII is conveniently effected by using polyphosphoric acid or a polyphosphate ester, advantageously at an elevated temperature.

The compounds of formula XVII and XVIII may be prepared by reacting a compound of formula XIX with a compound of formula XX:

wherein Z, E, Q, F, G, $R^2$, $V^1$ and $R^x$ are as defined above, and Hal represents a halogen atom.

The reaction is conveniently effected in the presence of a base such as sodium hydroxide.

The hydroxy and mercapto derivatives of formula XIX may be prepared by a variety of methods which will be readily apparent to those skilled in the art. One such method is described in EP-A-0497512.

In a yet further procedure, the compounds of formula III above may be prepared by a process which comprises reducing a compound of formula XXI:

wherein Z, E, T, U, V and $R^p$ are as defined above, and —$Q^2$—CH$_2$— corresponds to the moiety Q as defined above; with subsequent removal of the amino-protecting group $R^p$.

The reaction is suitably carried out by treating the compound of formula XXI with a reducing agent such as lithium aluminium hydride in an appropriate solvent, e.g. diethyl ether or tetrahydrofuran, or mixtures thereof.

Similarly, the compounds according to the invention may be prepared by a process which comprises reducing a compound of formula XXII:

wherein Z, E, T, U, V, F, G, $R^1$ and $Q^2$ are as defined above.

As with compound XXI, the reduction is conveniently effected by treating compound XXII with a reducing agent such as lithium aluminium hydride in an appropriate solvent, e.g. diethyl ether or tetrahydrofuran, or mixtures thereof.

The compounds of formulae XXI and XXII above may suitably be prepared by reacting a compound of formula XXIII with the appropriate compound of formula XXIV:

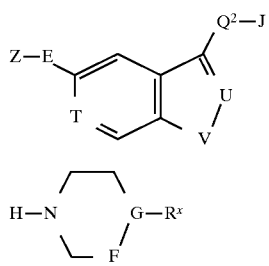

wherein Z, E, T, U, V, F, G, R$^x$ and Q$^2$ are as defined above, and J represents a reactive carboxylate moiety.

Suitable values for the reactive carboxylate moiety J include esters, for example C$_{1-4}$ alkyl esters; acid anhydrides, for example mixed anhydrides with C$_{1-4}$ alkanoic acids; acid halides, for example acid chlorides; and acylimidazoles.

By way of example, the intermediates of formula XXIII above wherein J is an acid chloride moiety may be prepared by treating the corresponding carboxylic acid derivative with thionyl chloride in toluene. Similarly, the intermediates of formula XXIII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XXIV.

The hydrazine derivatives of formula IV above may be prepared by methods analogous to those described in EP-A-0438230 and EP-A-0497512.

Where they are not commercially available, the starting materials of formula VII, VIII, XI, XX, XXIII and XXIV may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein —F—G— represents —CH=C— initially obtained may be readily converted into the corresponding compound wherein —F—G— represents —CH$_2$—CH— by conventional catalytic hydrogenation procedures. In addition, a compound of formula I wherein R$^1$ is benzyl initially obtained may be converted by catalytic hydrogenation to the corresponding compound of formula III, which in turn may be converted into a further compound of formula I using standard N-alkylation techniques as described above. Furthermore, a compound of formula I initially obtained wherein the R$^1$ moiety is substituted by nitro or cyano may be converted by catalytic hydrogenation to the corresponding amino- or aminomethyl-substituted compound respectively. Additionally, a compound of formula I wherein the R$^1$ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the R$^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the R$^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein R$^3$ is hydrogen initially obtained may be converted into a compound of formula I wherein R$^3$ represents C$_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D\alpha}$/5-HT$_{1D\beta}$ Radioligand Binding

Chinese hamster ovary (CHO) clonal cell lines expressing the human 5-HT$_{1D\alpha}$ and 5-HT$_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 $\mu$M was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of $\alpha$-[$^{33}$P]-ATP to [$^{33}$P]-cyclic AMP. A 10 $\mu$l aliquot of the membrane suspension was incubated, for 10–15 min, in a final volume of 50 $\mu$l, at 30° C., with or without forskolin (10 $\mu$M), in the presence or absence of test compound. The incubation buffer consisted of 50 mM Tris HCl (pH 7.6 at room temperature), 100 mM NaCl, 30 $\mu$M GTP, 50 $\mu$M cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 $\mu$Ci $\alpha$-[$^{33}$P]-ATP and 1 nCi [$^3$H]-cyclic AMP. The incubation was initiated by the addition of membrane, following a 5 min preincubation at 30° C., and was terminated by the addition of 100 $\mu$l SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTP$\gamma$S Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 $\mu$g protein/ml for the 5-$HT_{1D\alpha}$ receptor transfected cells and 40–50 $\mu$g protein/ml for the 5-$HT_{1D\beta}$ receptor transfected cells. The membrane suspension was then incubated, in a volume of 1 ml, with GDP (100 $\mu$M for 5-$HT_{1D\alpha}$ receptor transfected cells, 30 $\mu$M for the 5-$HT_{1D\beta}$ receptor transfected cells) and test compound at 30° C. for 20 min and then transferred to ice for a further 15 min. [$^{35}$S]-GTP$\gamma$S was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1

1-(3-[5-(1,2,4-Triazol-4-yl)-1H-indol-3-yl]propyl)-4-(4-(acetamido)benzyl)piperazine. Hydrogen Succinate. Monohydrate 1. Intermediate 1: 4'-(1,2,4-Triazol-4-yl)phenylhydrazine a) 4'-Aminoacetanilide A solution of 4-nitroacetanilide (5.0 g, 27.8 mmol) in EtOH/EtOAc (160 ml, 1:1), $H_2O$ (15 ml) and 5N HCl (5.6 ml, 28.0 mmol) was hydrogenated over 10% Pd-C (0.50 g) at 50 psi for 0.25 h. The catalyst was removed by filtration through celite and the solvents removed under vacuum. The free base was generated by dissolving the product in $H_2O$, basifying with 2N NaOH and extracting into EtOAc. The combined extracts were dried ($MgSO_4$) and evaporated to give the title-aniline (3.75 g, 90%). $\delta$ (250 MHz, $CDCl_3$/$d_4$-MeOH) 2.10 (3H, s, Me); 6.68 (2H, d, J=8.8Hz, Ar-H); 7.27 (2H, d, J=8.8Hz, Ar-H).

b) 4'-(1,2,4-Triazol-4-yl)acetanilide

A mixture of the preceding aniline (3.52 g, 23.4 mmol), N,N-dimethylformamide azine (3.33 g, 23.4 mmol; *J. Chem.*

Soc. (C), 1967, 1664) and p-toluenesulphonic acid monohydrate (0.223 g, 1.17 mmol), in anhydrous toluene (100 ml) was heated at reflux for 17 h. The beige coloured precipitate was filtered off and washed with toluene and $CH_2Cl_2$ and dried under vacuum to give the desired triazole (4.29 g, 91%); δ (250 MHz, $d_4$-MeOH/$d_6$-DMSO) 2.14 (3H, s, $CH_3$); 7.60 (2H, d, J=8.8Hz, Ar-H); 7.78 (2H, d, J=8.8Hz, Ar-H); 8.96 (2H, s, Ar-H).

c) 4'-(1,2,4-Triazol-4-yl)phenylaniline

A solution of the preceding acetanilide (4.91 g, 24.3 mmol) in 5N HCl (100 ml) was heated at 125° C. for 1.5 h. The mixture was cooled to 0° C., basified with concentrated aqueous NaOH solution and extracted with $CH_2Cl_2$ (×5). The combined extracts were dried ($MgSO_4$) and evaporated and the residue chromatographed on silica gel, eluting with $CH_2Cl_2$/MeOH/$NH_3$ (80:8:1), to give the title-aniline (2.94 g, 76%); δ (250 MHz, $CDCl_3$) 3.80 (2H, s, $NH_2$); 6.71 (2H, d, J=8.8Hz, Ar-H); 7.08 (2H, d, J=8.8Hz, Ar-H); 8.36 (2H, s, Ar-H).

d) 4'-(1,2,4-Triazol-4-yl)phenylhydrazine

To a solution of the preceding aniline (1.60 g, 9.99 mmol) in concentrated HCl/$H_2O$ (23 ml and 3 ml respectively) was added, at −21° C., a solution of $NaNO_2$ (0.69 g, 9.99 mmol) in $H_2O$ (8 ml), at such a rate as to maintain the temperature below −10° C. The mixture was stirred for 0.3 h and then filtered rapidly through a sinter, under vacuum. The filtrate was added to a cooled (−20° C.) solution of $SnCl_2.2H_2O$ (9.02 g, 40.0 mmol) in concentrated HCl (17 ml). The mixture was stirred at −20° C. for 0.25 h and then at room temperature for 1.25 h. The resulting solid was filtered off, washed with $Et_2O$ and dried under vacuum. The crude product was dissolved in $H_2O$, basified with concentrated aqueous NaOH and extracted with EtOAc (×5). The combined extracts were dried ($MgSO_4$) and evaporated to afford the title-product (0.95 g, 54%); δ (250 MHz, $CDCl_3$/$d_4$-MeOH) 3.98 (3H, br s, NH and $NH_2$); 6.97 (2H, d, J=12.0Hz, Ar-H); 7.25 (2H, d, J=12.0Hz, Ar-H); 8.48 (2H, s, Ar-H).

2. Intermediate 2: 1-(3-[5-(1,2,4-Triazol-4-yl)-1H-indol-3-yl]propyl)-4-(H)-piperazine. 3.5 Hydrogen Oxalate 1. 5-(4-tert-Butyloxycarbonyl)piperazin-1-yl pentanal dimethyl acetal a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine, dried ($Na_2SO_4$) and evaporated. The crude product was chromatographed on silica gel eluting with diethyl ether/hexane (1:9) to give the title-acetal (27.5 g, 57%). δ (250 MHz, $CDCl_3$) 1.43–1.67 (4H, m, 2 of $CH_2$); 1.83–1.94 (2H, m, $CH_2$); 3.38 (6H, s, CH(OMe)$_2$); 3.42 (2H, t, J=7Hz, $CH_2$Br), 4.37 (1H, t, J=7Hz, C$\underline{H}$(OMe)$_2$).

b) 5-(4-tert-Butyloxycarbonyl)piperazin-1-yl pentanal dimethyl acetal

A mixture of 5-bromovaleraldehyde dimethyl acetal (27.5 g, 0.13 mol), $Na_2CO_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250 MHz, $CDCl_3$) 1.29–1.71 (6H, m, 3 of $CH_2$); 1.46 (9H, s, OC(Me)$_3$); 2.31–2.39 (6H, m, 3 of $CH_2$); 3.32 (6H, s, CH(OM$\underline{e}_2$); 3.41–3.45 (4H, m, 2 of $CH_2$); 4.36 (1H, t, J=6Hz, C$\underline{H}$(OMe)$_2$).

2. 1-(3-[5-(1,2,4-Triazol-4-yl)-1H-indol-3-yl]propyl)-4-(H)-piperazine. 3.5 Hydrogen Oxalate A mixture of Intermediate 1 (5.0 g, 28.6 mmol) and 5-(4-tert-butyloxycarbonyl)piperazin-1-yl pentanal dimethylacetal (9.03 g, 28.6 mmol) in 4% sulphuric acid (150 ml) was heated at reflux for 48 h. The solution was cooled in an ice-bath, basified with solid $K_2CO_3$ and extracted with butan-1-ol (×3). The solvent was removed under vacuum and azeotroped with hexane (×2). The crude product was purified by chromatography on silica gel eluting with $CH_2Cl_2$/MeOH/$NH_3$ (30:8:1) to give the title-indole (3.9 g, 44%). The 3.5 hydrogen oxalate salt was prepared using 200 mg of free base: mp 90°–92° C. (Found: C, 45.97; H, 4.76; N, 13.77. $C_{17}H_{22}N_6.3.5(C_2H_2O_4)$ requires C, 46.08; H, 4.76; N, 13.43%); δ (360 MHz, $D_2O$) 2.12–2.24 (2H, m, $CH_2$); 2.93 (2H, t, J=7Hz, $CH_2$); 3.46–3.76 (8H, m, 4 of $CH_2$); 7.37 (1H, dd, J=1.9 and 8.7Hz, Ar-H); 7.39 (1H, s, Ar-H); 7.66 (1H, d, J=8.7, Ar-H); 7.82 (1H, d, J=1.9Hz, Ar-H); 9.13 (2H, s, Triazole-H).

3. 1-(3-[5-(1,2,4-Triazol-4-yl)-1H-indol-3-yl]propyl)-4-(4-(acetamido)benzyl)piperazine. Hydrogen Succinate Monohydrate To a solution of Intermediate 2 (0.25 g, 0.81 mmol), glacial acetic acid (0.12 g, 2.0 mmol) and sodium cyanoborohydride (0.097 g, 1.6 mmol), in anhydrous methanol (20 ml), at 0° C. was added a solution of 4-acetamidobenzaldehyde (0.16 g, 0.98 mmol), in methanol (5 ml). The mixture was warmed to room temperature and stirred for 16 h. Saturated $K_2CO_3$ solution (3 ml) was added and the solvent removed under reduced pressure. EtOAc (50 ml) and water (10 ml) were added to the residue and the aqueous separated and extracted further with EtOAc (×2). The combined extracts were washed with brine (×2), dried ($Na_2SO_4$) and evaporated. The crude product was chromatographed on silica gel eluting with $CH_2Cl_2$/MeOH/$NH_3$ (70:8:1) to give the title-product (0.18 g, 50%). The hydrogen succinate monohydrate salt was prepared: mp 92°–94° C.; (Found: C, 60.77; H, 6.65; N, 16.30. $C_{26}H_{31}N_7O.(C_4H_6O_4).H_2O$ requires C, 60.69; H, 6.62; N, 16.51%); δ (250 MHz, $D_2O$) 2.10–2.26 (2H, m, $CH_2$); 2.28 (3H, s, NHCOM$\underline{e}$); 2.60 (4H, s, succinate); 2.82–3.32 (12H, m, 6 of $CH_2$); 3.86 (2H, s, C$\underline{H}_2$Ar); 7.35 (1H, dd, J=2.1 and 8.8Hz, Ar-H); 7.44 (1H, s, Ar-H); 7.46 (2H, d, J=8.6Hz, Ar-H); 7.54 (2H, d, J=8.6Hz, Ar-H); 7.69 (1H, d, J=8.8Hz, Ar-H); 7.78 (1H, d, J=2.1Hz, Ar-H); 8.89 (2H, s, Triazole-H).

EXAMPLE 2

1-(4-[5-(1,2,4-Triazol-4-yl)-1H-indol-3-yl]butyl)-4-(4-acetamido)benzyl)piperazine. 2.1 Hydrogen Oxalate. 1.5 Hydrate 1. Intermediate 3: 1-(4-[5-(1,2,4-Triazol-4-yl)-1H-indol-3-yl]butyl)-4-(H)-piperazine a) 6-(4-tert-Butoxycarbonyl)piperazin-1-yl hexanal dimethyl acetal The title-compound was prepared from 6-bromohexanoyl chloride using the procedure described for Intermediate 2 part 1. δ (360 MHz, CDCl$_3$) 1.30–1.63 (8H, m, 4 of CH$_2$); 1.46 (9H, s, OC(Me)$_3$); 2.31–2.40 (6H, m, 3 of CH$_2$); 3.31 (6H, s, CH(OMe)$_2$); 3.40–3.46 (4H, m, 2 of CH$_2$); 4.35 (1H, t, J=5.7Hz, CH(OMe)$_2$).

b) 1-(4-[5-(1,2,4-Triazol-4-yl)-1H-indol-3-yl]butyl)-4-(H)-piperazine

A solution of Intermediate 1 (1.0 g, 5.71 mmol) and Intermediate 3 (1.9 g, 5.76 mmol), in 4% H$_2$SO$_4$ (100 ml), was heated at reflux for 20 h. The mixture was cooled to room temperature, basified with K$_2$CO$_3$ and extracted with n-butanol (×4). The crude product remaining after removing the solvent under vacuum, and azeotroping with hexane (×2), was chromatographed on silica gel eluting with CH$_2$Cl$_2$/MeOH/NH$_3$ (30:8:1) to give the title-product (0.7 g, 38%). δ (360 MHz, d$_6$-DMSO) 1.44–1.52 (2H, m, CH$_2$); 1.62–1.70 (2H, m, CH$_2$); 2.23–2.27 (6H, m, 3 of CH$_2$); 2.62–2.65 (4H, m, 2 of CH$_2$); 2.71 (2H, t, J=7.4Hz, CH$_2$); 7.26 (1H, s, Ar-H); 7.29 (1H, dd, J=2.1 and 8.5Hz, Ar-H); 7.47 (1H, d, J=8.5Hz, Ar-H); 7.77 (1H, d, J=2.1Hz, Ar-H); 9.01 (2H, s, Triazole-H); 11.05 (1H, s, NH).

2. 1-(4-[5-(1,2,4-Triazol-4-yl)-1H-indol-3-yl]butyl)-4-(4-(acetamido)benzyl)piperazine. 2.1 Hydrogen Oxalate. 1.5 Hydrate Prepared from 1-(4-[5-(1,2,4-triazol-4-yl)-1H-indol-3-yl]butyl)-4-(H)-piperazine using the general reductive amination procedure described for Example 1. The product was obtained in 59% yield and the 2.1 hydrogen oxalate 1.5 hydrate salt prepared: mp 202°–204° C. (Found: C, 54.70; H, 5.83; N, 14.08. C$_{27}$H$_{33}$N$_7$O.2.1(C$_2$H$_2$O$_4$).1.5H$_2$O requires C, 54.49; H, 5.89; N, 14.26%); δ (360 MHz, D$_2$O) 1.77 (4H, br s, 2 of CH$_2$); 2.17 (3H, s, Me); 2.83 (2H, br s, CH$_2$); 3.24 (2H, br s, CH$_2$); 3.51 (8H, br s, 4 of CH$_2$); 4.35 (2H, s, CH$_2$Ar); 7.30 (1H, dd, J=2.0 and 8.6Hz, Ar-H); 7.33 (1H, s, Ar-H); 7.46 (2H, d, J=8.5Hz, Ar-H); 7.52 (2H, d, J=8.5Hz, Ar-H); 7.61 (1H, d, J=8.6Hz, Ar-H); 7.74 (1H, d, J=2.0Hz, Ar-H); 8.89 (2H, s, Triazole-H).

EXAMPLE 3

1-(3-[5-(1,2,4-Triazol-4-yl)-1H-indol-3-yl]propyl)-4-(2-(methoxy)benzyl)piperazine. Trihydrogen Oxalate The title-compound was prepared from Intermediate 2 and 2-methoxybenzaldehyde using the general procedure described for Example 1. The trihydrogen oxalate salt was prepared: mp 206°–208° C. (Found: C, 53.20; H, 5.57; N, 11.88. C$_{25}$H$_{30}$N$_6$O.3(C$_2$H$_2$O$_4$) requires C, 53.14; H, 5.18; N, 11.99%); m/e 431 (M+1)$^+$; δ (360 MHz, D$_2$O) 2.10–2.22 (2H, m, CH$_2$); 2.91 (2H, t, J=6.9Hz, CH$_2$); 3.27–3.31 (2H, m, CH$_2$); 3.63 (8H, br s, 4 of CH$_2$); 3.88 (3H, s, OMe); 4.47 (2H, s, CH$_2$Ar); 7.05–7.09 (1H, m, Ar-H); 7.14 (1H, dd, J=1.8 and 8.6Hz, Ar-H); 7.34–7.41 (3H, m, Ar-H); 7.52–7.57 (1H, m, Ar-H); 7.64 (1H, d, J=8.6Hz, Ar-H); 7.80 (1H, d, J=1.8Hz, Ar-H); 9.17 (2H, s, Triazole-H).

EXAMPLE 4

1-(3-[5-(1,2,4-Triazol-4-yl)-1H-indol-3-yl]propyl)-4-(benzyl)piperazine. 2.25 Hydrogen Maleate Prepared from Intermediate 2 and benzaldehyde using the general procedure. The 2.25 hydrogen maleate salt was prepared: mp 167°–169° C. (Found: C, 58.36; H, 5.55; N, 12.53. C$_{24}$H$_{28}$N$_6$.2.25(C$_4$H$_4$O$_4$) requires C, 58.31; H, 5.78; N, 12.36%); m/e 401 (M+1)$^+$; δ (360 MHz, d$_6$-DMSO) 1.93–2.06 (2H, m, CH$_2$); 2.76 (2H, t, J=7.3Hz, CH$_2$); 2.78–3.60 (10H, m, 5 of CH$_2$); 3.65 (2H, br s, CH$_2$Ph); 6.14 (5H, s, maleate-H); 7.26–7.38 (7H, m, Ar-H); 7.50 (1H, d, J=8.5Hz, Ar-H); 7.79 (1H, d, J=2.0Hz, Ar-H); 9.01 (2H, s, Triazole-H); 11.16 (1H, s, NH).

Examples 5–7 inclusive were prepared from Intermediate 2 and the appropriate pyridine carboxaldehyde using the general reductive amination procedure.

EXAMPLE 5

1-(3-[5-(1,2,4-Triazol-4-yl)-1H-indol-3-yl]propyl)-4-(pyridin-3-ylmethyl)piperazine. 6.25 Hydrogen Oxalate 0.8 Hydrate mp: 182°–184° C. (Found: C, 43.69; H, 4.29; N, 9.86.C$_{23}$H$_{27}$N$_7$. 6.25(C$_2$H$_2$O$_4$).0.8H$_2$O requires C, 43.57; H, 4.23; N, 10.02%); δ (250 MHz, CDCl$_3$; free base) 1.87–1.99 (2H, m, CH$_2$); 2.44–2.66 (10H, m, 5 of CH$_2$); 2.79 (2H, t, J=7.4Hz, CH$_2$); 3.52 (2H, s, CH$_2$Ar); 7.14 (1H, dd, J=2.1 and 8.6Hz, Ar-H), 7.17 (1H, d, J=2.2Hz, Ar-H); 7.23–7.28 (1H, m, Pyridyl-H); 7.48 (1H, d, J=8.6Hz, Ar-H); 7.57 (1H, d, J=2.1Hz, Ar-H); 7.66 (1H, d, J=1.8 and 7.8Hz, Pyridyl-H); 8.46 (2H, s, Triazole-H); 8.48–8.54 (2H, m, Pyridyl-H); 8.85 (1H, s, NH).

EXAMPLE 6

1-(3-[5-(1,2,4-Triazol-4-yl)-1H-indol-3-yl]propyl)-4-(pyridin-2-ylmethyl)piperazine. 5.0 Hydrogen Oxalate Monohydrate mp: 124°–127° C. (Found: C, 45.41; H, 4.29; N, 11.33. C$_{23}$H$_{27}$N$_7$. 5.0(C$_2$HO$_4$).1.0H$_2$O requires C, 45.57; H, 4.52; N, 11.27%); δ (360 MHz, D$_2$O) 2.10–2.24 (2H, m, CH$_2$); 2.66–3.64 (12H, m, 6 of CH$_2$); 4.12 (2H, s, CH$_2$Ar); 7.39 (1H, d, J=8.7Hz, Ar-H); 7.40 (1H, s, Ar-H); 7.68 (1H, d, J=8.7Hz, Ar-H); 7.87 (1H, s, Ar-H); 7.94–8.00 (2H, m, Pyridyl-H); 8.51–8.54 (1H, m, Pyridyl-H); 8.70 (1H, d, J=6.7Hz, Pyridyl-H); 9.48 (2H, s, Triazole-H).

EXAMPLE 7

1-(3-[5-(1,2,4-Triazol-4-yl)-1H-indol-3-yl]propyl)-4-(pyridin-4-ylmethyl)piperazine. 3.2 Hydrogen Oxalate. Hemihydrate mp: 88°–90° C. (Found: C, 50.54; H, 4.86; N, 14.33.C$_{23}$H$_{27}$N$_7$. 3.2(C$_2$H$_2$O$_4$).0.5H$_2$O requires C, 50.70; H, 4.98; N, 14.13%); m/e 402 M+1)$^+$; δ (360 MHz, d$_6$-DMSO) 1.96–2.10 (2H, m, CH$_2$); 2.44–3.44 (12H, m, 6 of CH$_2$); 3.61 (2H, s, CH$_2$Ar);. 7.30–7.36 (4H, m, Ar-H); 7.50 (1H, d, J=8.6Hz, Ar-H); 7.80 (1H, s, Ar-H); 8.50–8.54 (2H, m, Ar-H); 9.02 (2H, s, Triazole-H); 11.19 (1H, s, NH).

EXAMPLE 8

1-(3-[5-(1,2,4-Triazol-4-yl)-1H-indol-3-yl]propyl)-4-(4-(amino)benzyl)piperazine. 4.1 Hydrogen Oxalate Reaction of Intermediate 2 with 4-nitrobenzaldehyde under standard reductive amination conditions gave 1-(3-[5-(1,2,4-triazol-4-yl)-1H-indol-3-yl]propyl)-4-(4-(nitro)benzyl)piperazine in 46% yield. PtO$_2$ (60 mg) was suspended in ethanol (40 ml) and stirred under an atmosphere of hydrogen for 0.75 h. The preceding nitrobenzyl piperazine (0.33 g, 0.74 mmol) was then added and the mixture stirred for 2 h. The catalyst was removed by filtration through celite, the solvent removed under vacuum and the residue chromatographed on silica gel eluting with $CH_2Cl_2$/ $MeOH/NH_3$ (70:8:1) to give the title-amino-benzyl piperazine (0.26 g, 85%). The 4.1 hydrogen oxalate salt was prepared: mp 150°–153° C. (Found: C, 49.04; H, 4.80; N, 12.76. $C_{24}H_{29}N_7.4.1(C_2H_2O_4)$ requires C, 49.28; H, 4.77; N, 12.49%); m/e 416 (M+1)⁺; δ (250 MHz, $d_6$-DMSO; free base) 1.72–1.86 (2H, m, $CH_2$); 2.16–2.44 (10H, m, 5 of $CH_2$); 2.70 (2H, t, J=7.4Hz, $CH_2$); 3.23 (2H, s, $CH_2$); 4.93 (2H, s, $NH_2$); 6.48 (2H, d, J=8.4Hz, Ar-H); 6.89 (2H, d, J=8.4Hz, Ar-H); 7.27 (1H, s, Ar-H); 7.29 (1H, dd, J=2.1 and 8.6Hz, Ar-H); 7.47 (1H, d, J=8.6Hz, Ar-H); 7.78 (1H, d, J=2.1Hz, Ar-H); 9.02 (2H, s, Triazole-H); 11.07 (1H, s, NH).

Examples 9–11 inclusive were prepared from 1-(4-[5-(1, 2,4-triazol-4-yl)-1H-indol-3-yl]butyl)-4-(H)-piperazine and the appropriate aromatic aldehyde using the general reductive amination conditions.

EXAMPLE 9

1-(4-[5-(1,2,4-Triazol-4-yl)-1H-indol-3-yl]butyl)-4-(benzyl)piperazine. 2.5 Hydrogen Oxalate mp: 216°–217° C. (Found: C, 56.54; H, 5.61; N, 13.23. $C_{25}H_{30}N_6$. $2.5(C_2H_2O_4)$ requires C, 56.33; H, 5.52; N, 13.15%); m/e 415 (M+1)⁺; δ (360 MHz, $d_6$-DMSO); 1.67 (4H, br s, 2 of $CH_2$); 2.46–3.26 (12H, m, 6 of $CH_2$); 3.61 (2H, s, C$\underline{H}_2$Ar); 7.26–7.38 (7H, m, Ar-H); 7.48 (1H, d, J=8.6Hz, Ar-H); 7.78 (1H, d, J=2.0Hz, Ar-H); 9.01 (2H, s, Triazole-H); 11.13 (1H, s, NH).

EXAMPLE 10

1-(4-[5-(1,2,4-Triazol-4-yl)-1H-indol-3-yl]butyl)-4-(pyridin-2-ylmethyl)piperazine. Sesquioxalate Monohydrate mp: 115°–118° C. (Found: C, 56.94; H, 6.13; N, 17.50. $C_{24}H_{29}N_7$. $1.5(C_2H_2O_4).H_2O$ requires C, 57.03; H, 6.03; N, 17.24%); m/e 416 (M+1)⁺; δ (360 MHz, $d_6$-DMSO) 1.67 (4H, br s, 2 of $CH_2$); 2.46–3.26 (12H, m, 6 of $CH_2$); 3.71 (2H, s, C$\underline{H}_2$Ar); 7.28–7.32 (3H, m, Ar-H); 7.43 (1H, d, J=7.8Hz, Pyridyl-H); 7.49 (1H, d, J=8.6Hz, Ar-H); 7.77–7.82 (2H, m, Ar-H); 8.49 (1H, d, J=4.0Hz, Pyridyl-H); 9.01 (2H, s, Triazole-H); 11.14 (1H, s, NH).

EXAMPLE 11

1-(4-[5-(1,2,4-Triazol-4-yl)-1H-indol-3-yl]butyl)-4-(pyridin-3-ylmethyl)piperazine. Sesquioxalate mp: 110°–112° C. (Found: C, 58.80; H, 6.17; N, 18.09. $C_{24}H_{29}N_7.1.5(C_2H_2O_4)$ requires C, 58.90; H, 5.86; N, 17.81%); m/e 416 (M+1)⁺; δ (360 MHz, $d_6$-DMSO) 1.67 (4H, br s, 2 of $CH_2$); 2.44–3.20 (12H, m, 6 of $CH_2$); 3.59 (2H, s, C$\underline{H}_2$Ar); 7.29 (1H, s, Ar-H); 7.30 (1H, dd, J=2.1 and 8.6Hz, Ar-H); 7.38 (1H, dd, J=5.0 and 8.1Hz, Pyridyl-H); 7.48 (1H, d, J=8.7Hz, Ar-H); 7.71 (1H, d, J=8.1Hz, Pyridyl-H); 7.78 (1H, d, J=2.1Hz, Ar-H); 8.46–8.52 (2H, m, Pyridyl-H); 9.01 (2H, s, Triazole-H); 11.12 (1H, s, NH).

EXAMPLE 12

1-(3-[5-(1,2,4-Triazol-4-yl)-1H-indol-3-yl]propyl)-4-(4-(amino)phenethyl)piperazine. Trihydrogen Oxalate. 1.2 Hydrate 1. 1-(3-[5-(1,2,4-Triazol-4-yl)-1H-indol-3-yl]propyl)-4-(4-(nitro)phenethyl)piperazine A mixture of Intermediate 2 (0.30 g, 0.97 mmol), $K_2CO_3$ (0.27 g, 1.94 mmol) and p-nitrophenethylbromide (0.223 g, 0.97 mmol), in anhydrous DMF (50 ml), was stirred at room temperature for 18 h. The mixture was poured into water (100 ml) and extracted with EtOAc (×3). The combined extracts were washed with $H_2O$ (×2) and brine (×2), dried ($Na_2SO_4$) and evaporated. The crude product was chromatographed on silica gel eluting with $CH_2Cl_2/MeOH/NH_3$ (90:8:1) to give the title-piperazine (0.23 g, 52%). δ (250 MHz, $CDCl_3$) 1.90–2.08 (2H, m, $CH_2$); 2.40–2.72 (12H, m, 6 of $CH_2$); 2.81 (2H, t, J=7.4Hz, $CH_2$); 2.91 (2H, t, J=7.4Hz, $CH_2$); 7.16 (1H, dd, J=2.1 and 8.6Hz, Ar-H), 7.19 (1H, s, Ar-H); 7.36 (2H, d, J=8.8Hz, Ar-H); 7.48 (1H, d, J=8.6Hz, Ar-H); 7.57 (1H, d, J=2.1Hz, Ar-H); 8.15 (2H, d, J=8.8Hz, Ar-H); 8.36 (1H, br s, NH); 8.48 (2H, s, Triazole-H).

2. 1-(3-[5-(1,2,4-Triazol-4-yl)-1H-indol-3-yl]propyl)-4-(4-(amino)phenethyl)piperazine. Trihydrogen Oxalate 1.2 Hydrate Prepared from the preceding 4-(nitro)phenethyl piperazine as described for Example 8. The trihydrogen oxalate 1.2 hydrate salt was prepared: mp 122°–125° C. (Found: C, 51.82; H, 5.11; N, 13.22. $C_{25}H_{31}N_7.3.0(C_2H_2O_4).1.2H_2O$ requires C, 51.62; H, 5.51; N, 13.59%); δ (360 MHz, $d_6$l-DMSO) 1.90–2.02 (2H, m, $CH_2$); 2.62–3.06 (16H, m, 8 of $CH_2$); 6.52 (2H, d, J=8.3Hz, Ar-H); 6.89 (2H, d, J=8.3Hz, Ar-H); 7.30–7.33 (2H, m, Ar-H); 7.49 (1H, d, J=8.7Hz, Ar-H); 7.79 (1H, d, J=2.0Hz, Ar-H); 9.02 (2H, s, Triazole-H); 11.15 (1H, s, NH).

EXAMPLE 13

1-(3-[5-(1,2,4-Triazol-4-yl)-1H-indol-3-yl]propyl)-4-(4-(acetamido)phenethyl)piperazine. 2.75 Hydrogen Oxalate. Hemihydrate Acetyl chloride (0.020 g, 0.26 mmol) was added dropwise to a solution of Example 12 (0.10 g, 0.23 mmol) and $NEt_3$ (0.026 g, 0.26 mmol), in anhydrous dichloromethane (5 ml), at 0° C. The solution was warmed to room temperature and stirred for 18 h. Dichloromethane (100 ml) was added and the solution washed with water (×2) and brine (×1). The dichloromethane was dried ($Na_2SO_4$) and evaporated and the residue chromatographed on silica gel eluting with $CH_2Cl_2/MeOH/NH_3$ (90:8:1) to give the title-acetamide (0.078 g, 71%). The 2.75 hydrogen oxalate hemihydrate salt was prepared: mp 217°–219° C. (Found: C, 53.74; H, 5.57; N, 13.37. $C_{27}H_{33}N_7O.2.75(C_2H_2O_4).0.5H_2O$ requires C, 53.60; H, 5.47; N, 13.46%); m/e 472 (M+1)⁺; δ (360 MHz, $d_6$-DMSO) 1.90–2.08 (2H, m, $CH_2$); 2.02 (3H, s, NHCOM$\underline{e}$); 2.66–3.16 (16H, m, 8 of $CH_2$); 7.14–7.16 (2H, d, J=8.4Hz, Ar-H); 7.33 (2H, br s, Ar-H); 7.47–7.51 (3H, m, Ar-H); 7.79 (1H, s, Ar-H); 9.02 (2H, s, Triazole-H); 9.87 (1H, s, N$\underline{H}$COMe); 11.16 (1H, s, NH).

EXAMPLE 14

1-(3-[5-(1,2,4-Triazol-4-yl)-1H-indol-3-yl]propyl)-4-(imidazol-2-ylmethyl)piperazine. Trihydrogen Oxalate. Hemihydrate The title-compound was prepared from Intermediate 2 and imidazole-2-carboxaldehyde using the general reductive amination procedure. The trihydrogen oxalate hemihydrate salt was prepared: mp 133°–135° C. (Found: C, 48.25; H, 4.93; N, 16.90. $C_{21}H_{26}N_8.3.0(C_2H_2O_4).0.5H_2O$ requires C, 48.43; H, 4.97; N, 16.73%); m/e 391 (M+1)⁺; δ (360 MHz, $D_2O$) 2.04–2.20 (2H, m, $CH_2$); 2.50–2.70 (2H, br m, $CH_2$); 2.87 (2H, t, J=7.0Hz, $CH_2$); 2.94–3.24 (6H, m, 3 of $CH_2$); 3.42–3.60 (2H, m, $CH_2$); 3.98 (2H, s, $CH_2$); 7.32 (1H, d, J=8.7Hz, Ar-H); 7.34 (1H, s, Ar-H); 7.38 (2H, s, Imidazole-H); 7.61 (1H, d, J=8.7Hz, Ar-H); 7.77 (1H, s, Ar-H); 9.12 (2H, s, Triazole-H).

EXAMPLE 15

1-(3-[5-(1,2,4-Triazol-4-yl)-1H-indol-3-yl]propyl)-4-(3-(acetamido)benzyl)piperazine. Trihydrogen oxalate. Monohydrate 1. 1-(3-[5-(1,2,4-Triazol-4-yl)-1H-indol-3-yl]propyl)-4-(3-(amino)benzyl)piperazine The title-compound was prepared from Intermediate 2 and 3-nitrobenzaldehyde as described for Example 8.

2. 1-(3-[5-(1,2,4-Triazol-4-yl)-1H-indol-3-yl]propyl)-4-(3-(acetamido)benzyl)piperazine. Trihydrogen Oxalate. Monohydrate Prepared from the preceding compound using the procedure described for Example 13. The trihydrogen oxalate monohydrate salt was prepared: mp 208°–210° C. (Found: C, 51.36; H, 5.23; N, 13.15. $C_{26}H_{31}N_7O.3.0(C_2H_2O_4).H_2O$ requires C, 51.54; H, 5.27; N, 13.15%); δ (360 MHz, $d_6$-DMSO) 1.96–2.06 (2H, m, $CH_2$); 2.03 (3H, s, NHCO$\underline{Me}$); 2.50–3.30 (12H, m, 6 of $CH_2$); 3.57 (2H, s, $C\underline{H}_2Ar$); 6.98 (1H, d, J=7.6Hz, Ar-H); 7.25 (1H, dd, J=7.6 and 8.5Hz, Ar-H); 7.32 (1H, dd, J=1.9 and 8.6Hz, Ar-H); 7.33 (1H, s, Ar-H); 7.43 (1H, d, J=8.6Hz, Ar-H); 7.50 (1H, d, J=8.6Hz, Ar-H); 7.61 (1H, s, Ar-H); 7.79 (1H, d, J=1.9Hz, Ar-H); 9.01 (2H, s, Triazole-H); 9.94 (1H, s, N$\underline{H}$COMe); 11.17 (1H, s, NH).

EXAMPLE 16

4-(4-Acetamido)benzyl-1-(3-[5-(1,2,4-triazol-4-yl)-1H-indol-3-yl]propyl)piperidine 1.5 Hydrogen Oxalate 1. 3-(5-[1,2,4-Triazol-4-yl]-1H-indol-3-yl)propan-1-ol A solution of 4'-(1,2,4-triazol-4-yl)phenylhydrazine (25 g, 143 mmol) in dioxan (250 ml) was treated with dihydropyran (24 g, 286 mmol) followed by 1M hydrochloric acid (150 ml) and heated at reflux for 18 hours. The reaction mixture was evaporated with toluene then reevaporated. Inorganic solids were removed by treating the residue with a mixture of methanol and acetonitrile. The mother liquors were purified by column chromatography on silica using dichloromethane:methanol (9:1→4:1) as the eluant. The compound was recrystallised from acetonitrile to afford the title compound as a white solid (10.24 g, 30%), mp 205°–207° C. δ (360 MHz, $d_6$-DMSO) 1.81 (2H, quintet, J=7Hz, $CH_2$), 2.75 (2H, t, J=8Hz, $CH_2$), 3.46 (2H, dt, $J_1$=6Hz, $J_2$=5Hz, $CH_2$), 4.43 (1H, t, J=5Hz, OH), 7.26 (1H, d, J=2Hz, Ar-H), 7.29 (1H, dd, $J_1$=9Hz, $J_2$=2Hz, Ar-H), 7.47 (1H, d, J=9Hz, Ar-H), 7.77 (1H, d, J=2Hz, Ar-H), 9.01 (2H, s, Triazole-H), 11.05 (1H, br s, indole NH). MS, $CI^+$, m/z for $(M+H)^+$=243.

2. 4-(4-Nitro)benzyl-1,2,5,6-tetrahydropyridine hydrochloride a) 1-Benzyl-4-(4-nitro)benzylpyridinium bromide A solution of 4-(4-nitro)benzylpyridine (10.4 g, 48 mmol) and benzyl bromide (5.8 ml, 48 mmol) in anhydrous acetone (50 ml) was stirred at room temperature for 18 hours. The precipitate was filtered off, washed with diethyl ether and dried under vacuum to give the desired quaternary salt (16.5 g, 90%), δ (250 MHz, $d_6$-DMSO) 4.47 (2H, s, $CH_2$), 5.82 (2H, s, $CH_2$), 7.38–7.60 (5H, m, Ar-H), 7.66 (2H, d, J=8.8Hz, Ar-H), 8.09 (2H, d, J=6.7Hz, Py-H), 8.23 (2H, d, J=8.8Hz, Ar-H), 9.15 (2H, d, J=6.7Hz, Py-H).

b) 1-Benzyl-4-(4-nitro)benzyl-1,2,5,6-tetrahydropyridine

Sodium borohydride (1.6 g, 43 mmol) was added dropwise to a cool (0° C.) suspension of the foregoing quaternary salt (16.5 g, 43 mmol) in ethanol (100 ml) and water (9 ml). The reaction mixture was stirred 18 hours at ambient temperature. The solvent was removed under vacuum and the residue partitioned between water and ethyl acetate. The organic layer was decanted, dried $Na_2SO_4$), evaporated and the crude product purified by flash chromatography on silica gel eluting with $CH_2Cl_2$/MeOH (98/2) to give the title compound (12 g, 91%). δ (250 MHz, $d_6$-DMSO) 1.93 (2H, br s, $CH_2$), 2.45 (2H, dd, $J_1$–$J_2$=6Hz, $CH_2$), 2.87 (2H, br s, $CH_2$), 3.41 (2H, s, $CH_2$), 3.49 (2H, s, $CH_2$), 5.44 (1H, br s, CH), 7.20–7.35 (5H, m, Ar-H), 7.46 (2H, d, J=8.6Hz, Ar-H), 8.17 (2H, J=8.6Hz, Ar-H).

c) 4-(4-Nitro)benzyl-1,2,5,6-tetrahydropyridine hydrochloride

To a cool (–5° C.) solution of the preceding benzyl amine (4.5 g, 14.6 mmol) in anhydrous dichloromethane was added, dropwise, α-chloroethylchloroformate (5 ml, 43 mmol). The solution was stirred whilst warming to room temperature, then stirred overnight. The mixture was evaporated to dryness and the residue was dissolved in methanol (100 ml) and heated at reflux for 2 hours. The solvent was evaporated and the solid recrystallised from MeOH/$CH_2Cl_2$ to give the desired amine (2.3 g, 63%). δ (250 MHz, $d_6$-DMSO) 2.14 (2H, br s, $CH_2$), 3.10 (2H, br d, J=5.4Hz, $CH_2$), 3.51 (4H, br s, 2 of $CH_2$), 5.55 (1H, br s, CH), 7.52 (2H, d, J=8.6Hz, Ar-H), 8.19 (2H, d, J=8.6Hz, Ar-H).

3. 4-(4-Nitro)benzyl-1-(3-[5-(1,2,4-triazol-4-yl)-1H-indol-3-yl]propyl-1,2,5,6-tetrahydropyridine To a suspension of 3-(5-[1,2,4-triazol-4-yl]-1H-indol-3-yl)-propan-1-ol (1 g, 4.14 mmol) in anhydrous tetrahydrofuran (100 ml) was added methane sulphonyl chloride (0.2 ml, 10 mmol) and triethylamine (1.3 ml, 10 mmol). The mixture was stirred for one hour at ambient temperature then the solvent was evaporated under vacuum and the residue partitioned between 10% aqueous potassium carbonate and dichloromethane. The aqueous was extracted with dichloromethane (3×) then the combined organics were washed with water, dried ($Na_2SO_4$) and evaporated. The residue was taken into isopropyl alcohol (100 ml) then treated with potassium carbonate (1.9 g, 13.7 mmol), sodium iodide (620 mg, 4.14 mmol), and 4-(4-nitro)benzyl-1,2,5,6-tetrahydropyridine (3 g, 13.7 mmol). The mixture was stirred at reflux, in the dark, for 18 hours, then the solvent was removed and the residue partitioned between water and dichloromethane. The organic layer was decanted, dried ($Na_2SO_4$) and evaporated. The crude product was purified by flash chromatography on silica eluting with MeOH/$CH_2Cl_2$ (5/95) to give the title compound (580 mg, 30%). δ (250 MHz, $d_6$-DMSO) 1.75–2.02 (4H, m, 2 of $CH_2$), 2.35–2.57 (4H, m, 2 of $CH_2$), 2.7 (2H, dd, $J_1$=$J_2$=7.2Hz, $CH_2$), 2.89 (2H, br s, $CH_2$), 3.40 (2H, s, $CH_2$), 5.43 (1H, br s, CH), 7.23–7.32 (2H, m, Ar-H), 7.38–7.50 (4H, m, Ar-H), 7.77 (1H, d, J=2Hz, Ar-H), 8.17 (2H, d, J=8.6Hz, Ar-H), 9.02 (2H, s, triazol-H), 11.07 (1H, br s, N-H).

4. 4-(4-Amino)benzyl-1-(3-[5-(1,2,4-triazol-4-yl)-1H-indol-3-yl]propyl)piperidine A suspension of platinum oxide (400 mg) in ethanol (50 ml) was hydrogenated for 30 minutes under one atmosphere of hydrogen. A solution of the foregoing indole (550 mg, 1.24 mmol) in ethanol (50 ml) was added and the mixture further hydrogenated for 4 hours. The catalyst was removed by filtration and the solvent evaporated under vacuum. The residue was purified by flash chromatography on silica eluting with $NH_3$/MeOH/$CH_2Cl_2$ (1:10:89) to give the title-product (270 mg, 52%). δ (250 MHz, $d_6$-DMSO) 1.01–1.20 (2H, m, $CH_2$), 1.21–1.41 (1H, m, CH), 1.42–1.56 (2H, m, $CH_2$), 1.66–1.86 (4H, m, 2 of $CH_2$), 2.20–2.38 (4H, m, 2 of CH$_2$), 2.64–2.75 (2H, m, CH$_2$), 2.75–2.89 (2H, m, CH$_2$), 4.80 (2H, br s, NH$_2$), 6.46 (2H, d, J=8.3Hz, Ar-H), 6.77 (2H, d, J=8.3Hz, Ar-H), 7.24–7.31 (2H, m, Ar-H), 7.46 (1H, d, J=8.6Hz, Ar-H), 7.78 (1H, d, J=2Hz, Ar-H), 9.01 (2H, s, triazol-H), 11.11 (1H br s, NH).

5. 4-(4-Acetamido)benzyl-1-(3-[5-(1,2,4-triazol-4-yl)-1H-indol-3-yl]propyl)piperidine 1.5 Hydrogen Oxalate Acetyl chloride (0.019 ml, 0.26 mmol) in anhydrous dichloromethane (2 ml) was added dropwide to a cool (0° C.) solution of the preceding aniline (100 mg, 0.24 mmol) and triethylamine (0.038 ml, 0.26 mmol) in anhydrous dichloromethane (10 ml). The solution was stirred whilst warming up for 5 hours at room temperature, then quenched with water. The organic layer was decanted, thoroughly washed with water, dried (Na$_2$SO$_4$) and evaporated. The residue was purified by flash chromatography on silica eluting with NH$_3$/MeOH/CH$_2$Cl$_2$ (1:10:89) to give the title compound (70 mg, 64%). The hydrogen oxalate salt had mp 166° C. (sintered), (Found: C, 60.52, H, 6.39, N, 14.13. C$_{27}$H$_{32}$N$_6$O.1.5(C$_2$H$_2$O$_4$).0.25H$_2$O requires C, 60.44, H, 6.00, N, 14.10%), δ (360 MHz, d$_6$-DMSO) 1.30–1.47 (2H, m, CH$_2$), 1.62–1.76 (3H, m, CH$_2$+CH), 1.96–2.10 (2H, m, CH$_2$), 2.01 (3H, s, CH$_3$), 2.43–2.54 (2H, m, CH$_2$), 2.75 (4H, dd, J$_1$=J$_2$=7.3Hz, 2 of CH$_2$), 2.96–3.10 (2H, m, CH$_2$), 3.32–3.48 (2H, m, CH$_2$), 7.07 (2H, d, J=8.4Hz, Ar-H), 7.29–7.36 (2H, m, Ar-H), 7.45–7.51 (3H, m, Ar-H), 7.79 (1H, d, J<2Hz, Ar-H), 9.01 (2H, s, triazol-H), 9.86 (1H, s, N—H), 11.18 (1H, s, N—H), MS, CI$^+$ m/e for (M+H)$^+$=457.

EXAMPLE 17

4-Benzyl-1-(3-[5-(1,2,4-triazol-4-yl)-1H-indol-3-yl]propyl)-1,2,5,6-tetrahydropyridine 1.85 Hydrogen Oxalate 1. 4-Benzyl-1,2,5,6-tetrahydropyridine a) 1,4-Bis-benzylpyridinium bromide A solution of 4-benzylpyridine (5.0 g, 29.5 mmol) in anhydrous acetone (25 ml) was treated with benzyl bromide (3.6 ml, 30 mmol) and stirred at room temperature for 18 hours. The precipitate was collected, washed with diethyl ether then dried to give the quaternary salt as a colourless solid (9.52 g, 95%). mp 214°–216° C. δ (360 MHz, D$_2$O) 4.29 (2H, s, CH$_2$), 5.74 (2H, s, CH$_2$), 7.30–7.52 (10H, m, Ar-H), 7.84 (2H, d, J=7Hz, Py-H), 8.68 (2H, d, Py-H).

b) 1,4-Bis-benzyl-1,2,5,6-tetrahydropyridine

A solution of the preceding quaternary salt (6.0 g, 17.6 mmol) in ethanol (30 ml) and water (3 ml) was cooled to 0° C. (ice/salt bath), then treated with sodium borohydride (0.67 g, 17.6 mmol) in four portions over 15 minutes. The reaction mixture was stirred at 0° C. for 2 hours then at room temperature for 4 hours. The mixture was evaporated in vacuo then the residue was partitioned between ethyl acetate (40 ml) and water (40 ml). The organic layer was separated and the aqueous re-extracted with ethyl acetate (40 ml). The combined organics were dried (sodium sulphate) then evaporated in vacuo to give the required tetrahydropyridine as an orange gum (3.96 g, 85%). R$_f$ 0.65 in ethyl acetate on silica plates. δ (360 MHz, CDCl$_3$) 2.04 (2H, br s, CH$_2$), 2.52 (2H, dd, J$_1$=J$_2$=5Hz, CH$_2$), 2.97 (2H, br s, CH$_2$), 3.28 (2H, s, CH$_2$), 3.56 (2H, s, CH$_2$), 5.36 (1H, dd, J$_1$=J$_2$=1.5Hz, CH$_2$), 7.15–7.34 (10H, m, Ar-H).

c) 4-Benzyl-1,2,5,6-tetrahydropyridine

A stirred, cooled (0° C., ice/salt bath) solution of the preceding amine (3.9 g, 14.8 mmol) in anhydrous dichloromethane (50 ml) was treated with α-chloroethylchloroformate (1.9 ml, 17.8 mmol) then stirred for 4 hours whilst warming to room temperature. The reaction mixture was evaporated to dryness in vacuo then the residue was treated with methanol (50 ml) and heated at reflux for 1 hour. The reaction mixture was evaporated to dryness then the residue was partitioned between dichloromethane (50 ml) and saturated potassium carbonate solution (50 ml). The organic layer was separated, the aqueous re-extracted with dichloromethane (50 ml), then the combined organics were dried (sodium sulphate) and evaporated in vacuo to give a red gum (2.9 g). The crude product was purified by column chromatography on silica using dichloromethane/methanol/ammonia (20:1:0.1) to afford the title product as a gum (1.0 g, 39%), δ (360 MHz, CDCl$_3$) 1.98 (2H, br s, CH$_2$), 2.95 (2H, dd, J$_1$=J$_2$=6Hz, CH$_2$), 3.28 (2H, s, CH$_2$), 3.32–3.37 (3H, m, CH$_2$ and NH), 5.45 (1H, dd, J$_1$=J$_2$=1Hz, CH), 7.15–7.30 (5H, m, Ar-H).

2. 4-Benzyl-1-(3-[5-(1,2,4-triazol-4-yl)-1H-indol-3-yl]propyl)-1,2,5,6-tetrahydropyridine 1.85 Hydrogen Oxalate The title compound was synthesised from 3-(5-[1,2,4-triazol-4-yl]-1H-indol-3-yl)propan-1-ol and 4-benzyl-1,2,5,6-tetrahydropyridine using the procedure outlined in Example 16, mp 101° C. (Found: C 61.51, H 5.87, N 12.05. C$_{25}$H$_{27}$N$_5$.1.85 (C$_2$H$_2$O$_4$) requires C, 61.11, H, 5.49, N 12.42%), δ (360 MHz, d$_6$-DMSO) 2.02–2.1 (2H, m, 1 of CH$_2$), 2.16–2.24 (2H, m, 1 of CH$_2$), 2.42–2.5 (2H, m, 1 of CH$_2$), 2.55–2.62 (2H, m, 1 of CH$_2$), 2.77 (2H, t, J=8Hz, 1 of CH$_2$), 3.05–3.15 (2H, m, 1 of CH$_2$), 3.35 (2H, s, 1 of CH$_2$), 5.42–5.46 (1H, m, CH), 7.16–7.35 (7H, m, Ar-H), 7.50 (1H, d, J=9Hz, Ar-H), 7.8 (1H, d, J=2Hz, Ar-H), 9.01 (2H, s, triazole-H), 11.18 (1H, s, indole NH) MS, ES$^+$, m/e for (M+H)$^+$=398.

EXAMPLE 18

1-(3-[5-(1,2,4-Triazol-4-yl)-1H-indol-3-yl]propyl)-4-[2-(4-(aminocarbonylamino)phenyl)ethyl]piperazine Hemihydrate To a solution of 1-(3-[5-(1,2,4-triazol-4-yl)-1H-indol-3-yl]propyl)-4-[2-(4-aminophenyl)ethyl]piperazine (0.25 g, 0.58 mmol) in H$_2$O (2 ml) and glacial acetic acid (10 ml) was added a solution of KCNO (0.096 g, 1.17 mmol) in H$_2$O (0.5 ml) and the mixture stirred at 25° C. for 22 h. The solution was basified with saturated K$_2$CO$_3$ solution and extracted with n-butanol (3×50 ml). The solvent was removed under vacuum and the crude product chromatographed on silica gel eluting with CH$_2$Cl$_2$/MeOH/NH$_3$ (70:8:1) to give the title-product (0.214 g, 78%), mp 214°–216° C. (Found: C, 64.97, H, 6.70, N, 22.90. C$_{26}$H$_{32}$N$_8$O.0.5H$_2$O requires C, 64.85, H, 6.91, N, 23.27%), m/e 473 (M+1)$^+$, δ (250 MHz, d$_6$-DMSO) 1.72–1.90 (2H, m, CH$_2$), 2.28–2.74 (16H, m, 8 of CH$_2$), 5.77 (2H, s, NH$_2$), 7.05 (2H, d, J=8.5Hz, Ar-H), 7.25–7.32 (4H, m, Ar-H), 7.47 (1H, d, J=8.6Hz, Ar-H), 7.79 (1H, d, J=2.1Hz, Ar-H), 8.40 (1H, s, NHCONH$_2$), 9.03 (2H, s, Ar-H), 11.08 (1H, s, NH).

EXAMPLE 19

1-(3-[5-(1,2,4-Triazol-4-yl)-1H-indol-3-yl]propyl)-4-[2-(4-cyanophenyl)ethyl]piperazine 2.5 Hydrogen Oxalate a) 1-(2-(4-Cyanophenyl)ethyl)methane sulphonate Methane sulphonyl chloride (0.856 g, 7.47 mmol) was added to a solution of 2-(4-cyanophenyl)ethanol (1.0 g, 6.80 mmol) and triethylamine (1.03 g, 10.18 mmol), in CH$_2$Cl$_2$ (30 ml), at +5° C. The mixture was warmed to room temperature and stirred for 2 h before adding H$_2$O (15 ml), basifying with solid K$_2$CO$_3$ and extracting with CH$_2$Cl$_2$ (×3). The combined extracts were dried (Na$_2$SO$_4$) and evaporated to afford the title-mesylate (1.52 g, 100%), δ

(360 MHz, $d_6$-DMSO) 3.10 (2H, t, J=6.5Hz, C$\underline{H}_2$-OMs), 3.12 (3H, s, OMs), 4.46 (2H, t, J=6.5Hz, CH$_2$), 7.52 (2H, d, J=8.2Hz, Ar-H), 7.80 (2H, d, J=8.2Hz, Ar-H).

b) 1-(3-[5-(1,2,4-Triazol-4-yl)-1H-indol-3-yl]propyl)-4-[2-(4-cyanophenyl)ethyl]piperazine 2.5 Hydrogen Oxalate A mixture of 1-(3-[5-(1,2,4-triazol-4-yl)-1H-indol-3-yl]propyl)-4(H)-piperazine (Intermediate 2; 0.5 g, 1.61 mmol), sodium carbonate (0.26 g, 2.45 mmol), the preceding mesylate (0.363 g, 1.61 mmol) and NaI (0.242 g, 1.62 mmol), in DME (30 ml), were heated at 85° C. for 16 h. The remaining solid material was removed by filtration and washed with CH$_2$Cl$_2$. The solvent was removed under vacuum and the residue chromatographed on silica gel eluting with CH$_2$Cl$_2$/MeOH/NH$_3$ (70:8:1) to give the title-product (0.20 g, 28%). The 2.5 hydrogen oxalate salt was prepared, mp 212°–215° C. (Found: C, 55.97, H, 5.31, N, 14.42. C$_{26}$H$_{29}$N$_7$ 2.5 (C$_2$H$_2$O$_4$) requires C, 56.02, H, 5.16, N, 14.75%), m/e 440 (M+1)$^+$, δ (360 MHz, $d_6$-DMSO) 1.95–2.08 (2H, m, CH$_2$), 2.64–3.20 (16H, m, 8 of CH$_2$), 7.31–7.34 (2H, m, Ar-H), 7.47 (2H, d, J=8.3Hz, Ar-H), 7.50 (1H, d, J=8.6Hz, Ar-H), 7.76 (2H, d, J=8.3Hz, Ar-H), 7.80 (1H, d, J=2.0Hz, Ar-H), 9.02 (2H, s, Ar-H), 11.16 (1H, s, NH).

EXAMPLE 20

1-(3-[5-(1,2,4-Triazol-4-yl)-1H-indol-3-yl]propyl)-4-[2-(4-(1,2,4-triazol-4-yl)phenyl)ethyl]piperazine 4.0 Hydrogen Oxalate A mixture of 1-(3-[5-(1,2,4-triazol-4-yl)-1H-indol-3-yl]propyl)-4-[2-(4-aminophenyl)ethyl]piperazine (Example 12; 0.25 g, 0.583 mmol), N,N-dimethylformamide azine (84 mg, 0.583 mmol) and p-toluene sulphonic acid monohydrate (0.222 g, 1.17 mmol) in DMF (1.0 ml) was heated at 60° C. for 20 h. The mixture was cooled to room temperature, basified with saturated K$_2$CO$_3$ solution and extracted with n-butanol (2×30 ml). The residue remaining after removal of solvent was chromatographed on silica gel eluting with CH$_2$Cl$_2$/MeOH/NH$_3$ (90:8:1) and the product obtained was rechromatographed on silica gel eluting with diethyl ether/MeOH/NH$_3$ (40:8:1) to give the title-compound (84 mg, 24%). The 4.0 hydrogen oxalate salt was prepared, mp 200°–202° C. (Found: C, 49.94, H, 4.67, N, 14.98. C$_{27}$H$_{31}$N$_9$.4.0(C$_2$H$_2$O$_4$) requires C, 50.09, H, 4.88, N, 15.30%), m/e 482 (M+1)$^+$, δ (360 MHz, $d_6$-DMSO) 1.92–2.06 (2H, m, CH$_2$), 2.68–3.18 (16H, m, 8 of CH$_2$), 7.31–7.33 (2H, m, Ar-H), 7.44 (2H, d, J=8.4Hz, Ar-H), 7.50 (1H, d, J=8.6Hz, Ar-H), 7.62 (2H, d, J=8.4Hz, Ar-H), 7.80 (1H, d, J=1.8Hz, Ar-H), 9.02 (2H, s, Ar-H), 9.09 (2H, s, Ar-H), 11.17 (1H, s, NH).

EXAMPLE 21

1-(3-[5-(1,2,4-Triazol-4-yl)-1H-indol-3-yl]propyl)-4-(4-cyanophenyl)methylpiperazine 1.35 Hydrogen Oxalate 0.25 Hydrate To a mixture of 1-(3-[5-(1,2,4-triazol-4-yl)-1H-indol-3-yl]propyl)-4(H)-piperazine (0.155 g, 0.5 mmol) and K$_2$CO$_3$ (0.138 g, 1.0 mmol) in anhydrous DMF (5 ml) was added 4-cyanobenzyl bromide (0.098 g, 0.5 mmol) and the mixture heated at 50° C. for 0.75 h. The solvent was evaporated and the residue partitioned between ethyl acetate (25 ml) and H$_2$O (20 ml). The organic layer was separated and the aqueous phase extracted with ethyl acetate (2×20 ml). The combined organics were dried (Na$_2$SO$_4$) and evaporated and the residue chromatographed on silica gel eluting with CH$_2$Cl$_2$/MeOH (95:5—>90:10) to give the title 4-(cyano) phenylmethyl piperazine (0.19 g, 89%). The compound was characterised as the 1.35 hydrogen oxalate 0.25 hydrate salt, mp 144° C. (dec.). (Found: C, 60.45, H, 5.89, N, 17.54. C$_{25}$H$_{27}$N$_7$.1.35(C$_2$H$_2$O$_4$).0.25 H$_2$O requires C, 60.32, H, 5.52, N, 17.78%), m/e 426 (M+1)$^+$, δ (360 MHz, $d_6$-DMSO) 1.94–2.06 (2H, m, CH$_2$), 2.42–3.20 (12H, m, 6 of CH$_2$), 3.64 (2H, s, C$\underline{H}_2$Ar), 7.30–7.33 (2H, m, Ar-H), 7.49 (1H, d, J=8.8Hz, Ar-H), 7.52 (2H, d, J=8.5Hz, Ar-H), 7.79 (1H, d, J=2.1Hz, Ar-H), 7.81 (2H, d, J=8.5Hz, Ar-H), 9.01 (2H, s, Ar-H), 11.16 (1H, s, NH).

EXAMPLE 22

1-(3-[5-(1,2,4-Triazol-4-yl)-1H-indol-3-yl]propyl)-4-(2-aminopyridin-5-yl)methylpiperazine 2.3 Hydrogen Oxalate 2.0 Hydrate Triethylamine (175 μL, 1.26 mmol) was added to a suspension of 1-(3-[5-(1,2,4-triazol-4-yl)-1H-indol-3-yl]propyl)-4(H)-piperazine (0.308 g, 0.99 mmol), 6-aminonicotinic acid (0.142 g, 1.03 mmol), 1-hydroxybenzotriazole (0.17 g, 1.26 mmol) and 1-ethyl-3-(3-(dimethylamino)propyl) carbodiimide hydrochloride (0.25 g, 1.30 mmol), in anhydrous DMF (2.5 ml), at room temperature. The mixture was stirred for 24 h and then diluted with water and extracted with $^n$BuOH (×3). The combined extracts were evaporated and the residue chromatographed on silica gel eluting with CH$_2$Cl$_2$/MeOH/NH$_3$ (90:10:1) to give the desired nicotinamide (0.25 g, 59%). Diisobutylaluminium hydride (1.64 ml of a 1.0M solution in CH$_2$Cl$_2$, 1.64 mmol) was added to a stirred suspension of the preceding amide (0.141 g, 0.33 mmol), in anhydrous CH$_2$Cl$_2$ (10 ml), at room temperature. After 1.5 h the reaction was cooled to 0° C. and quenched with 2N HCl (3 ml). The mixture was diluted with water, the CH$_2$Cl$_2$ separated, and the aqueous adjusted to pH 8 with 4N NaOH. The aqueous was extracted with $^n$BuOH (×3) and the combined organics evaporated. The residue was taken up in MeOH and evaporated onto silica gel and chromatographed on silica gel eluting with CH$_2$Cl$_2$/MeOH/NH$_3$ (80:20:1). The resulting product was rechromatographed on silica gel eluting with Et$_2$O/EtOH/H$_2$O/NH$_3$ (60:20:8:1) to give the title-product (44 mg, 32%). The 2.3 hydrogen oxalate 2.0 hydrate salt was prepared, mp 189°–192° C. (Found: C, 50.61, H, 5.41, N, 16.73. C$_{23}$H$_{28}$N$_8$.2.3(C$_2$H$_2$O$_4$).2.0H$_2$O requires C, 50.26, H, 5.59, N, 16.99%), m/e 417 (M+1)$^+$, δ (360 MHz, $d_6$-DMSO) 1.90–2.04 (2H, m, CH$_2$), 2.54–3.18 (12H, m, 6 of CH$_2$), 3.52 (2H, s, CH$_2$), 6.58 (1H, d, J=8.6Hz, Ar-H), 7.30–7.33 (2H, m, Ar-H), 7.46–7.51 (2H, m, Ar-H), 7.79 (1H, s, Ar-H), 7.83 (1H, s, Ar-H), 9.04 (2H, s, Ar-H), 11.60 (1H, s, NH).

EXAMPLE 23

1-(3-[5-(1,2,4-Triazol-1-yl)-1H-indol-3-yl]propyl)-4-benzylpiperazine 2.3 Hydrogen Oxalate a) 1-(3-[5-(1,2,4-Triazol-1-yl)-1H-indol-3-yl]propyl)-4(H)-piperazine Prepared from 5-(4-tert-butyloxycarbonyl)piperazin-1-yl pentanal dimethyl acetal and 4-(1,2,4-triazol-1-yl) phenylhydrazine hydrochloride (WO 94/02477) as described for Intermediate 2, δ (250 MHz, $d_6$-DMSO) 1.74–1.86 (2H, m, CH$_2$), 2.16–2.36 (6H, m, 3 of CH$_2$), 2.58–2.78 (6H, m, 3 of CH$_2$), 4.38 (1H, br s, NH), 7.25 (1H, d, J=2.0Hz, Ar-H), 7.45–7.54 (2H, m, Ar-H), 7.93 (1H, d, J=1.6Hz, Ar-H), 8.18 (1H, s, Ar-H), 9.18 (1H, s, Ar-H), 11.06 (1H, s, NH).

b) 1-(3-[5-(1,2,4-Triazol-1-yl)-1H-indol-3-yl]propyl)-4-benzylpiperazine 2.3 Hydrogen Oxalate Prepared from 1-(3-[5-(1,2,4-triazol-1-yl)-1H-indol-3-yl]propyl)-4(H)-piperazine and benzaldehyde as described for Example 4. The 2.3 hydrogen oxalate salt was prepared, mp 210°–212° C. (Found: C, 56.49, H, 5.40, N, 13.76. $C_{24}H_{28}N_6.2.3(C_2H_2O_4)$ requires C, 56.54, H, 5.41, N, 13.83%), m/e 401 (M+1)$^+$, δ 1.92–2.06 (2H, m, $CH_2$), 2.50–3.06 (12H, m, 6 of $CH_2$), 3.63 (2H, s, C$\underline{H}_2$Ar), 7.24–7.36 (6H, m, Ar-H), 7.48–7.54 (2H, m, Ar-H), 7.94 (1H, s, Ar-H), 8.18 (1H, s, Ar-H), 9.16 (1H, s, Ar-H), 11.16 (1H, s, NH).

EXAMPLE 24

1-(3-[5-(1,2,4-Triazol-1-yl)-1H-indol-3-yl]propyl)-4-[2-(4-(acetylamino)phenyl)ethyl]piperazine 2.5 Hydrogen Oxalate 0.3 Hydrate Prepared from 1-(3-[5-(1,2,4-triazol-1-yl)-1H-indol-3-yl]propyl)-4(H)-piperazine and p-nitrophenethyl bromide using the procedures for Examples 12 and 13. The product was characterised as the 2.5 hydrogen oxalate 0.3 hydrate salt, mp 223°–225° C. (Found: C, 54.63, H, 5.61, N, 14.15. $C_{27}H_{33}N_7O.2.5(C_2H_2O_4).0.3\ H_2O$ requires C, 54.74, H, 5.54, N, 13.97%), m/e 472 (M+1)$^+$, δ (250 MHz, $d_6$-DMSO) 1.92–2.02 (2H, m, $CH_2$), 2.02 (3H, s, Me), 2.68–3.14 (16H, m, 8 of $CH_2$), 7.15 (2H, d, J=8.4Hz, Ar-H), 7.31 (1H, s, Ar-H), 7.47–7.55 (4H, m, Ar-H), 7.95 (1H, s, Ar-H), 8.19 (1H, s, Ar-H), 9.17 (1H, s, Ar-H), 9.87 (1H, s, NH), 11.14 (1H, s, NH).

EXAMPLE 25

1-(3-[5-(1,2,4-Triazol-1-ylmethyl)-1H-indol-3-yl]propyl)-4-benzylpiperazine 2.4 Hydrogen Oxalate 0.1 Diethyl Etherate a) 3-(5-[1,2,4-Triazol-1-ylmethyl]-1H-indol-3-yl]propan-1-ol 3,4-Dihydro-2H-pyran (3.9 ml, 42.7 mmol) was added to a stirred solution of 4-(1,2,4-triazol-1-ylmethyl)phenyl hydrazine (EP 497,512; 4.0 g, 21.1 mmol) in dioxane/water/5N HCl (38 ml/14 ml/4.7 ml) and stirred at room temperature for 1.75 h. The solution was then refluxed for 1.5 h and the solvent removed under vaccum. The residue was taken up into $CH_2Cl_2$ and saturated aqueous $K_2CO_3$ solution. The aqueous was separated and further extracted with $CH_2Cl_2$ (×4). The combined organic extracts were dried ($MgSO_4$) and evaporated and the residue chromatographed on silica gel eluting with $CH_2Cl_2$/MeOH/$NH_3$ (80:8:1) to give the title-indole (0.919 g, 17%), δ (250 MHz, CDCl$_3$) 1.91–2.03 (2H, m, $CH_2$), 2.84 (2H, t, J=7.9Hz, $CH_2$), 3.73 (2H, t, J=7.9Hz, $CH_2$), 5.43 (2H, s, $CH_2$), 7.04 (1H, d, J=2.3Hz, Ar-H), 7.11 (1H, dd, J=2.3 and 8.3Hz, Ar-H), 7.35 (1H, d, J=8.3Hz, Ar-H), 7.58 (1H, s, Ar-H), 7.97 (1H, s, Ar-H), 8.02 (1H, s, Ar-H), 8.18 (1H, s, NH).

b) 1-(3-[5-(1,2,4-Triazol-1-ylmethyl)-1H-indol-3-yl]propyl)-4-benzylpiperazine 2.4 Hydrogen Oxalate 0.1 Diethyl etherate Methanesulphonyl chloride (0.35 ml, 4.52 mmol) was added dropwise to a stirred solution of triethylamine (0.682 ml, 4.89 mmol) and the preceding propyl alcohol (0.965 g, 3.77 mmol), in anhydrous THF (15 ml), at −35° C. The mixture was warmed to room temperature and stirred for 16 h. The solvent was removed under vacuum and the residue taken up into $CH_2Cl_2$ (50 ml) and washed with $H_2O$ (×2). The $CH_2Cl_2$ was dried ($MgSO_4$) and evaporated and the residue rapidly flash chromatographed on silica gel eluting with $CH_2Cl_2$/MeOH (94:6) to give the desired mesylate (0.775 g, 62%). $K_2CO_3$ (0.901 g, 6.5 mmol) and N-benzylpiperazine (0.94 ml, 5.4 mmol) were added successively to a stirred solution of the mesylate (0.727 g, 2.17 mmol) in IPA (100 ml). The mixture was refluxed for 4 h, cooled to room temperature, and the solvent removed under vacuum. The residue was taken up into $CH_2Cl_2$/$H_2O$ and the aqueous layer separated and further extracted with $CH_2Cl_2$ (×2). The combined extracts were dried ($MgSO_4$) and evaporated and the resulting residue was chromatographed on silica gel eluting with $CH_2Cl_2$/MeOH/$NH_3$ (90:10:1) to give the title-benzylpiperazine (616 mg, 68%). The 2.4 hydrogen oxalate 0.1 diethyl etherate salt was prepared, mp 204°–206° C. (Found: C, 56.83, H, 5.81, N, 13.14. $C_{25}H_{30}N_6.2.4(C_2H_2O_4).0.1(Et_2O)$ requires C, 56.85, H, 5.66, N, 13.17%), m/e 415 (M+1)$^+$, δ (360 MHz, $d_6$-DMSO) 1.92–2.04 (2H, m, $CH_2$), 2.50–3.30 (12H, m, 6 of $CH_2$), 3.64 (2H, s, $CH_2$), 5.43 (2H, s, $CH_2$), 7.05 (1H, d, J=8.4Hz, Ar-H), 7.19 (1H, s, Ar-H), 7.26–7.36 (6H, m, Ar-H), 7.51 (1H, s, Ar-H), 7.93 (1H, s, Ar-H), 8.60 (1H, s, Ar-H), 10.91 (1H, s, NH).

EXAMPLE 26

1-(3-[5-(1,2,4-Triazol-1-ylmethyl)-1H-indol-3-yl]propyl)-4-[2-(4-(acetylamino)phenyl)ethyl]piperazine 2.5 Hydrogen Oxalate 0.2 Diethyl Etherate a) 1-(3-[5-(1,2,4-Triazol-1-ylmethyl)-1H-indol-3-yl]propyl)-4(H)-piperazine A mixture of 1-(3-[5-(1,2,4-triazol-1-ylmethyl)-1H-indol-3-yl]propyl)-4-benzylpiperazine (0.53 g, 1.28 mmol), ammonium formate (0.403 g, 6.39 mmol), 10% Pd-C (0.53 g) and MeOH (35 ml) was heated at 66° C. for 0.75 h. The catalyst was removed by filtering the reaction mixture through celite and washing with EtOH. The combined filtrate and washings were evaporated and the residue chromatographed on silica gel eluting with $CH_2Cl_2$/MeOH/$NH_3$ (40:8:1) to give the title-N(H) piperazine (0.344 g, 83%), δ (250 MHz, CDCl$_3$) 1.84–1.96 (2H, m, $CH_2$), 2.38–2.46 (6H, m, 3 of $CH_2$), 2.76 (2H, t, J=7.5Hz, $CH_2$), 2.90–2.94 (4H, m, 2 of $CH_2$), 5.43 (2H, s, $CH_2$), 7.03 (1H, s, Ar-H), 7.11 (1H, dd, J=1.7 and 8.2Hz, Ar-H), 7.35 (1H, d, J=8.2Hz, Ar-H), 7.57 (1H, s, Ar-H), 7.96 (1H, s, Ar-H), 7.99 (1H, s, Ar-H), 8.22 (1H, br s, NH).

b) 1-(3-[5-(1,2,4-Triazol-1-ylmethyl)-1H-indol-3-yl]propyl)-4-[2-(4-(acetylamino)phenyl)ethyl]piperazine 2.5 Hydrogen Oxalate 0.2 Diethyl Etherate Prepared from 1-(3-[5-(1,2,4-triazol-1-ylmethyl)-1H-indol-3-yl]propyl)-4(H)-piperazine and p-nitrophenethyl bromide using the procedures described for Examples 12 and 13. The product was characterised as the 2.5 hydrogen oxalate 0.2 diethyl etherate salt, mp 208°–210° C. (Found: C, 56.08, H, 6.08, N, 13.23. $C_{28}H_{35}N_7O.2.5(C_2H_2O_4).0.2(Et_2O)$ requires C, 55.95, H, 5.84, N, 13.51%), m/e 486 (M+1)$^+$, δ (360 MHz, $d_6$-DMSO) 1.88–2.00 (2H, m, $CH_2$), 2.02 (3H, s, Me), 2.66–3.12 (16H, m, 8 of $CH_2$), 5.44 (2H, s, $CH_2$), 7.05 (1H, d, J=8.3Hz, Ar-H), 7.15 (2H, d, J=8.5Hz, Ar-H), 7.18 (1H, s, Ar-H), 7.32 (1H, d, J=8.3Hz, Ar-H), 7.49 (2H, d, J=8.5Hz, Ar-H), 7.52 (1H, s, Ar-H), 7.95 (1H, s, Ar-H), 8.60 (1H, s, Ar-H), 9.87 (1H, s, NH), 10.90 (1H, s, NH).

EXAMPLE 27

1-(3-[5-(1,2,4-Triazol-4-yl)-1H-indol-3-yl]propyl)-4-[2-(3-(acetylamino)phenyl)ethyl]piperazine. 6.0 Hydrogen Oxalate. 1.5 Hydrate Prepared from 1-(2-(3-(acetylamino)phenyl)ethyl) methane sulphonate and 1-(3-[5-(1,2,4-triazol-4-yl)-1H- indol-3-yl]propyl)-4(H)-piperazine using the procedure described for Example 19. The compound was characterised as the 6.0 hydrogen oxalate 1.5 hydrate salt (hygroscopic). (Found: C, 45.08, H, 4.91, N, 9.64. $C_{27}H_{33}N_7O$. 6.0 $(C_2H_2O_4).1.5H_2O$ requires C, 45.09, H, 4.65, N, 9.43%), m/e 472 $(M+1)^+$, δ (360 MHz, $d_6$-DMSO) 1.90–2.08 (2H, m, $CH_2$), 2.02 (3H, s, Me), 2.72–3.16 (16H, m, 8 of $CH_2$), 6.91 (1H, d, J=7.4Hz, Ar-H), 7.18–7.23 (1H, m, Ar-H), 7.31–7.36 (3H, m, Ar-H), 7.50 (1H, d, J=8.7Hz, Ar-H), 7.51 (1H, s, Ar-H), 7.80 (1H, d, J=1.9Hz, Ar-H), 9.02 (2H, s, Ar-H), 9.89 (1H, s, NH), 11.16 (1H, s, NH).

EXAMPLE 28

1-(3-[5-(1,2,4-Triazol-4-yl)-1H-indol-3-yl]propyl)-4-[4-(aminosulphonylphenyl)methyl]piperazine. 1.5 Hydrate. 0.2 Methanol The title compound was prepared from 1-(4-(aminosulphonyl)phenyl)methyl methane sulphonate and 1-(3-[5-(1,2,4-triazol-4-yl)-1H-indol-3-yl]propyl)-4(H)-piperazine using the procedure described for Example 19. The compound was characterised as the 1.5 hydrate which crystallised with 0.2 methanol, mp 166° C., (Found: C, 56.85, H, 6.10, N, 18.71. $C_{24}H_{29}N_7O_2S.1.5H_2O..0.2$ (MeOH) requires C, 56.66, H, 6.44, N, 19.11%), m/e 480 $(M+1)^+$.

EXAMPLE 29

1-(3-[5-(1,2,4-Triazol-4-yl)-1H-indol-3-yl]propyl)-4-(furan-3-ylmethyl)piperazine. 2.25 Hydrogen Oxalate. 1.6 Diethyl Etherate Prepared from 1-(3-[5-(1,2,4-triazol-4-yl)-1H-indol-3-yl]propyl)-4(H)-piperazine and 3-furfuraldehyde using the general reductive amination procedure. The 2.25 hydrogen oxalate salt was prepared which crystallised with diethyl ether, mp 208°–210° C., (Found: C, 55.85, H, 6.16, N, 11.46. $C_{22}H_{26}N_6O.2.25(C_2H_2O_4).1.6(Et_2O)$ requires C, 55.53, H, 6.48, N, 11.80%), m/e 391 $(M+1)^+$, δ (250 MHz, $d_6$-DMSO) 1.92–2.08 (2H, m, $CH_2$), 2.58–3.24 (12H, m, 6 of $CH_2$), 3.54 (2H, s, $CH_2$), 6.46 (1H, s, Ar-H), 7.30–7.34 (2H, m, Ar-H), 7.50 (1H, d, J=8.6Hz, Ar-H), 7.64–7.68 (2H, m, Ar-H), 7.80 (1H, d, J=2.0Hz, Ar-H), 9.03 (2H, s, Ar-H), 11.20 (1H, s, NH).

EXAMPLE 30

1-(3-[5-(1,2,4-Triazol-4-yl)-1H-indol-3-yl]propyl)-4-(furan-2-ylmethyl)piperazine. 1.35 Hydrogen Oxalate Prepared from 1-(3-[5-(1,2,4-triazol-4-yl)-1H-indol-3-yl]propyl)-4(H)-piperazine and 2-furfuraldehyde as described for Example 1, mp 197°–200° C. (Found: C, 57.85, H, 5.81, N, 16.51. $C_{22}H_{26}N_6O. 1.35(C_2H_2O_4)$ requires C, 57.93, H, 5.64, N, 16.41%), m/e 391 $(M+1)^+$, δ (360 MHz, $d_6$-DMSO) 1.92–2.06 (2H, m, $CH_2$), 2.52–3.20 (12H, m, 6 of $CH_2$), 3.60 (2H, s, $CH_2$), 6.33 (1H, d, J=3.0Hz, Ar-H), 6.41–6.42 (1H, m, Ar-H), 7.30–7.33 (2H, m, Ar-H), 7.49 (1H, d, J=8.9Hz, Ar-H), 7.61 (1H, s, Ar-H), 7.79 (1H, d, J=2.0Hz, Ar-H), 9.01 (2H, s, Ar-H), 11.16 (1H, s, NH).

EXAMPLE 31

1-(3-[5-(1,2,4-Triazol-4-yl)-1H-indol-3-yl]propyl)-4-(thiophen-2-ylmethyl)piperazine. 3.25 Hydrogen Oxalate Prepared from 1-(3-[5-(1,2,4-triazol-4-yl)-1H-indol-3-yl] propyl)-4(H)-piperazine and thiophene-2-carboxaldehyde using the general reductive amination procedure, mp 213°–215° C. (Found: C, 48.90, H, 4.80, N, 12.01. $C_{22}H_{26}N_6S.3.25(C_2H_2O_4)$ requires C, 48.96, H, 4.69, N, 12.02%), m/e 407 $(M+1)^+$.

EXAMPLE 32

1-Benzyl-4-{(R,S)-2-hydroxy-3-[5-(1,2,4-triazol-4-yl)-1H-indol-3-yl]propyl}piperazine. 2.4 Hydrogen Oxalate a) Ethyl (R,S)-4,5-epoxypentanoate To a cooled (–5°) and stirred solution of ethyl pent-4-enoate (10 g, 78 mmol) in dichloromethane (200 ml) was added dropwise a solution of m-chloroperoxybenzoic acid (50–55%; 29.5 g) in dichloromethane (250 ml), over 30 minutes. The mixture was allowed to warm to room temperature overnight before it was diluted with diethyl ether (700 ml) and washed with 2N aqueous sodium hydroxide (150 ml), 10% sodium thiosulphate—10% sodium iodide—2N sodium hydroxide mixture (1:1:1, 2×80 ml) and brine (2×100 ml), then dried ($MgSO_4$) and concentrated. Flash chromatography (silica gel, dichloromethane to dichloromethane—diethyl ether, 1:1) of the residue afforded 10 g (89%) of the title compound as a colourless liquid. δ (360 MHz, $CDCl_3$) 1.27 (3H, t, J=7.1Hz), 1.79 (1H, q, J=7.0Hz), 1.97 (1H, m), 2.46 (2H, t, J=7.2Hz), 2.51 (1H, m), 2.77 (1H, m), 2.99 (1H, m), 4.15 (2H, q, J=7.1Hz).

b) (R,S)-5-[(4-Benzylpiperazin-1-yl)methyl]butyrolactone

A solution of the preceding epoxide (3.0 g, 20.8 mmol) and 4-benzylpiperazine (7.3 g, 40.6 mmol) in absolute ethanol (40 ml) was refluxed, under nitrogen, for 5 hours. The solvent was removed under vacuum and the residue purified by flash chromatography (silica gel, dichloromethane-methanol, 95:5; and silica gel, diethyl ether-ethanol, 90:10 to diethyl ether-methanol, 90:10) to give 2.74 g of the title compound as a thick pale yellow oil. δ (360 MHz, $CDCl_3$) 1.80–1.94 (1H, m), 2.16–2.28 (1H, m), 2.34–2.60 (12H, m), 3.40–3.44 (2H, m), 4.52–4.62 (1H, m), 7.14–7.28 (5H, m); m/e (ES) 275 $(M+1)^+$.

c) 1-Benzyl-4-{(R,S)-2-hydroxy-3-[5-(1,2,4-triazol-4-yl)-1H-indol-3-yl]propyl}piperazine. 2.4 Oxalate To a cooled (–81° C.) and stirred solution of the above lactone (2.7 g, 9.7 mmol) in anhydrous toluene (100 ml) was added dropwise, under nitrogen, diisobutylaluminium hydride (1M in toluene; 15.5 ml) over 35 minutes. After being stirred at –80° C. for 2 hours 15 minutes, the reaction was quenched by dropwise addition of methanol (7.8 ml) followed by aqueous potassium sodium tartrate (20%, 100 ml). Products were extracted with diethyl ether (2×200 ml), washed with brine (1×50 ml), dried ($MgSO_4$) and concentrated. Flash chromatography (silica gel, dichloromethane-methanol, 90:10 to 85:15) gave 2.04 g (75.5%) of the intermediate lactol as a colourless oil.

A solution of the above lactol (1.84 g, 6.8 mmol) and 4'-(1,2,4-triazol-4-yl)phenylhydrazine (1.33 g, 7.5 mmol) in 4% sulphuric acid (80 ml) was stirred at room temperature for 20 minutes and then refluxed for 30 hours. After cooling, the mixture was basified with 30% aqueous sodium hydroxide, diluted with ethyl acetate (150 ml) and the two-phase mixture was vigorously stirred for 2 hours. The organic phase was decanted off and the aqueous layer extracted with ethyl acetate (2×200 ml). The combined organic solutions were washed with brine (1×50 ml), dried ($MgSO_4$) and concentrated. Flash chromatography (silica gel, dichloromethane-methanol-ammonia, 92:8:0.8) of the mixture afforded 1.94 g (61.5%) of the title compound free base. The oxalate salt was prepared and recrystallised from ethanol-water, mp. 193°–196° C. (Found: C, 54.70; H, 5.29;

N, 13.40. $C_{24}H_{28}N_6O \times 2.4\ C_2H_2O_4$ requires C, 54.68; H, 5.23; N,13.29%). δ (360 MHz, DMSO-$d_6$) 2.54–2.76 (4H, m), 2.82–3.24 (8H, m), 3.62 (2H, s), 4.14–4.24 (1H, m), 7.25–7.38 (7H, m), 7.50 (1H, d, J=8.5Hz), 7.81 (1H, d, J=2.0Hz), 8.99 (2H, s), 11.23 (1H, s); m/e (ES) 417 (M+H).

EXAMPLE 33

1-[4-(Acetylamino)phenethyl]-4-{(R,S)-2-hydroxy-3-[5-(1,2,4-triazol-4-yl)-1H-indol-3-yl]propyl}piperazine. 2.25 Hydrogen Oxalate a) 4-(Acetylamino)phenethyl bromide A solution of 4-nitrophenethyl bromide (23.8 g, 103.6 mmol) and acetic anhydride (9.8 ml, 103.6 mmol) in absolute ethanol (400 ml) was hydrogenated over platinum (IV) oxide (2.38 g) at 10 psi. The catalyst was removed by filtration and the solvent evaporated under vacuum. The remaining residue was purified by flash chromatography (silica gel, dichloromethane) to give 12.34 g of the title compound as a white solid. δ (250 MHz, CDCl$_3$) 2.16 (3H, s), 3.12 (2H, t, J=7.5Hz), 3.53 (2H, t, J=7.5Hz), 7.15 (2H, d, J=8.4Hz), 7.45 (2H, d, J=8.4Hz).

b) 1-[4-(Acetylamino)phenethyl]-4-{(R,S)-2-hydroxy-3-[5-(1,2,4-triazol-4-yl)-1H-indol-3-yl]propyl}piperazine. 2.25 Hydrogen Oxalate A solution of the product from Example 22 (free base; 1.25 g) in absolute ethanol (60 ml) was hydrogenated at 48 psi over Pearlman's catalyst (1 g) for 18 hours. The catalyst was filtered off, washed with absolute ethanol (3×35 ml) and with ethanol-ammonia (30:1; 2×35 ml), and the filtrate was concentrated under vacuum. The residue was purified by flash chromatography (silica gel, dichloromethane-methanol-ammonia, 70:30:2) to give 4-{(R,S)-2-hydroxy-3-[5-(1,2,4-triazol-4-yl)-1H-indol-3-yl]propyl}piperazine (788 mg, 80%) as a white foam.

A mixture of the above piperazine (270 mg, 0.83 mmol), 4-(acetylamino)phenethyl bromide (198 mg, 0.87 mmol) and anhydrous potassium carbonate (114 mg, 0.83 mmol) in anhydrous dimethylformamide (9 ml) was heated at 80° C. for 22 hours, under nitrogen. After cooling, water (30 ml) and saturated aqueous potassium carbonate (2 ml) were added, and products were extracted with ethyl acetate (3×75 ml) and with ethyl acetate—butanol (1:1, 1×125 ml). The combined organic solutions were concentrated under vacuum and the remaining residue was purified by flash chromatography (silica gel, dichloromethane-methanol-ammonia, 92:8:0.8) to give 221 mg (55%) of the title compound free base as a colourless glass. The oxalate salt was prepared from ethanol, mp 210°–212° C. (Found: C, 54.55; H, 5.53; N, 14.34. $C_{27}H_{33}N_7O_2 \times 2.25\ C_2H_2O_4$ requires: C, 54.82; H, 5.48; N, 14.21%). δ (360 MHz, DMSO-$d_6$) 2.01 (3H, s), 2.68–3.16 (16H, m), 4.08–4.18 (1H, m), 7.14 (2H, d, J=8.5Hz), 7.28–7.36 (2H, m), 7.44–7.54 (3H, m), 7.81 (1H, d, J=2.0Hz), 9.00 (2H, s), 9.86 (1H,s), 11.20 (1H, s); m/e (ES) 488 (M+1)$^+$.

EXAMPLE 34

1-Benzyl-4-{(R,S)-2-(hydroxymethyl)-3-[5-(1,2,4-triazol-4-yl)-1H-indol-3-yl]propyl}piperazine 2.25 Hydrogen Oxalate a) 4-Benzyl-1-[(ethoxycarbonyl)acetyl]piperazine To a cooled (−20° C.) and stirred solution of N-benzylpiperazine (10 g, 56.7 mmol) and triethylamine (8.7 ml, 62.4 mmol) in dichloromethane (200 ml) was added ethyl malonyl chloride (8.5 ml, 66.4 mmol) over 10 minutes, under nitrogen. The mixture was allowed to warm to room temperature and it was stirred for 1 hour before water (100 ml) and diethyl ether (500 ml) were added. The organic phase was decanted off, washed with water (1×70 ml), 10% aqueous sodium bicarbonate (1×75 ml), brine (1×75 ml), then dried (MgSO$_4$) and concentrated. Flash chromatography of the residue (silica gel, ethyl acetate—ethanol, 95:5) afforded 9.53 g, (58%) of the title compound as a colourless oil. δ (360 MHz, CDCl$_3$), 1.28 (3H, t, J=7.2Hz), 2.48 (4H, br s), 3.45 (2H, s) 3.47 (2H, br s), 3.56 (2H, br s), 3.68 (2H, br s), 4.19 (2H, q, J=7.2Hz), 7.24–7.36 (5H, m); m/e (ES) 291 (M+1)$^+$.

b) 4-Benzyl-1-[4-(1,3-dioxolan-2-yl)-2-(ethoxycarbonyl)-butyryl]piperazine

To a stirred suspension of sodium hydride (60% dispersion in oil, 1.4 g) in anhydrous dimethylformamide (50 ml) was added dropwise, under nitrogen, a solution of 4-benzyl-1-[(ethoxycarbonyl)acetyl]-piperazine (8.5 g, 29.3 mmol) in anhydrous dimethylformamide (50 ml) over 25 minutes at room temperature. After a further 30 minutes at room temperature, 2-(2-bromoethyl)-1,3-dioxolane (3.6 ml, 30.7 mmol) was added dropwise over 3 minutes and the resulting yellow solution was stirred for 24 hours. Water (400 ml) was added and products were extracted with diethyl ether (3×300 ml). The combined ethereal phases were washed with brine (1×150 ml), dried (MgSO$_4$) and concentrated. Flash chromatography of the residue (silica gel, diethyl ether—ethanol, 95:5) afforded 8 g of the title compound (70%) as a colourless oil, δ (360 MHz, CDCl$_3$), 1.25 (3H, t, J=7.1Hz), 1.56–1.78 (2H, m), 2.06 (2H, q, J=7.4Hz), 2.44 (4H, br s), 3.46–3.96 (11H, m), 4.16 (2H, q, J=7.1Hz), 4.86 (1H, t, J=4.6Hz), 7.24–7.36 (5H, m); m/e (ES) 391 (M+1)$^+$.

c) 4-Benzyl-1-[4-(1,3-dioxolan-2-yl)-2-(hydroxymethyl)-butyl]piperazine

To a cooled (−30° C.) and stirred solution of lithium aluminium hydride (1M in THF; 16.4 ml) in anhydrous tetrahydrofuran (30 ml) was added dropwise, via cannula, a solution of the product from the preceding step (3.2 g, 8.19 mmol) in anhydrous tetrahydrofuran (30 ml) over 14 minutes, under a nitrogen atmosphere. The resulting clear colourless solution was allowed to warm to room temperature and it was stirred for 4 hours before excess lithium aluminium hydride was destroyed by careful addition of tetrahydrofuran-water (80:20; 25 ml) (CAUTION! hydrogen evolution). The precipitated aluminium salts were filtered off, washed with tetrahydrofuran—water (80:20; 2×70 ml) and the filtrate was concentrated under vacuum. Flash chromatography of the residue (silica gel, diethyl ether-methanol, 92:8; and silica gel, dichloromethane-methanol, 93:7) afforded 1.96 g (71.5%) of the title compound as a colourless oil. δ (360 MHz, CDCl$_3$) 1.14–1.24 (2H, m), 1.62–1.72 (2H, m), 1.92–2.06 (1H, m), 2.20–2.90 (10H, m), 3.42–3.56 (3H, m), 3.72–4.00 (5H, m), 4.81 (1H, t, J=4.6Hz), 7.20–7.36 (5H, m); m/e (ES) 335 (M+1)$^+$.

d) 1-Benzyl-4-{(R,S)-2-(hydroxymethyl)-3-[5-(1,2,4-triazol-4-yl)-1H-indol-3-yl]propyl}piperazine. 2.25 Hydrogen Oxalate The title compound was prepared from the product of the preceding step and 4'-(1,2,4-triazol-4-yl)phenylhydrazine using a similar method to that described for Example 32 (step 3). The oxalate salt was prepared from absolute ethanol, mp 188°–191° C. (Found: C, 55.94; H, 5.69; N, 13.28. $C_{25}H_{30}N_6O \times 2.25\ C_2H_2O_4$ requires: C, 55.96; H, 5.49; N, 13.27%). δ (360 MHz, DMSO-$d_6$) 2.14–2.24 (1H, m), 2.64–3.10 (12H, m), 3.39 (1H, dd, J=10.6 and 6.0Hz), 3.45 (1H, dd, J=10.6 and 4.3Hz), 3.77 (2H, m), 7.26–7.42 (7H, m), 7.49 (1H, d, J=8.6Hz), 7.78 (1H, d, 1.9Hz), 8.99 (2H, s), 11.17 (1H, s); m/e (ES) 431 (M+1)$^+$.

EXAMPLE 35

1-(3-[5-(1,2,4-Triazol-4-yl)-1H-indol-3-yl]propyl)-4-(2-(1-(H)-tetrazol-5-yl)phenyl)methylpiperazine 2.5 Hydrogen Oxalate To a solution of Intermediate 2 (0.155 g, 0.5 mmol) in anhydrous DMF (5 ml) was added K$_2$CO$_3$ (0.138 g, 1.0 mmol) and α-bromo-o-tolunitrile (98 mg, 0.5 mmol) and the mixture was heated at 50° C. for 1 h. The solvent was evaporated and the residue partitioned between ethyl acetate (25 ml) and water (25 ml). The organic layer was separated and the aqueous phase extracted with ethyl acetate (2×20 ml). The combined organics were dried ($Na_2SO_4$) and evaporated and the residue chromatographed on silica gel, eluting with $CH_2Cl_2$/MeOH (95:5—>90:10) to give the desired o-cyanobenzyl piperazine (0.159 g, 75%). To a solution of the preceding nitrile (0.156 g, 0.36 mmol), in N-methyl-2-pyrrolidinone (5 ml) was added triethylamine hydrochloride (75 mg, 0.55 mmol) and sodium azide (71 mg, 1.1 mmol) and the mixture heated at 160° C. for 6 h. After this time, further $NaN_3$ (36 mg, 0.55 mmol) and triethylamine hydrochloride (38 mg, 0.28 mmol) were added, and the mixture heated at 160° C. for 10 h. The solvent was evaporated and the residue chromatographed on silica gel eluting with $Et_2O$/EtOH/$H_2O$ (20:20:5) to give the title-tetrazole (56 mg, 14%). The 2.5 hydrogen oxalate salt was prepared, mp 150° C. (dec.), (Found: C, 51.64, H, 4.99, N, 19.85. $C_{25}H_{28}N_{10}$. 2.5($C_2H_2O_4$) requires C, 51.95, H, 4.80, N, 20.19%), m/e 469 (M+1)$^+$, δ (360 MHz, $d_6$-DMSO) 1.85–2.00 (2H, m, $CH_2$), 2.66–2.96 (12H, m, 6 of $CH_2$), 4.09 (2H, s, $CH_2$), 7.26–7.34 (2H, m, Ar-H), 7.46–7.58 (4H, m, Ar-H), 7.78 (1H, s, Ar-H), 7.93 (1H, d, J=7.05Hz, Ar-H), 9.01 (2H, s, Ar-H), 11.12 (1H, s, NH).

EXAMPLE 36

1-(3-[5-(1,2,4-Triazol-4-yl)-1H-indol-3-yl]propyl)-4-(phenethyl)piperazine. 2.4 Hydrogen Oxalate 0.4 Diethyl Etherate Prepared from Intermediate 2 and phenylacetaldehyde using the general reductive amination procedure; mp. 193°–195° C. (Found: C, 57.46, H, 6.14; N, 12.97. $C_{25}H_{30}N_6$.2.4($C_2H_2O_4$). 0.4($Et_2O$) requires C, 57.12; H, 5.92; N, 12.73%); m/e 415 (M+1)$^+$; δ (360 MHz, $d_6$-DMSO) 1.92–2.04 (2H, m, $CH_2$), 2.68–3.10 (16H, m, 8 of $CH_2$), 7.19–7.34 (7H, m, Ar-H), 7.50 (1H, d, J=8.6Hz, Ar-H), 7.80 (1H, d, J=1.9Hz, Ar-H), 9.02 (2H, s, Ar-H), 11.17 (1H, s, NH).

EXAMPLE 37

4-Benzyl-1-(3-[5-(1,2,4-triazol-4-yl)-1H-indol-3-yl]propyl)piperidine Hydrogen Oxalate A stirred suspension of 3-(5-[1,2,4-triazol-4-yl]-1H-indol-3-yl)-propan-1-ol (300 mg, 1.24 mmol) in anhydrous tetrahydrofuran (30 ml) was treated with methanesulphonyl chloride (192 μl, 2.48 mmol) and triethyamine (346 μl, 2.48 mmol). The reaction mixture was stirred at room temperature for 1.5 hours, filtered, then evaporated. The residue was partitioned between water (50 ml) and dichloromethane (50 ml). The aqueous was extracted with dichloromethane (50 ml) then the combined organics were washed with water (50 ml), dried (sodium sulphate) and evaporated to give the crude mesylate. This mesylate was dissolved in propan-2-ol (70 ml), treated with potassium carbonate (515 mg, 3.72 mmol) and 4-benzylpiperidine (654 μl, 3.72 mmol) then stirred whilst heating at reflux for 18 hours. The reaction mixture was evaporated, then the residue partitioned between water (30 ml) and dichloromethane (50 ml). The organic layer was separated and the aqueous was extracted with dichloromethane (2×50 ml). The combined organics were dried (sodium sulphate) then evaporated to dryness. The crude product was purified by column chromatography on silica using dichloromethane/methanol/ammonia (95:5:0.5) to give the required product free base as a gum (130 mg, 26%). The hydrogen oxalate salt had mp 115°–117° C. (Found: C, 60.76; H, 6.15; N, 12.77. $C_{25}H_{29}N_5$.1.85$C_2H_2O_4$ requires C, 60.89; H, 5.82; N, 12.37%); δ (360 MHz, $d_6$-DMSO) 1.30–1.50 (2H, m), 1.65–1.80 (3H, m), 1.98–2.10 (2H, m), 2.48–2.52 (2H, m), 2.75–2.90 (4H, m), 3.00–3.10 (2H, m), 3.35–3.50 (2H, m), 7.16–7.22 (3H, m, Ar-H), 7.27–7.33 (4H, m, Ar-H), 7.50 (1H, d, J=8Hz, Ar-H), 7.80 (1H, s, Ar-H), 9.01 (2H, s, triazole-H), 11.19 (1H, s, indole-H). MS, ES$^+$, m/z for (M+H)$^+$=400.

EXAMPLES 38 AND 39

4-([2-(1-Methyltetrazol-5-yl)phenyl]methyl)-1-(3-[5-(1,2,4-triazol-4-yl)-1H-indol-3-yl]propyl)piperazine. Hydrogen Oxalate and 4-([2-(2-Methyltetrazol-5-yl)phenyl]methyl)-1-(3-[5-(1,2,4-triazol-4-yl)-1H-indol-3-yl]propyl)piperazine. 1.45 Hydrogen Oxalate To a solution of 1-(3-[5-(1,2,4-triazol-4-yl)-1H-indol-3-yl]propyl)-4-(2-(1-(H)-tetrazol-5-yl)phenyl)methylpiperazine [Example 35] (238 mg, 0.51 mmol) in anhydrous DMF (10 ml) was added triethylamine (0.21 ml, 1.53 mmol) and methyl iodide (95 μl, 1.53 mmol). The mixture was stirred at room temperature for 20 h before more triethylamine (71 μl, 0.51 mmol) and methyl iodide (32 μl, 0.57 mmol) were added. The mixture was stirred for a further 6 h, then the solvent was evaporated. The residue was chromatographed on silica gel, eluting with $CH_2Cl_2$/MeOH (90:10→80:20) to afford a mixture of the methylated tetrazoles containing a small quantity of impurity. This mixture was re-chromatographed on silica gel, eluting with $CH_2Cl_2$/MeOH/$NH_3$ (90:10:1) to give a 2:1 mixture of the 2-methyl:1-methyl tetrazoles (76 mg, 31%) as a brown foam.

The mixture was dissolved (5 mg/ml) in 20% $CH_3CN$ in 0.1% aqueous TFA. 1 ml of solution was injected onto a KR100C18 column (250×20 mm i.d., 5 μM) per run, using 20% $CH_3CN$ in 0.1% aqueous TFA as the mobile phase. Using a flow rate of 20 ml/min. and U.V. detection at 230 nM, the two isomers were efficiently separated. The fractions containing each separate isomer were combined and evaporated in vacuo.

Isomer A (74 mg): Retention time 6.6 min.

Isomer B (40 mg): Retention time 7.9 min.

The TFA salt of each isomer was partitioned between $CH_2Cl_2$ (25 ml) and $Na_2CO_3$ solution (10%, 15 ml). The organic phase was separated, dried ($Na_2SO_4$) and evaporated. The residue was then chromatographed on silica gel, eluting with $CH_2Cl_2$/MeOH/$NH_3$ (90:10:1), to afford the 2-methyl isomer (Isomer A) (44 mg) as a pale yellow foam and the 1-methyl isomer (Isomer B) (22 mg) as a pale yellow foam.

The 1.45 hydrogen oxalate salt of the 2-methyl tetrazole was prepared, purity>99.7%, mp 105° C. (dec.), (Found: C, 56.63, H, 5.74, N, 22.91%. $C_{26}H_{30}N_{10}$.1.45 ($C_2H_2O_4$) requires C, 56.61, H, 5.41, N, 22.84%), m/e 483 (M+1)$^+$, δ (360 MHz, $d_6$-DMSO) 1.92–2.03 (2H, m), 2.42–3.07 (12H, m), 3.93 (2H, s), 4.44 (3H, s), 7.31–7.33 (2H, m), 7.43–7.55 (3H, m), 7.61 (1H, d, J=7.4Hz), 7.83 (1H, s), 7.87 (1H, d, J=7.5Hz), 9.01 (2H, s), 11.16 (1H, br s).

The hydrogen oxalate salt of the 1-methyl tetrazole was prepared, purity 96%, mp 128° C.(dec.), (Found: C, 59.89, H, 6.09, N, 23.53%. $C_{26}H_{30}N_{10}$.$C_2H_2O_4$ 0.2($Et_2O$) requires C, 58.88, H, 5.83, N, 23.84%), m/e 483 (M+1)$^+$, δ (360

MHz, d$_6$-DMSO) 1.90–2.03 (2H, m), 2.24–2.40 (4H, m), 2.68–2.82 (4H, m), 2.86–3.02 (4H, m), 3.49 (2H, s), 3.91 (3H, s), 7.31–7.33 (2H, m), 7.48–7.62 (5H, m), 7.79 (1H, d, J=1.9Hz), 9.01 (2H, s), 11.16 (1H, br s).

EXAMPLE 40

4-([2-N-Methylcarboxamidophenyl]methyl)-1-(3-[5-(1,2,4-triazol-4-yl)-1H-indol-3-yl]propyl)piperazine. 1.5 Hydrogen Oxalate a) 4-([2-Carbomethoxyphenyl]methyl)-1-(3-[5-(1,2,4-triazol-4-yl)-1H-indol-3-yl]propyl)piperazine To a solution of Intermediate 2 (100 mg, 0.32 mmol) in anhydrous DMF (5 ml) was added K$_2$CO$_3$ (49 mg, 0.35 mmol) and methyl 2-(bromomethyl)benzoate (81 mg, 0.35 mmol) and the mixture heated at 70° C. for 2 h. The solvent was evaporated and the residue azeotroped with toluene (2×10 ml). The residue was chromatographed on silica gel, eluting with CH$_2$Cl$_2$/MeOH (90:10) to give the desired ester (106 mg, 72%) as a pale yellow foam. δ (250 MHz, CDCl$_3$) 1.84–1.96 (2H, m, CH$_2$), 2.39–2.45 (10H, m, 5 of CH$_2$), 2.78 (2H, t, J=7.5Hz, CH$_2$), 3.74 (2H, s, C$\underline{H}_2$Ar), 3.87 (3H, s, OMe), 7.11–7.15 (2H, m, Ar-H), 7.25–7.41 (3H, m, Ar-H), 7.46 (1H, d, J=8.6Hz, Ar-H), 7.55 (1H, d, J=2Hz, Ar-H), 7.67 (1H, d, J=7.4Hz, Ar-H), 8.46 (2H, s, Ar-H), 8.68 (1H, br s, NH).

b) 4-([2-N-Methylcarboxamidophenyl]methyl)-1-(3-[5-(1,2,4-triazol-4-yl)-1H-indol-3-yl]propyl)piperazine. 1.5 Hydrogen Oxalate To a solution of the ester (106 mg, 0.23 mmol) in methanol/water (10:1, 7 ml) was added KOH (39 mg, 0.69 mmol) and the mixture heated at 60° C. for 18 h. After this time the solvent was removed in vacuo and the residue dissolved in water (10 ml). The solution was adjusted to pH 7 using 1M HCl and the solvent evaporated. The residue was azeotroped with toluene (2×10 ml) and the crude acid used in the subsequent reaction without further purification.

To a solution of the resultant acid in anhydrous DMF (5 ml) was added triethylamine (51 μL, 0.37 mmol), 1-hydroxybenzotriazole (37 mg, 0.28 mmol), methylamine (191 μL of a 8.0M solution in THF, 1.5 mmol) and 1-(3-dimethylaminopropyl)-3-ethylcarbodiimide hydrochloride (71 mg, 0.37 mmol). The mixture was stirred at room temperature for 3 days, before the solvent was evaporated. The residue was azeotroped with toluene (2×10 ml) and then partitioned between dichloromethane (20 ml) and water (20 ml). The organic layer was separated, dried (Na$_2$SO$_4$) and evaporated. The residue was chromatographed on silica gel, eluting with CH$_2$Cl$_2$/MeOH/NH$_3$ (90:10:1) to give the title amide (40 mg, 38%) as a colourless oil. The 1.5 hydrogen oxalate salt was prepared, mp 150° C., (Found C, 58.48, H, 6.00, N, 16.77%. C$_{26}$H$_{31}$N$_7$O.1.5(C$_2$H$_2$O$_4$) requires C, 58.77, H, 5.78, N, 16.54%), m/e 458 (M+1)$^+$, δ (360 MHz, d$_6$-DMSO) 1.98–2.06 (2H, m), 2.48–3.20 (15H, m), 3.68 (2H, s), 7.30–7.51 (7H, m), 7.80 (1H, d, J=1.9Hz), 8.58 91H, br s), 9.01 (2H, s), 11.17 (1H, br s).

EXAMPLE 41

4-([2-N,N-Dimethylaminomethylphenyl]methyl)-1-(3-[5-(1,2,4-triazol-4-yl)-1H-indol-3-yl]propyl)piperazine. 1.5 Hydrogen Oxalate A solution of the nitrile (75 mg, 0.18 mmol), (prepared as described in Example 35) in ethanol (20 ml) was hydrogenated at 40 psi, in the presence of platinum IV oxide (100 mg) and 1M HCl (0.35 ml) for 3 h. After this time the catalyst was filtered off and the filtrate evaporated. The residue was partitioned between dichloromethane (2×20 ml) and 1M NaOH (20 ml). The combined organic layers were dried (Na$_2$SO$_4$) and evaporated in vacuo. The residue was chromatographed on silica gel, eluting with CH$_2$Cl$_2$/MeOH/NH$_3$ (40:8:1), to give the benzylamine (38 mg, 51%) as a colourless foam.

To a stirred solution of the benzylamine (38 mg, 0.09 mmol) at 0° C. in methanol (10 ml) was added sodium cyanoborohydride (17 mg, 0.27 mmol), acetic acid (25 μl, 0.44 mmol) and formaldehyde (17 μl of a 38% (w/v) aqueous solution). The cooling bath was removed and the mixture stirred at room temperature for 3 h. After this time sat. K$_2$CO$_3$ solution (5 ml) was added and the mixture stirred for 15 min. The solvents were then evaporated and the residue partitioned between dichloromethane (20 ml) and water (20 ml). The organic phase was separated, dried (Na$_2$SO$_4$) and evaporated. The residue was chromatographed on silica gel, eluting with CH$_2$Cl$_2$/MeOH/NH$_3$ (40:8:1), to give the title amine (28 mg, 69%) as a colourless foam. The 1.5 hydrogen oxalate salt was prepared, mp 161° C., (Found: C, 59.80, H, 6.82, N, 16.18%. C$_{27}$H$_{35}$N$_7$.1.5 (C$_2$H$_2$O$_4$). 0.5(H$_2$O) requires C, 59.89, H, 6.53, N, 16.30%), m/e 458 (M+1)$^+$, δ (360 MHz, d$_6$-DMSO) 1.82–1.93 (2H, m), 2.50–2.80 (18H, m), 3.86 (2H, s), 4.24 (2H, s), 7.28–7.33 (2H, m), 7.46–7.50 (5H, m), 7.78 (1H, s), 9.02 (2H, s), 11.13 (1H, br s).

EXAMPLE 42

4-(But-3-enyl)-1-(3-[5-(1,2,4-triazol-4-yl)-1H-indol-3-yl]propyl)piperazine. Hydrogen Oxalate To a solution of Intermediate 2 (100 mg, 0.32 mmol) in anhydrous DMF (5 ml) was added K$_2$CO$_3$ (53 mg, 0.39 mmol) and 4-bromo-1-butene (33 μl, 0.32 mmol). The mixture was heated at 50° C. for 45 min and then at 70° C. for 2.5 h. More bromide (16 μl, 0.16 mmol) was added and the mixture heated at 70° C. for a further 1 h. The solvent was evaporated and the residue partitioned between CH$_2$Cl$_2$ (3×20 ml) and water (20 ml). The combined organic layers were dried (Na$_2$SO$_4$) and evaporated. The residue was chromatographed on silica gel, eluting with CH$_2$Cl$_2$/MeOH/NH$_3$ (93:7:1) to give the piperazine (63 mg, 54%) as a pale yellow foam. The hydrogen oxalate salt was prepared, mp 126° C. (dec.), (Found: C, 57.75, H, 6.85, N, 17.59%. C$_{21}$H$_{28}$N$_6$. 1.0(C$_2$H$_2$O$_4$). 1.3(H$_2$O) requires C, 57.80, H, 6.88, N, 17.58%), m/e 365 (M+1)$^+$, δ (360 MHz, d$_6$-DMSO) 1.90–2.01 (2H, m), 2.23–2.30 (2H, m), 2.57–3.10 (14H, m), 5.02 (1H, d, J=10.3Hz), 5.09 (1H, dd, J=17 and 2Hz), 5.74–5.82 (1H, m), 7.29–7.33 (2H, m), 7.49 (1H, d, J=8.5Hz), 7.79 (1H, d, J=2.0Hz), 9.02 (2H, s), 11.16 (1H, br s).

EXAMPLE 43

4-(3-Methyl-but-2-enyl)-1-(3-[5-(1,2,4-triazol-4-yl)-1H-indol-3-yl]propyl)piperazine. 1.3 Hydrogen Oxalate To a solution of Intermediate 2 (200 mg, 0.65 mmol) in anhydrous DMF (5 ml) was added K$_2$CO$_3$ (107 mg, 0.78 mmol) and 4-bromo-2-methyl-2-butene (82 μl, 0.78 mmol). The mixture was heated at 50° C. for 45 min then the solvent was evaporated and the residue partitioned between CH$_2$Cl$_2$ (25 ml) and water (25 ml). The organic layer was separated and the aqueous phase washed further with CH$_2$Cl$_2$/MeOH/NH$_3$ (90:10:1) to give the title compound (75 mg, 30%) as a pale yellow gum. The 1.3 hydrogen oxalate salt was prepared, mp. 137° C. (dec.), (Found: C, 59.62, H, 6.86, N, 17.18%. $C_{22}H_{30}N_6$. 1.3($C_2H_2O_4$) requires C, 59.62, H, 6.63, N, 16.96%), m/e 379 (M+1)$^+$, δ (360 MHz, d$_6$-DMSO) 1.65 (3H, s), 1.73 (3H, s), 1.82–1.96 (2H, m) 2.51–2.90 (12H, m), 3.18 (2H, d, J=6.8Hz), 5.17–5.24 (1H, br t, J=6.8Hz), 7.30–7.33 (2H, m), 7.49 (1H, d, J=8.6Hz), 7.79 (1H, s), 9.03 (2H, s), 11.13 (1H, br s).

EXAMPLE 44

4-(Prop-2-enyl)-1-(3-[5-(1,2,4-triazol-4-yl)-1H-indol-3-yl]propyl)piperazine. 1.3 Hydrogen Oxalate To a solution of Intermediate 2 (200 mg, 0.65 mmol) in anhydrous DMF (5 ml) was added $K_2CO_3$ (78 mg, 1.29 mmol) and allyl bromide (61 μl, 0.71 mmol). The mixture was heated at 40° C. for 1.3 h then more bromide (11 μl, 0.13 mmol) was added and heating continued for a further 45 min. After this time the mixture was partitioned between $CH_2Cl_2$ (40 ml) and water (30 ml). The organic layer was separated and the aqueous phase extracted with $CH_2Cl_2$ (30 ml). The combined organic layers were dried ($Na_2SO_4$) and evaporated and the residue chromatographed on silica gel, eluting with 90:10:1 $CH_2Cl_2$/MeOH/NH$_3$. The title compound (46 mg, 20%) was isolated as a pale yellow foam. The 1.5 hydrogen oxalate salt was prepared, mp 98° C. (dec.), (Found: C, 56.94, H, 6.07, N, 17.49%. $C_{20}H_{26}N_6$. 1.5 ($C_2H_2O_4$) requires C, 56.90, H, 6.02, N, 17.31%), m/e 351 (M+1)$^+$, δ (360 MHz, d$_6$-DMSO) 1.91–2.06 (2H, m), 2.56–3.20 (14H, m), 5.23–5.30 (2H, m), 5.73–5.90 (1H, m), 7.31–7.35 (2H, m), 7.50 (1H, d, J=8.7Hz), 7.80 (1H, s), 9.03 (2H, s), 11.18 (1H, br s).

EXAMPLE 45

4-Propargyl-1-(3-[5-(1,2,4-triazol-4-yl)-1H-indol-3-yl]propyl)piperazine. 1.4 Hydrogen Oxalate To a solution of Intermediate 2 (100 mg, 0.32 mmol) in anhydrous DMF (5 ml) was added $K_2CO_3$ (53 mg, 0.39 mmol) and propargyl bromide (39 μl, 0.35 mmol). The mixture was heated at 50° C. for 1 h then the solvent was evaporated and the residue chromatographed on silica gel, eluting with $CH_2Cl_2$/MeOH/NH$_3$ (93:7:1) to give the title compound (61 mg, 54%) as a pale yellow foam. The 1.4 hydrogen oxalate salt was prepared, mp 110° C., (Found: C, 57.63, H, 6.03, N, 17.51%. $C_{20}H_{24}N_6$. 1.4($C_2H_2O_4$) requires C, 57.71, H, 5.69, N, 17.71%), m/e 349 (M+1)$^+$, δ (360 MHz, d$_6$-DMSO) 1.94–2.06 (2H, m), 2.74–2.80 (6H, m), 2.86–3.27 (7H, m), 3.32–3.43 (2H, m), 7.30–7.36 (2H, m), 7.49 (1H, d, J=8.5Hz), 7.80 (1H, s), 9.02 (2H, s), 11.18 (1H, br s).

EXAMPLE 46

4-((R,S)-1-(Phenyl)carboxamidomethyl)-1-(3-[5-(1,2,4-triazol-4-yl)-1H-indol-3-yl]propyl)piperazine. 1.5 Hydrogen Oxalate a) 4-((R,S)-1-(Phenyl)carbomethoxymethyl)-1-(3-[5-(1,2,4-triazol-4-yl)-1H-indol-3-yl]propyl)piperazine To a solution of Intermediate 2 (200 mg, 0.64 mmol) in anhydrous DMF (5 ml) was added $K_2CO_3$ (98 mg, 0.71 mmol) and methyl α-bromophenyl acetate (112 μl, 0.71 mmol), and the mixture heated at 60° C. for 90 min. The solvent was evaporated and the residue chromatographed on silica gel, eluting with $CH_2Cl_2$/MeOH (93:7) to give the α-methyl ester (205 mg, 70%) as a cream foam. δ 1.92–2.02 (2H, m), 2.42–2.70 (10H, m), 2.78 (2H, t, J=7.4Hz), 3.67 (3H, s), 4.00 (1H, s), 7.10–7.18 (2H, m), 7.27–7.41 (5H, m), 7.48 (1H, d, J=8.5Hz), 7.54 (1H, d, J=2Hz), 8.47 (2H, s), 9.05 (1H, br s).

b) 4-((R,S)-1-(Phenyl)carboxamidomethyl)-1-(3-[5-(1,2,4-triazol-4-yl)-1H-indol-3-yl]propyl)piperazine A solution of the ester (205 mg, 0.45 mmol) in methanol/water (7 ml (6:1)) was heated at 60° C. for 10 h in the presence of sodium hydroxide (36 mg, 0.89 mmol). The solvent was evaporated and the residue dissolved in water. 1M HCl was added to adjust the pH to 7 then the water was removed in vacuo. The residue was azeotroped with toluene (2×7 ml) and the crude acid used in the subsequent reaction without further purification.

To a solution of the crude acid in anhydrous DMF (7 ml) was added triethylamine (77 μl, 0.55 mmol), 1-hydroxybenzotriazole (72 mg, 0.54 mmol), ammonia (573 μl of a 2M solution in MeOH, 1.1 mmol) and 1-(3-dimethylaminopropyl)-3-ethylcarbodiimide hydrochloride (106 mg, 0.55 mmol). The mixture was stirred at room temperature for 24 h, before removal of the solvent in vacuo. The residue was azeotroped with toluene (2×10 ml) and the residue chromatographed on silica eluting with $CH_2Cl_2$/MeOH/NH$_3$ (90:10:1), to afford the title amide (158 mg, 80%) as a colourless foam. The 1.5 hydrogen oxalate salt was prepared, mp 153° C., (Found: C, 58.18, H, 5.69, N, 17.31%. $C_{25}H_{29}N_7O$. 1.5($C_2H_2O_4$) requires C, 58.12, H, 5.57, N, 16.95%), m/e 444 (M+1)$^+$, δ (360 MHz, d$_6$-DMSO) 1.90–2.06 (2H, m), 2.48–3.26 (12H, m), 3.87 (1H, s), 7.18 (1H, br s), 7.29–7.38 (7H, m), 7.49 (1H, d, J=8.6Hz), 7.62 (1H, br s), 7.79 (1H, d, J=2Hz), 9.02 (2H, s), 11.18 (1H, br s).

EXAMPLES 47 AND 48

(+)- and (−)-4-(1-(Phenyl)carboxamidomethyl)-1-(3-[5-(1,2,4-triazol-4-yl)-1H-indol-3-yl]propyl) piperazine. 1.5 Hydrogen Oxalate The racemic amide (Example 46) (121 mg, 0.27 mmol) was dissolved in ethanol (50 mg/ml). 50 μl of solution was injected onto a Chiralcel OD-H column (250×4.6 mm i.d., 5 μM) per run, using 50% ethanol in hexane as the mobile phase. Using a flow rate of 1 ml/min and U.V. detection at 285 nM, the two enantiomers were efficiently separated. The fractions containing each separate enantiomer were combined and evaporated in vacuo.

Enantiomer A (40 mg): Retention time 6.5 min.

Purity A:B=>99.5:0.5

Enantiomer B (41 mg): Retention time 10.7 min.

Purity B:A=>99.5:0.5

The 1.5 hydrogen oxalate salt of each enantiomer was prepared.

Enantiomer A: mp 148°–150° C., (Found: C, 58.11, H, 5.91, N, 17.04%. $C_{25}H_{29}N_7O$. 1.5($C_2H_2O_4$) requires C, 58.12, H, 5.57, N, 16.95%), m/e 444 (M+1)$^+$, $^1$H nmr as for Example 46.

Enantiomer B: mp 150°–153° C., (Found: C, 58.21, H, 5.89, N, 17.01%. $C_{25}H_{29}N_7O$. 1.5($C_2H_2O_4$) requires C, 58.12, H, 5.57, N, 16.95%), m/e 444 (M+1)$^+$, $^1$H nmr as for Example 46.

EXAMPLE 49

4-(1-(Phenyl)-N-methylcarboxamidomethyl)-1-(3-[5-(1,2,4-triazol-4-yl)-1H-indol-3-yl]propyl) piperazine. 1.2 Hydrogen Oxalate A solution of the ester (55 mg, 0.12 mmol) (prepared as described in Step a) Example 46) in methanol/water (5 ml (4:1)) was heated at 70° C. for 5 h, in the presence of potassium hydroxide (15 mg, 0.27 mmol). The solvent was evaporated and the residue dissolved in water. 1M HCl was added to adjust the pH to 7 then the water was removed in vacuo. The residue was azeotroped with toluene (2×7 ml) and the crude acid used in the next reaction without further purification.

To a solution of the crude acid in anhydrous DMF (5 ml) was added triethylamine (18 µl, 0.13 mmol), 1-hydroxybenzotriazole (19 mg, 0.14 mmol), methylamine (66 µl of a 2.0M solution in THF, 0.13 mmol) and 1-(3-dimethylaminopropyl)-3-ethylcarbodiimide hydrochloride (25 mg, 0.13 mmol). The mixture was stirred at room temperature for 20 h, before removal of the solvent in vacuo. The residue was chromatographed on silica gel, eluting with $CH_2Cl_2$/MeOH/$NH_3$ (90:10:1), to afford the amide (50 mg, 91%) as a colourless oil. The 1.2 hydrogen oxalate salt was prepared, mp 152° C., (Found: C, 58.55, H, 6.21, N, 16.67%. $C_{26}H_{31}N_7O$. $1.2(C_2H_2O_4)$. $H_2O$ requires C, 58.45, H, 6.11, N, 16.80%), m/e 458 (M+1)$^+$, δ (360 MHz, $d_6$-DMSO) 1.92–2.04 (2H, m), 2.54–3.22 (15H, m), 3.91 (1H, s), 7.30–7.42 (7H, m), 7.49 (1H, d, J=8.7Hz), 7.92 (1H, d, J=2Hz), 8.14 (1H, br q, J=4.6Hz), 9.01 (2H, s), 11.17 (1H br s).

EXAMPLE 50

4-(1-(Phenyl)-N,N-dimethylcarboxamidomethyl)-1-(3-[5-(1,2,4-triazol-4-yl)-1H-indol-3-yl]propyl) piperazine. 1.4 Hydrogen Oxalate A solution of the ester (83 mg, 0.18 mmol) (prepared as described in Step a) Example 46) in methanol/water (6 ml (5:1)) was heated at 70° C. for 20 h. The solvent was evaporated and the residue dissolved in water. 1M HCl was added to adjust the pH to 7 then the water was removed in vacuo. The residue was azeotroped with toluene (2×10 ml) and the crude acid used in the subsequent reaction without further purification.

To a solution of the crude acid in anhydrous DMF (5 ml) was added triethylamine (27 µl, 0.2 mmol), 1-hydroxybenzotriazole (29 mg, 0.22 mmol), dimethylamine (40 µl of a 5.6M solution in ethanol, 0.22 mmol) and 1-(3-dimethylaminopropyl)-3-ethylcarbodiimide hydrochloride (38 mg, 0.2 mmol). The mixture was stirred for 20 h, before removal of the solvent. The residue was partitioned between $CH_2Cl_2$ (20 ml) and water (20 ml). The organic phase was separated, dried $Na_2SO_4$) and evaporated. The residue was chromatographed on silica gel, eluting with $CH_2Cl_2$/MeOH/$NH_3$ (90:10:1), to give the amide (67 mg, 79%) as a colourless oil. The 1.4 hydrogen oxalate salt was prepared, mp 152° C., (Found: C, 60.01, H, 6.40, N, 16.31%. $C_{27}H_{33}N_7O$. $1.4(C_2H_2O_4)$ requires C, 59.89, H, 6.04, N, 16.41%), m/e 472 (M+1)$^+$, δ (360 MHz, $d_6$-DMSO) 1.88–2.02 (2H, m), 2.46–3.10 (18H, m), 4.67 (1H, s), 7.26–7.42 (7H, m), 7.49 (1H, d, J=8.6Hz), 7.78 (1H, s), 9.00 (2H, s), 11.16 (1H, br s).

EXAMPLE 51

4-([2-Methylcarbamoyl-1-phenyl]ethyl)-1-(3-[5-(1,2,4-triazol-4-yl)-1H-indol-3-yl]propyl)piperazine. 1.5 Hydrogen Oxalate a) 4-[(2-Amino-1-phenyl)ethyl]-1-(3-[5-(1,2,4-triazol-4-yl)-1H-indol-3-yl]propyl)piperazine To a solution of 4-[(2-hydroxy-1-phenyl)ethyl]-1-(3-[5-(1,2,4-triazol-4-yl)-1H-indol-3-yl]propyl)piperazine [Example 52, Step a)] (0.33 g, 0.77 mmol) in anhydrous THF (15 ml) at −10° C. was added triethylamine (214 µl, 1.53 mmol) followed by methanesulphonyl chloride (118 µl, 1.53 mmol). The mixture was stirred for 15 min then the precipitate removed by filtration. The filtrate was evaporated and the residue transferred with THF (10 ml) to a sealed tube. Ammonia (7.7 ml of a 2.0M solution in methanol, 15.3 mmol) was added and the mixture heated at 65° C. for 30 min. After cooling the solvents were evaporated and the residue chromatographed on silica gel, eluting with $CH_2Cl_2$/MeOH/$NH_3$ (90:10:1) to give the amine (185 mg, 56%) as a pale yellow foam. m/e 430 (M+1)$^+$, δ 1.88–2.00 (2H, m), 2.38–2.76 (12H, m), 2.79 (2H, t, J=7.5Hz), 4.11 (1H, dd, J=10.4 and 3.6Hz), 7.13–7.18 (2H, m), 7.22–7.39 (5H, m), 7.47 (1H, d, J=8.6Hz), 7.59 (1H s), 8.34 (1H, br s), 8.46 (2H, s).

b) 4-([2-Methylcarbamoyl-1-phenyl]ethyl)-1-(3-[5-(1,2,4-triazol-4-yl)-1H-indol-3-yl]propyl)piperazine. 1.5 Hydrogen Oxalate To a solution of the amine (60 mg, 0.14 mmol) in anhydrous $CH_2Cl_2$ (5 ml) at 0° C. was added triethylamine (20 µl, 0.14 mmol) followed by methyl chloroformate (11 µl, 0.14 mmol). The cooling bath was removed and the mixture stirred at room temperature for 30 min. The mixture was diluted with $CH_2Cl_2$ (15 ml) and washed with water (20 ml). The organic phase was separated and the aqueous layer extracted with $CH_2Cl_2$ (2×20 ml). The combined organic layers were dried ($Na_2SO_4$) and evaporated. The residue was chromatographed on silica gel, eluting with $CH_2Cl_2$/MeOH/$NH_3$ (90:10:1), to give the title carbamate (54 mg, 79%) as a colourless foam. The 1.5 hydrogen oxalate salt was prepared, mp 130° C. (dec.), (Found: C, 56.92, H, 6.16, N, 15.48%. $C_{27}H_{33}N_7O_2$. $1.5(C_2H_2O_4)$. $0.5(H_2O)$ requires C, 57.04, H, 5.90, N, 15.52%), m/e 488 (M+1)$^+$, δ (360 MHz, $d_6$-DMSO) 1.94–2.10 (2H, m), 2.42–3.20 (14H, m), 3.51 (3H, s), 4.67–4.79 (1H, m), 7.20–7.36 (7H, m), 7.50 (1H, d, J=8.6Hz), 7.78–7.86 (1H, m), 7.80 (1H, d, J=1.9Hz), 9.03 (2H, s), 11.19 (1H, br s).

EXAMPLE 52

4-[(2-Dimethylamino-1-phenyl)ethyl]-1-(3-[5-(1,2,4-triazol-4-yl)-1H-indol-3-yl]propyl)piperazine. 1.45 Hydrogen Oxalate a) 4-[(2-Hydroxy-1-phenyl)ethyl]-1-(3-[5-(1,2,4-triazol-4-yl)-1H-indol-3-yl]propyl)piperazine To a solution of the ester (Example 46, Step a)) (620 mg, 1.35 mmol) in anhydrous THF (20 ml) at −10° C. was added $LiAlH_4$ (1.62 ml of a 1.0M solution in ether, 1.62 mmol) dropwise. Stirring was continued at −10° C. for 2 h, then sat. $Na_2SO_4$ (5 ml) was added and the cooling bath removed. The mixture was stirred at room temperature for 15 min. then the undissolved solid filtered off. The filtrate was removed in vacuo and the residue chromatographed on silica gel, eluting with $CH_2Cl_2$/MeOH/$NH_3$ (90:10:1), to afford the alcohol (485 mg, 84%) as a colourless foam. m/e 431 (M+1)$^+$, δ (360 MHz, $CDCl_3$) 1.81–1.90 (2H, m), 2.32–2.70 (10H, m), 2.74 (2H, t, J=7.6Hz), 3.64–3.70 (2H, m), 3.96 (1H, t, J=11Hz), 7.11–7.19 (4H, m), 7.28–7.35 (3H, m), 7.45 (1H, d, J=8.6Hz), 7.52 (1H, d, J=2.0Hz), 8.35 (1H, br s), 8.44 (2H, s).

b) 4-[(2-Dimethylamino-1-phenyl)ethyl]-1-(3-[5-(1,2,4-triazol-4-yl)-1H-indol-3-yl]propyl)piperazine. 1.45 Hydrogen Oxalate To a solution of the alcohol (100 mg, 0.23 mmol) in anhydrous THF (5 ml) at 0° C. was added triethylamine (65 µl, 0.46 mmol) followed by methanesulphonyl chloride (36 µl, 0.46 mmol). The mixture was stirred for 45 min then the undissolved solid removed by filtration. The filtrate was evaporated and the residue transferred with THF (5 ml) to a sealed tube. Dimethylamine (0.83 ml of a 5.6M solution in ethanol, 4.6 mmol) was added and the mixture heated at 65° C. for 30 min. After cooling the precipitate was removed by filtration and the solvents evaporated. The residue was chromatographed on silica gel, eluting with $CH_2Cl_2$/MeOH/$NH_3$ (75:10:1), to give the piperazine (39 mg, 37%) as a colourless foam. The 1.45 hydrogen oxalate salt was prepared, mp 150° C. (dec.), (Found: C, 60.94, H, 6.87, N, 16.60%. $C_{27}H_{35}N_7$. 1.45($C_2H_2O_4$) requires C, 61.06, H, 6.50, N, 16.67%), m/e 458 (M+1)$^+$, δ (360 MHz, $d_6$-DMSO) 1.90–2.00 (2H, m), 2.36 (6H, s), 2.60–2.86 (13H, m), 3.20–3.30 (1H, m), 4.12–4.26 (1H, m), 7.30–7.33 (2H, m), 7.38–7.46 (5H, m), 7.49 (1H, d, J=8.6Hz), 7.87 (1H, s), 9.02 (2H, s), 11.15 1H, br s).

EXAMPLE 53

4-Benzyl-1-[3-(5-(1,2,4-triazol-1-yl)-1H-pyrrolo[2,3-c]pyridin-3-yl)propyl]piperazine Oxalate 1. Intermediate 4: 5-(1,2,4-Triazol-1-yl)-1H-pyrrolo[2,3-c]pyridine a) 4-Methyl-5-nitro-2-(1,2,4-triazol-1-yl)pyridine To a solution of 1,2,4-triazole (4.0 g, 58 mmol) in dry DMF (20 mL) was added potassium carbonate (12.0 g, 87 mmol) and 2-chloro-4-methyl-5-nitropyridine (10 g, 58 mmol) and the mixture stirred at ambient temperature under nitrogen for 24 hours. Ethyl acetate (500 mL) and water (250 mL) were added to the mixture and the resulting precipitate was collected by filtration to give the title compound (5.08 g, 43%) as a pale brown solid. The filtrate was separated and the organic phase was washed with water (250 mL) and brine (250 mL), dried ($MgSO_4$) and evaporated. The residue was triturated with ethyl acetate and the precipitate collected by filtration to give the title compound as a brown solid (4.11 g, 35%, overall yield 78%). mp 198°–200° C. $^1$H NMR (360 MHz, CDCl$_3$) δ 2.72 (3H, s), 7.86 (1H, s), 8.07 (1H, s), 9.03 (1H, s) and 9.15 (1H, s).

b) N,N-Dimethyl-2-(5-nitro-2-(1,2,4-triazol-1-yl)-pyridin-4-yl)ethenamine

To a suspension of 4-methyl-5-nitro-2-(1,2,4-triazol-1-yl)pyridine (4.1 g, 20 mmol) in dry DMF (30 mL) was added dimethylformamide dimethyl acetal (5.9 mL, 44 mmol) and the mixture heated at 90° C. for 20 min. The solvent was evaporated in vacuo using toluene as an azeotrope to give the title compound (5.2 g, 100%) as a dark red solid. mp 225°–228° C. $^1$H NMR (360 MHz, CDCl$_3$) δ 3.10 (6H, s) 6.13 (1H, d, J=13.1Hz), 7.54 (1H, d, J=13.1Hz), 7.81 (1H, s), 8.04 (1H, s), 8.92 (1H, s) and 9.17 (1H, s).

c) 5-(1,2,4-Triazol-1-yl)-1H-pyrrolo[2,3-c]pyridine

N,N-Dimethyl-2-(5-nitro-2-(1,2,4-triazol-1-yl)pyridin-4-yl)ethenamine (8 g, 31 mmol) was hydrogenated over platinum oxide (1.6 g) in ethanol (150 mL) at 30 psi of hydrogen for 1 hour. The catalyst was removed by filtration and the solvent evaporated in vacuo. The residue was chromatographed on silica eluting with ethyl acetate to afford an orange/brown solid. This was triturated with ether and the precipitate collected by filtration to give the title compound (2.89 g, 51%) as a pink solid. mp 203°–205° C. $^1$H NMR (360 MHz, $d_6$-DMSO) δ 6.67 (1H, d, J=3.0Hz), 7.76 (1H, d, J=2.9Hz), 8.01 (1H, s), 8.23 (1H, s), 8.70 (1H, s), 9.25 (1H, s) and 11.86 (1H, br s).

2. 3-Formyl-5-(1,2,4-triazol-1-yl)-1H-pyrrolo[2,3-c]pyridine

A mixture of Intermediate 4 (3.86 g, 20.9 mmol) and hexamethylenetetramine (4.39 g, 31.3 mmol) was refluxed in 33% aqueous acetic acid (35 mL) for 90 min. Water (40 mL) was added and the mixture cooled in ice for 90 min. The precipitate was collected by filtration to give the title compound (3.31 g, 74%) as a beige solid. mp 220° C. (dec.). $^1$H NMR (250 MHz, $d_6$-DMSO) δ 8.29 (1H, s), 8.46 (1H, s), 8.65 (1H, s), 8.81 (1H, s), 9.33 (1H, s), 10.04 (1H, s) and 12.78 (1H, br s).

3. 1-tert-Butyloxycarbonyl-3-formyl-5-(1,2,4-triazol-1-yl)pyrrolo[2,3-c]pyridine To a solution of 3-formyl-5-(1,2,4-triazol-1-yl)-1H-pyrrolo[2,3-c]pyridine (3.4 g, 16 mmol) in acetonitrile (75 mL) was added di-tert-butyl dicarbonate (4.18 g, 19 mmol) and dimethylaminopyridine (98 mg, 0.8 mmol) and the mixture was stirred at ambient temperature under nitrogen for 16 hours. The solvent was evaporated in vacuo and the residue triturated with ether. The precipitate was collected by filtration and chromatographed on silica eluting with 20% EtOAc in DCM to give the title compound (3.98 g, 70%) as a colourless solid. mp 190° C. (dec.). $^1$H NMR (360 MHz, $d_6$-DMSO) δ 1.70 (9H, s), 8.33 (1H, s), 8.51 (1H, s), 9.00 (1H, s), 9.20 (1H, s), 9.41 (1H, s) and 10.15 (1H, s).

4. Ethyl-3-[1-tert-butyloxycarbonyl-5-(1,2,4-triazol-1-yl)pyrrolo[2,3-c]pyridin-3-yl]prop-2-enoate A solution of 1-tert-butyloxycarbonyl-3-formyl-5-(1,2,4-triazol-1-yl)pyrrolo[2,3-c]pyridine (1.5 g, 4.8 mmol) and (carboethoxymethylene)triphenylphosphorane (2.0 g, 5.8 mmol) in toluene (30 mL) was heated at 80° C. under nitrogen for 90 min. The mixture was allowed to cool and the solvent was evaporated in vacuo. The residue was chromatographed on silica eluting with 20% EtOAc in DCM to give a colourless solid. This was triturated with ether and the solid rechromatographed on silica with 20% EtOAc in DCM to give the title compound (1.77 g, 96%) as a colourless solid. mp 178°–181° C. $^1$H NMR (360 MHz, CDCl$_3$) δ 1.37 (3H, t, J=7.1Hz), 1.73 (9H, s), 4.31 (2H, q, J=7.1Hz), 6.59 (1H, d, J=16.2Hz), 7.81 (1H, d, J=16.2Hz), 8.03 (1H, s), 8.14 (1H, s), 8.30 (1H, s), 9.21 (1H, s) and 9.26 (1H, br s).

5. Ethyl-3-(5-(1,2,4-triazol-1-yl)-1H-pyrrolo[2,3-c]pyridin-3-yl)prop-2-enoate

A solution of ethyl-3-[1-tert-butyloxycarbonyl-5-(1,2,4-triazol-1-yl)pyrrolo[2,3-c]pyridin-3-yl]prop-2-enoate (1.73 g, 4.5 mmol) and trifluoroacetic acid (5 mL) in dry DCM (20 mL) was stirred at ambient temperature under nitrogen for 5 hours. The solvent was evaporated in vacuo and the residue azeotroped with toluene. The residue was chromatographed on silica eluting with 20% EtOAc in DCM followed by a gradient of 5 to 10% MeOH in DCM to give a colourless solid. This was triturated with ether to give the title compound (1.05 g, 82%) as a colourless solid. mp 235°–238° C. $^1$H NMR (360 MHz, $d_6$-DMSO) δ 1.29 (3H, t, J=7.1Hz), 4.20 (2H, q, J=7.1Hz), 6.44 (1H, d, J=16.0Hz), 7.92 (1H, d, J=16.1Hz), 8.22 (1H, s), 8.27 (1H, s), 8.33 (1H, d, J=2.7Hz), 8.76 (1H, s), 9.31 (1H, s) and 12.46 (1H, br s).

6. Ethyl 3-(5-(1,2,4-triazol-1-yl)-1H-pyrrolo[2,3-c]pyridin-3-yl)propionate

Ethyl-3-(5-(1,2,4-triazol-1-yl)-1H-pyrrolo[2,3-c]pyridin-3-yl)prop-2-enoate (0.5 g, 1.8 mmol) was hydrogenated over palladium on carbon (10%, 0.2 g) in methanol (75 mL) at 45 psi of hydrogen for 90 min. The catalyst was removed by filtration and the solvent evaporated in vacuo to give the title compound (0.455 g, 90%) as a colourless solid. mp 129°–131° C. $^1$H NMR (360 MHz, CDCl$_3$) δ 1.24 (3H, t, J=7.1Hz), 2.72 (2H, t, J=7.4Hz), 3.13 (2H, t, J=7.4Hz), 4.14 (2H, q, J=7.1Hz), 7.31 (1H, d, J=2.3Hz), 8.08 (1H, s), 8.11 (1H, s), 8.54–8.60 (2H, m) and 9.15 (1H, s).

7. 3-(5-(1,2,4-Triazol-1-yl)-1H-pyrrolo[2,3-c]pyridin-3-yl)propanoic acid (4-benzylpiperazinyl)amide To a solution of ethyl 3-(5-(1,2,4-triazol-1-yl)-1H-pyrrolo[2,3-c]pyridin-3-yl)propionate (0.43 g, 1.5 mmol) in methanol (20 mL) was added NaOH (4M, 1 mL) and the mixture was heated at 50° C. for 5 hours. After cooling the solution was neutralised (5M, HCl) and the solvents evaporated in vacuo to give 3-(5-(1,2,4-triazol-1-yl)-1H-pyrrolo[2,3-c]pyridin-3-yl)propionic acid (0.65 g) as a colourless solid. $^1$H NMR (360 MHz, d$_6$-DMSO) δ 2.60 (2H, t, J=7.5Hz), 2.98 (2H, t, J=7.4Hz), 7.55 (1H, s), 7.98 (1H, s), 8.23 (1H, s), 8.62 (1H, s), 9.24 (1H, s) and 11.74 (1H, br s). This was used without purification in the next step.

To a suspension of 3-(5-(1,2,4-triazol-1-yl)-1H-pyrrolo[2,3-c]pyridin-3-yl)propionic acid (0.65 g) in dry DMF (5 mL) was added 1-benzylpiperazine (0.36 mL, 2.3 mmol), 1-hydroxybenzotriazole (0.255 g, 1.9 mmol), 1-ethyl-3-[3-(dimethylamino)propyl]carbodiimide hydrochloride (0.362 g, 1.9 mmol) and triethylamine (0.26 mL, 1.9 mmol) and this mixture was stirred at ambient temperature under nitrogen for 16 hours. The solvent was evaporated in vacuo and the residue was partitioned between ethyl acetate (25 mL) and water (25 mL) and Na$_2$CO$_3$ (sat., 1 mL). The two phases were separated and the aqueous phase was extracted with ethyl acetate (3×25 mL). The combined organics were dried (Na$_2$SO$_4$) and evaporated in vacuo. The residue was chromatographed on silica eluting with a gradient of 5 to 10% MeOH in DCM to give the title compound (0.625 g, 100%) as a pale yellow foam. $^1$H NMR (360 MHz, CDCl$_3$) δ 2.28–2.46 (4H, m), 2.70 (2H, t, J=7.1Hz), 3.15 (2H, t, J=7.2Hz), 3.37–3.43 (2H, m), 3.50 (2H, s), 3.60–3.68 (2H, m), 7.23–7.34 (6H, m), 8.05 (1H, s), 8.10 (1H, s), 8.58 (1H, s), 8.69 (1H, br s) and 9.14 (1H, s).

8. 4-Benzyl-1-[3-(5-(1,2,4-triazol-1-yl)-1H-pyrrolo[2,3-c]pyridin-3-yl)propyl]piperazine oxalate To a solution of LiAlH$_4$ in ether (1.0M, 2.2 mL, 2.2 mmol) and dry THF (5 mL) was added dropwise a solution of 3-(5-(1,2,4-triazol-1-yl)-1H-pyrrolo[2,3-c]pyridin-3-yl) propionic acid (4-benzylpiperazinyl)amide (0.3 g, 0.72 mmol) in dry THF (5 mL) at ambient temperature. The mixture was heated at 50° C. for 30 min. After cooling water (87 μL) was added followed by sodium hydroxide (4M, 87 μL), followed by water (260 μL). The solid was removed by filtration and the solvent evaporated in vacuo. The residue was chromatographed on silica eluting with a gradient of 5 to 10% MeOH in DCM followed by 90:10:1, DCM:MeOH:NH$_3$ to give the free base (0.188 g, 65%) as a pale yellow foam. The free base was dissolved in Et$_2$O:MeOH (10:1, 5 mL) and treated dropwise with a solution of oxalic acid (42 mg, 0.47 mmol) in ether (1 mL). The precipitate formed was collected by filtration to give the title compound (170 mg) as a cream solid. mp 180° C. (dec.). Found: C, 58.01; H, 5.79; N, 18.20. C$_{23}$H$_{27}$N$_7$.1.5(CO$_2$H)$_2$ requires C, 58.20; H, 5.64; N, 18.27%. $^1$H NMR (360 MHz, d$_6$-DMSO) δ 1.92 (2H, m), 2.53–3.24 (12H, m), 3.64 (2H, d), 7.27–7.40 (5H, m), 7.60 (1H, s), 7.99 (1H, s), 8.23 (1H, s), 8.65 (1H, s), 9.25 (1H, s) and 11.70 (1H, br s).

EXAMPLE 54

4-Benzyl-1-[3-(5-(1,2,4-triazol-4-yl)-1H-pyrrolo[2,3-c]pyridine-3-yl)propyl]piperazine Oxalate 1. Intermediate 5: 5-(1,2,4-Triazol-4-yl)-1H-pyrrolo[2,3-c]pyridine a) 2-Acetylamino-4-methyl-5-nitropyridine 2-Amino-4-methyl-5-nitropyridine (28.4 g, 0.185 mol) was heated at 90° C. in acetic anhydride (100 mL) for 3 hours. After cooling the solvent was evaporated in vacuo and the residue was azeotroped with toluene to give a yellow solid. This was triturated with ether and the solid was collected by filtration to give the title compound (33.8 g, 93%) as a pale yellow solid. mp 153°–154° C. $^1$H NMR (360 MHz, CDCl$_3$) δ 2.27 (3H, s), 2.70 (3H, s), 8.17 (1H, br s), 8.24 (1H, s) and 8.96 (1H, s).

b) N,N-Dimethyl-2-(2-acetylamino-5-nitropyridin-4-yl)ethenamine

To a solution of 2-acetylamino-4-methyl-5-nitropyridine (33.8 g, 0.173 mol) in dry DMF (300 mL) was added dimethylformamide dimethyl acetal (50.7 mL, 0.381 mol) and the mixture heated at 90° C. for 90 min. The solvent was evaporated in vacuo using toluene as an azeotrope. The residue was triturated with ether and the solid collected by filtration to give the title compound (33 g, 76%) as an orange solid. mp 193°–196° C. $^1$H NMR (250 MHz, CDCl$_3$) δ 2.23 (3H, s), 3.04 (6H, s), 6.12 (1H, d, J=13.1Hz), 7.43 (1H, d, J=13.1Hz), 8.17 (1H, br s), 8.27 (1H, s) and 8.83 (1H, s).

c) 5-Acetylamino-1H-pyrrolo[2,3-c]pyridine

N,N-Dimethyl-2-(2-acetylamino-5-nitropyridin-4-yl)ethenamine (6 g, 24 mmol) was hydrogenated over platinum oxide (0.5 g) in ethanol (120 mL) at 35 psi of hydrogen for 15 min. The catalyst was removed by filtration and the solvent evaporated in vacuo. The residue was chromatographed on silica eluting with a gradient of 5 to 10% MeOH in DCM to afford a purple solid. This was triturated with ether and the precipitate collected by filtration to give the title compound (1.4 g, 33%) as a beige solid. mp 220° C. (dec.). $^1$H NMR (360 MHz, d$_6$-DMSO) δ 2.07 (3H, s), 6.45 (1H, s), 7.55–7.57 (1H, m), 8.21 (1H, s), 8.46 (1H, s), 10.16 (1H, br s) and 11.42 (1H, br s).

d) 5-Amino-1H-pyrrolo[2,3-c]pyridine

5-Acetylamino-1H-pyrrolo[2,3-c]pyridine (0.61 g, 3.5 mmol) was heated at reflux in methanolic KOH (2M, 15 mL) under nitrogen for 8 hours. The solvent was evaporated in vacuo and the residue partitioned between dichloromethane (100 mL) and water (100 mL). The two layers were separated and the aqueous phase was extracted with n-butanol (3×100 mL). The combined organics were evaporated in vacuo and the residue chromatographed on silica eluting with 5 to 10% MeOH in DCM followed by a gradient of 90:10:1 to 80:20:1, DCM:MeOH:NH$_3$ to give the title compound (0.384 g, 83%) as a red solid. mp 183°–186° C. $^1$H NMR (360 MHz, d$_6$-DMSO) δ 4.95 (2H, br s), 6.13–6.15 (1H, m), 6.52 (1H, s), 7.34–7.37 (1H, m), 8.17 (1H, s) and 10.90 (1H, br s).

e) 5-(1,2,4-Triazol-4-yl)-1H-pyrrolo[2,3-c]pyridine

5-Amino-1H-pyrrolo[2,3-c]pyridine (2 g, 15 mmol), diformylhydrazine (1.32 g, 15 mmol) and dry DMF (1.5 mL) were heated at 170° C. under nitrogen for 4 hours. After cooling, ethyl acetate (10 mL) and water (10 mL) were added. The mixture was stirred vigorously for 15 min. The resulting precipitate was collected by filtration, and chromatographed on silica eluting with a gradient of 5 to 7 to 10% MeOH in DCM to give a yellow solid. This was triturated with ether to give the title compound (1.65 g, 59%) as a yellow/green crystalline solid. mp 254°–257° C. $^1$H NMR (360 MHz, d$_6$-DMSO) δ 6.63 (1H, d, J=3.1Hz), 7.79 (1H, d, J=3.0Hz), 7.99 (1H, s), 8.71 (1H, s), 9.21 (2H, s) and 11.89 (1H, br s).

2. 3-Formyl-5-(1,2,4-triazol-4-yl)-1H-pyrrolo[2,3-c]pyridine

A mixture of Intermediate 5 (1.62 g, 8.7 mmol) and hexamethylenetetramine (1.47 g, 10.5 mmol) was refluxed in 33% aqueous acetic acid (10 mL) for 75 min. The mixture was cooled in ice for 2 hours and the precipitate was collected by filtration to give the title compound (0.71 g, 38%) as a beige solid. The filtrate was evaporated and the residue chromatographed on silica eluting with 10% MeOH in DCM to give the title compound (0.39 g, 21%) (overall yield 59%), as a yellow solid. mp 155° C. (dec.). $^1$H NMR (360 MHz, d$_6$-DMSO) δ 8.35 (1H, s), 8.68 (1H, s), 8.83 (1H, s), 9.30 (2H, s), 10.05 (1H, s) and 12.74 (1H, br s).

3. 1-tert-Butyloxycarbonyl-3-formyl-5-(1,2,4-triazol-4-yl)pyrrolo[2,3-c]pyridine To a solution of 3-formyl-5-(1,2,4-triazol-1-yl)-1H-pyrrolo[2,3-c]pyridine (1.1 g, 5.2 mmol) in acetonitrile (30 mL) was added di-tert-butyldicarbonate (1.69 g, 7.8 mmol) and dimethylaminopyridine (63 mg, 0.52 mmol) and the mixture was stirred at ambient temperature under nitrogen for 16 hours. The solvent was evaporated in vacuo and the residue chromatographed on silica eluting with a gradient of 2 to 5% MeOH in DCM to give a yellow solid. This was triturated with ether. The precipitate was collected by filtration to afford the title compound (0.71 g, 49%) as a cream solid. mp 170° C. (dec.). $^1$H NMR (360 MHz, d$_4$-MeOH) δ 1.76 (9H, s), 8.49 (1H, s), 8.80 (1H, s), 9.29 (2H, s), 9.34 (1H, s) and 10.12 (1H, s).

4. Ethyl 3-[5-(1,2,4-triazol-4-yl)-1H-pyrrolo[2,3-c]pyridin-3-yl]prop-2-enoate

A solution of 1-tert-butyloxycarbonyl-3-formyl-5-(1,2,4-triazol-4-yl)pyrrolo[2,3-c]pyridine (0.71 g, 2.3 mmol) and (carboethoxymethylene)triphenylphosphorane (0.95 g, 2.7 mmol) in toluene (25 mL) was heated at 80° C. under nitrogen for 2 hours. The mixture was allowed to cool and the solvent evaporated in vacuo. The residue was chromatographed on silica eluting with 20% EtOAC in DCM, followed by a gradient of 2 to 5% MeOH in DCM to afford ethyl 3-[1-tert-butyloxycarbonyl-5-(1,2,4-triazol-4-yl)pyrrolo[2,3-c]pyridin-3-yl]prop-2-enoate (0.93 g), contaminated with minor impurities, as a cream solid. $^1$H NMR (360 MHz, CDCl$_3$) δ 1.38 (3H, t, J=7.1Hz), 1.73 (9H, s), 4.32 (2H, q, J=7.1Hz), 6.51 (1H, d, J=16.2Hz), 7.76 (1H, s), 7.80 (1H, d, J=15.7Hz), 8.09 (1H, s), 8.95 (2H, s) and 9.33 (1H, s). This was used without further purification.

A solution of ethyl 3-[1-tert-butyloxycarbonyl-5-(1,2,4-triazol-4-yl)pyrrolo[2,3-c]pyridin-3-yl]prop-2-enoate (0.92 g) and trifluoroacetic acid (5 mL) in dry DCM (20 mL) was stirred at ambient temperature under nitrogen for 16 hours. The solvent was evaporated in vacuo and the residue azeotroped with toluene. The residue was chromatographed on silica eluting with 5 to 20% MeOH in DCM to give a cream solid. This was triturated with MeOH and the solid was collected by filtration to afford the title compound (0.4 g, 62%) as a cream solid. mp 235° C. (dec.). $^1$H NMR (360 MHz, d$_6$-DMSO) δ 1.29 (3H, t, J=7.1Hz), 4.21 (2H, q, J=7.1Hz), 6.68 (1H, d, J=16.2Hz), 7.91 (1H, d, J=16.1Hz), 8.33 (1H, s), 8.36 (1H, s), 8.74 (1H, s), 9.35 (2H, s) and 12.44 (1H, br s).

5. Ethyl 3-(5-(1,2,4-triazol-4-yl)-1H-pyrrolo[2,3-c]pyridin-3-yl)propionate

Ethyl 3-(5-(1,2,4-triazol-4-yl)-1H-pyrrolo[2,3-c]pyridin-3-yl)prop-2-enoate (0.4 g, 1.4 mmol) was hydrogenated over palladium on carbon (10%, 0.25 g) in ethanol (50 mL) at 45 psi of hydrogen for 6 hours. The catalyst was removed by filtration and the solvent evaporated in vacuo to give the title compound (0.32 g, 80%) as a colourless solid. mp 215°–218° C. $^1$H NMR (360 MHz, CDCl$_3$: d$_4$-MeOH 9:1) δ 1.23 (3H, t, J=7.1Hz), 2.72 (2H, t, J=7.4Hz), 3.12 (2H, t, J=7.4Hz), 4.13 (2H, q, J=7.1Hz), 7.36 (1H, s), 7.61 (1H, s), 8.60 (1H, s) and 8.89 (2H, s).

6. 3-(5-(1,2,4-Triazol-4-yl)-1H-pyrrolo[2,3-c]pyridin-3-yl)propionic acid (4-benzylpiperazinyl)amide To a solution of ethyl 3-(5-(1,2,4-triazol-4-yl)-1H-pyrrolo[2,3-c]pyridin-3-yl)propionate (0.115 g, 0.4 mmol) in methanol (5 mL) was added NaOH (4M, 0.5 mL, 2 mmol) and the mixture heated at 40° C. for 16 hours. After cooling the solution was neutralised (5M HCl) and the solvents evaporated to give 3-(5-(1,2,4-triazol-4-yl)-1H-pyrrolo[2,3-c]pyridin-3-yl)propionic acid (0.23 g) as a colourless solid. $^1$H NMR (360 MHz, d$_6$-DMSO) δ 2.48–2.55 (2H, m), 2.96 (2H, t, J=7.1Hz), 7.54 (1H, s), 8.03 (1H, s), 8.62 (1H, s), 9.24 (2H, s) and 11.81 (1H, br s). This was used without further purification in the next step.

To a suspension of 3-(5-(1,2,4-triazol-4-yl)-1H-pyrrolo[2,3-c]pyridin-3-yl)propionic acid (0.23 g) in dry DMF (3 mL) was added 1-benzylpiperazine (0.1 mL, 0.58 mmol), 1-hydroxybenzotriazole (66 mg, 0.49 mmol), 1-ethyl-3-[3-(dimethylamino)propyl]carbodiimide hydrochloride (93 mg, 0.49 mmol) and triethylamine (68 μL, 0.4 mmol) and this mixture was stirred at ambient temperature under nitrogen for 24 hours. The solvent was evaporated in vacuo and the residue partitioned between ethyl acetate (25 mL) and water (20 mL). The two phases were separated and the aqueous phase was extracted with ethyl acetate (3×25 mL). The combined organics were dried (Na$_2$SO$_4$) and evaporated in vacuo. The residue was chromatographed on silica eluting with 90:10:1, DCM:MeOH:NH$_3$ to give the title compound (30 mg, 19%) as a colourless solid. mp 185° C. (dec.). $^1$H NMR (360 MHz, CDCl$_3$:d$_4$-MeOH 9:1) δ 2.29–2.34 (2H, m), 2.35–2.42 (2H, m), 2.70 (2H, t, J=7.4Hz), 3.12 (2H, t, J=7.4Hz), 3.36–3.43 (2H, m), 3.48 (2H, s), 3.58–3.64 (2H, m), 7.24–7.35 (5H, m), 7.37 (1H, s), 7.67 (1H, s), 8.60 (1H, s) and 8.93 (2H, s).

7. 4-Benzyl-1-[3-(5-(1,2,4-triazol-4-yl)-1H-pyrrolo[2,3-c]pyridin-3-yl)propyl]piperazine oxalate To a suspension of 3-(5-(1,2,4-triazol-4-yl)-1H-pyrrolo[2,3-c]pyridin-3-yl)propionic acid (4-benzylpiperazinyl)amide (30 mg, 0.073 mmol) in dry THF (3 mL) was added dropwise a solution of LiAlH$_4$ in ether (1.0M, 144 μL, 0.144 mmol). The mixture was stirred at ambient temperature under nitrogen for 5 min and then heated at 50° C. for another 10 min. Further LiAlH$_4$ in ether (1M, 73 μL, 0.073 mmol) was added and the mixture heated at 50° C. for another 10 min. After cooling, water (9 μL) was added followed by sodium hydroxide (4M, 9 μL), followed by water (27 μL). The solid was removed by filtration and the solvent evaporated in vacuo. The residue was chromatographed on silica eluting with 90:10:1, DCM:MeOH:NH$_3$ to give the free base (20 mg, 69%) as a colourless solid. The free base (15 mg, 0.037 mmol) was dissolved in ether:MeOH (2:3, 5 mL) and treated dropwise with a solution of oxalic acid (3.4 mg, 0.037 mmol) in ether (1 mL). The precipitate formed was collected by filtration to give the title compound (12 mg) as a cream solid. mp 148° C. (dec.). Found: C, 56.00; H, 5.76; N, 16.20. C$_{23}$H$_{27}$N$_7$.2.05(CO$_2$H)$_2$.0.1(Et$_2$O) requires C, 55.65; H, 5.45; N, 16.52%. $^1$H NMR (360 MHz, d$_6$-DMSO) δ 1.94–2.06 (2H, m), 2.46–3.16 (12H, m), 3.62 (2H, s), 7.23–7.38 (5H, m), 7.59 (1H, s), 7.99 (1H, s), 8.64 (1H, s), 9.21 (2H, s) and 11.67 (1H, br s).

EXAMPLE 55

4-[2-(4-Acetamidophenyl)ethyl]-1-[3-(5-(1,2,4-triazol-1-yl)-1H-pyrrolo[2,3-c]pyridin-3-yl)propyl]piperazine. 1.65 Hydrogen Oxalate a) 3-(5-(1,2,4-Triazol-1-yl)-1H-pyrrolo[2,3-c]pyridin-3-yl)propionic acid (4-tert-butyloxycarbonylpiperazinyl)amide To a solution of 3-(5-(1,2,4-triazol-1-yl)-1H-pyrrolo[2,3-c]pyridin-3-yl) propionic acid (0.34 g, 1.3 mmol) (prepared as described in Example 53 Step 7) in anhydrous DMF (5 ml) was added 1-tert-butyloxycarbonylpiperazine (0.5 g, 2.7 mmol), 1-hydroxybenzotriazole (225 mg, 1.7 mmol), 1-(3-dimethylaminopropyl)-3-ethylcarbodiimide hydrochloride (0.45 g, 2.3 mmol) and triethylamine (0.23 ml, 1.7 mmol). The mixture was stirred at room temperature for 2 days. The solvent was evaporated and the residue partitioned between ethyl acetate (25 ml) and water (20 ml). The organic layer was separated and the aqueous phase extracted with ethyl acetate (3×20 ml). The combined organic layers were dried ($Na_2SO_4$) and evaporated. The residue was chromatographed on silica gel, eluting with $CH_2Cl_2$/MeOH (90:10) to afford the title compound, with some impurities, as a pale yellow foam.

The process was repeated using the acid (78 mg, 0.3 mmol), 1-(tert-butyloxycarbonyl)piperazine (113 mg, 0.61 mmol), 1-hydroxybenzotriazole (51 mg, 0.38 mmol), 1-(3-dimethylaminopropyl)-3-ethylcarbodiimide hydrochloride (101 mg, 0.53 mmol) and triethylamine (74 μl, 0.53 mmol). The residue was combined with the pale yellow foam from the first run and chromatographed on silica gel, eluting with $CH_2Cl_2$/MeOH (90:10). The desired amide (478 mg, 70%) was isolated as a colourless foam, m/e 426 $(M+1)^+$, δ (360 MHz,$CDCl_3$) 1.46 (9H, s), 2.72 (2H, t, J=7.2Hz), 3.17 (2H, t, J=7.2Hz), 3.30–3.42 (6H, m), 3.60–3.64 (2H, m), 7.35 (1H, s), 8.06 (1H, s), 8.10 (1H, s), 8.56 (1H, s), 8.66 (1H, br s), 9.15 (1H, s).

b) 4-(tert-Butyloxycarbonyl)-1-[3-(5-(1,2,4-triazol-1-yl)-1H-pyrrolo[2,3-c]pyridin-3-yl)propyl]piperazine To a solution of the amide (0.21 g, 0.49 mmol) in anhydrous THF (10 ml) was added $LiAlH_4$ (1.48 ml of a 1.0M solution in ether, 1.48 mmol) dropwise. The mixture was stirred at room temperature for 10 min before the sequential addition of water (59 μl), sodium hydroxide (4M, 59 μl) and water (175 μl). The resultant solid was removed by filtration and the filtrate evaporated. The residue was chromatographed on silica gel, eluting with $CH_2Cl_2$/MeOH/$NH_3$ (90:10:1), to give the title amine (125 mg, 62%) as a pale yellow gum, m/e 412 $(M+1)^+$, δ (250 MHz, $d_4$-MeOH) 1.45 (9H, s), 1.88–2.00 (2H, m), 2.39–2.47 (6H, m), 2.85 (2H, t, J=7.4Hz), 3.41–3.45 (4H, m), 7.46 (1H, s), 8.07 (1H, s), 8.16 (1H, s), 8.60 (1H, s), 9.21 (1H, s).

c) 4(H)-1-[3-(5-(1,2,4-triazol-1-yl)-1H-pyrrolo[2,3-c]pyridin-3-yl)propyl]piperazine To a solution of the carbamate (128 mg, 0.31 mmol) in anhydrous dichloromethane (20 ml) was added trifluoroacetic acid (2 ml). The mixture was stirred at room temperature for 3 h then the solvent was evaporated and the residue azeotroped with toluene (2×20 ml). The residue was partitioned between "BuOH (4×25 ml) and NaOH (1M, 25 ml). The combined organic layers were evaporated and the residue chromatographed on silica, eluting with $CH_2Cl_2$/MeOH/$NH_3$ (40:10:1) to give the deprotected amine (80 mg, 83%) as a pale yellow gum, m/e 312 $(M+1)^+$, δ (250 MHz, $d_4$-MeOH) 1.80–1.91 (2H, m), 2.32–2.46 (6H, m), 2.75 (2H, t, J=7.3Hz), 2.82–2.86 (4H, m), 7.37 (1H, s), 7.97 (1H, s), 8.07 (1H, s), 8.49 (1H, s), 9.12 (1H, s).

d) 4-[2-(4-Acetamidophenyl)ethyl]-1-[3-(5-(1,2,4-triazol-1-yl)-1H-pyrrolo[2,3-c]pyridin-3-yl)propyl]piperazine. 1.65 Hydrogen Oxalate To a solution of the amine (86 mg, 0.26 mmol) in anhydrous DMF (3 ml) was added $K_2CO_3$ (71 mg, 0.51 mmol) and 2-(4-acetamidophenyl)ethyl bromide (75 mg, 0.31 mmol). The mixture was partitioned between dichloromethane (20 ml) and water (20 ml). The aqueous phase was extracted with dichloromethane (20 ml) followed by butanol (20 ml). The combined organics were evaporated and the residue chromatographed on silica, eluting with $CH_2Cl_2$/MeOH/$NH_3$ (40:10:1) to give the title compound (75 mg, 62%) as a colourless solid. The 1.65 hydrogen oxalate salt was prepared, mp 190° C.(dec.), (Found: C, 55.08, H, 5.93, N, 17.58%. $C_{26}H_{32}N_8O$. 1.65($C_2H_2O_4$). $H_2O$ requires C, 55.06, H, 5.88, N, 17.53%), m/e 473 $(M+1)^+$, δ (360 MHz, $d_6$-DMSO) 1.88–2.02 (5H, m), 2.66–3.14 (16H, m), 7.15 (2H, d, J=8.4Hz), 7.48 (2H, d, J=8.4Hz), 7.59 (1H, s), 7.99 (1H, s), 8.23 (1H, s), 8.64 (1H, s), 9.25 (1H, s), 9.87 (1H, s), 11.68 (1H, br s).

EXAMPLE 56

4-[2-(4-Acetamidophenyl)ethyl]-1-[3-(5-(1,2,4-triazol-4-yl)-1H-pyrrolo[2,3-c]pyridin-3-yl)propyl] piperazine. 2 Hydrogen Oxalate a) 4(H)-1-[3-(5-(1,2,4-triazol-4-yl)-1H-pyrrolo[2,3-c]pyridin-3-yl)propyl]piperazine A solution of 4-benzyl-1-[3-(5-(1,2,4-triazol-4-yl)-1H-pyrrolo[2,3-c]pyridin-3-yl)propyl]piperazine (Example 54) (59 mg, 0.15 mmol) in ethanol (25 ml) was hydrogenated at 45 psi for 4 h in the presence of palladium hydroxide on carbon (Pearlman's catalyst) (175 mg). The catalyst was removed by filtration and the solvent evaporated. The residue was chromatographed on silica, eluting with $CH_2Cl_2$/MeOH/$NH_3$ (40:10:1) to give the piperazine (38 mg, 79%) as a pale yellow gum. m/e 312 $(M+1)^+$, δ (250 MHz, $CDCl_3$+$d_4$-MeOH) 1.91–1.98 (2H, m), 2.56 (2H, t, J=5.3Hz), 2.70–2.78 (4H, m), 2.83 (2H, t, J=5.3Hz), 3.14–3.24 (4H, m), 7.39 (1H, s), 7.67 (1H, s), 8.62 (1H, s), 8.97 (2H, s).

b) 4-[2-(4-Acetamidophenyl)ethyl]-1-[3-(5-(1,2,4-triazol-4-yl)-1H-pyrrolo[2,3-c]pyridin-3-yl)propyl]piperazine. 2 Hydrogen Oxalate To a solution of the piperazine prepared in Step a) (52 mg, 0.17 mmol) in anhydrous DMF (2 ml) was added $K_2CO_3$ (46 mg, 0.33 mmol) and 2-(4-acetamidophenyl)ethyl bromide (49 mg, 0.2 mmol). The mixture was heated at 50° C. for 5 h then the solvent was evaporated. The residue was chromatographed on silica, eluting with $CH_2Cl_2$/MeOH/$NH_3$ (90:10:1→40:10:1) to give the title compound (37 mg, 46%) as a colourless solid. The 2.0 hydrogen oxalate salt was prepared, mp 138° C. (dec.), (Found: C, 52.31, H, 6.06, N, 16.63%. $C_{26}H_{32}N_8O$. 2($C_2H_2O_4$). 2($H_2O$) requires C, 52.32, H, 5.85, N, 16.27%), m/e 473 $(M+1)^+$, δ (360 MHz, $d_6$-DMSO) 1.90–2.01 (5H, m), 2.66–3.10 (16H, m), 7.14 (2H, d, J=8.4Hz), 7.48 (2H, d, J=8.4Hz), 7.60 (1H, s), 8.00 (1H, s), 8.64 (1H, s), 9.22 (2H, s), 9.87 (1H, s), 11.68 (1H, br s).

EXAMPLE 57

1-(3-[5-(1,2,4-Triazol-4-yl)-1H-indol-3-yl]propyl)-4-(4-fluorophenyl) methylpiperazine. 2.5 Hydrogen Oxalate Prepared from Intermediate 2 and 4-fluorobenzaldehyde using the general reductive amination procedure; mp. 213°–215° C.; (Found: C, 53.91, H, 5.22, N, 12.73. $C_{24}H_{27}N_6F$. 2.5($C_2H_2O_4$) requires C, 54.12, H, 5.01, N, 13.05%), δ (250 MHz, $d_6$-DMSO) 1.92–2.08 (2H, m, $CH_2$), 2.52–3.22 (14H, m, 7 of $CH_2$), 3.59 (2H, s, $CH_2$), 7.10–7.40 (6H, m, Ar-H), 7.49 (1H, d, J=8.6Hz, Ar-H), 7.80 (1H, d, J=1.9Hz, Ar-H), 9.03 (2H, s, Ar-H), 11.21 (1H, s, NH).

EXAMPLE 58

4-([N-Methyl-2-methylcarbamoyl-1--phenyl]ethyl)-1-[3-(5-(1,2,4-triazol-4-yl)-1H-indol-3-yl)propyl] piperazine. 1.3 Hydrogen Oxalate a) 4-([2-N-Methylamino-1-phenyl]ethyl)-1-[3-(5-(1,2,4-triazol-4-yl)-1H-indol-3-yl)propyl]piperazine The title compound was prepared in the same manner as that described in Example 51 Step a), replacing ammonia with methylamine. δ (250 MHz, CDCl$_3$) 1.86–1.98 (2H, m), 2.89 (3H, s), 2.33–2.82 (14H, m), 3.60 (1H, dd, J=10.9 and 3.4Hz), 7.12–7.16 (2H, m), 7.24–7.34 (5H, m), 7.48 (1H, d, J=8.5Hz), 7.56 (1H, d, J=2.0Hz), 8.47 (2H, s), 8.70 (1H, br s).

b) 4-([N-Methyl-2-methylcarbamoyl-1-phenyl]ethyl)-1-[3-(5-(1,2,4-triazol-4-yl)-1H-indol-3-yl)propyl]piperazine. 1.3 Hydrogen Oxalate The title compound was prepared in the same manner as that described in Example 51, Step b, using the piperazine prepared above. mp 160° C., (Found: C, 57.82, H, 6.38, N, 15.34%. C$_{28}$H$_{35}$N$_7$O$_2$. 1.3(C$_2$H$_2$O$_4$). H$_2$O requires C, 57.73, H, 6.27, N, 15.40%), m/e 502 (M+1)$^+$, δ (360 MHz, d$_6$-DMSO) 1.99–2.10 (2H, m), 2.61 (3H, s), 2.72–3.10 (14H, m), 3.63 (3H, s), 5.37–5.50 (1H, m), 7.26–7.42 (7H, m), 7.51 (1H, d, J=8.6Hz), 7.81 (1H, s), 9.02 (2H, s), 11.18 (1H, br s).

We claim:

1. A compound as represented by formula IIA, or a pharmaceutically acceptable salt thereof:

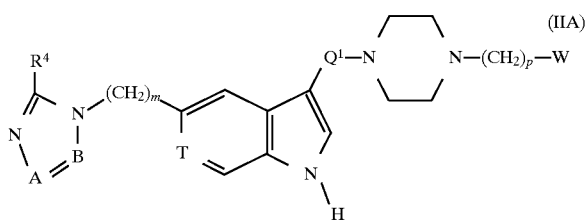

(IIA)

wherein m is zero, 1, 2 or 3;

p is 1, 2 or 3;

$Q^1$ represents a straight or branched alkylene chain containing from 2 to 5 carbon atoms, optionally substituted in any position by a hydroxy group;

T represents nitrogen or CH;

A represents nitrogen or CH;

B represents nitrogen or C—$R^5$;

$R^4$ and $R^5$ represent hydrogen; and

W represents a group of formula (a), (b) or (c):

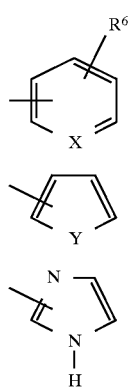

in which

X represents CH or nitrogen;

Y represents oxygen, sulphur or NH; and $R^6$ represents hydrogen, halogen, cyano, trifluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, aminosulphonyl or C$_{1-6}$ alkylaminosulphonylmethyl.

2. A compound represented by formula IIC or a pharmaceutically acceptable salt thereof:

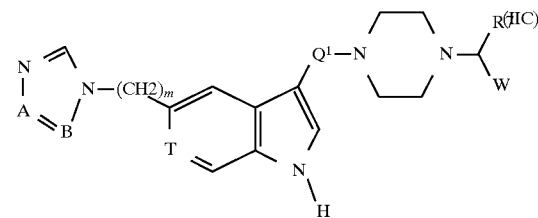

(IIC)

wherein m is zero, 1,2 or 3;

A represents nitrogen or CH;

B represents nitrogen or C—$R^5$;

$Q^1$ represents a straight or branched alkylene chain containing from 2 to 5 carbon atoms, optionally substituted in any position by a hydroxy group;

T represents nitrogen or CH;

$R^5$ represents hydrogen;

W represents a group of formula (a),(b) or (c):

(a)

(b)

(c)

in which

X represents CH or nitrogen;

Y represents oxygen, sulphur or NH; and $R^6$ represents hydrogen, halogen, cyano, trifluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, aminosulphonyl or C$_{1-6}$ alkylaminosulphonylmethyl; and $R^7$ represents hydrogen, aminomethyl, C$_{1-6}$alkylaminomethyl, di(C$_{1-6}$)alkylaminomethyl, C$_{2-6}$alkoxycarbonylaminomethyl, aminomethyl, aminocarbonyl, C$_{1-6}$alkylaminocarbonyl or di(C$_{1-6}$) alkylaminocarbonyl.

3. A compound selected from:

1-[3-(5-(1,2,4-triazol-4-yl)-1H-indol-3-yl)propyl]-4-[4-(acetylamino)phenyl]methylpiperazine;

1-[4-(5-(1,2,4-triazol-4-yl)-1H-indol-3-yl)butyl]-4-[4-(acetylamino)phenyl]methylpiperazine;

1-[3-(5-(1,2,4-triazol-4-yl)-1H-indol-3-yl)propyl]-4-(2-methoxyphenyl)methylpiperazine;

1-[3-(5-(1,2,4-triazol-4-yl)-1H-indol-3-yl)propyl]-4-benzylpiperazine;

1-[3-(5-(1,2,4-triazol-4-yl)-1H-indol-3-yl)propyl]-4-(pyridin-3-yl)methylpiperazine;

1-[3-(5-(1,2,4-triazol-4-yl)-1H-indol-3-yl)propyl]-4-(pyridin-2-yl)methylpiperazine;

1-[3-(5-(1,2,4-triazol-4-yl)-1H-indol-3-yl)propyl]-4-(pyridin-4-yl)methylpiperazine;
1-[3-(5-(1,2,4-triazol-4-yl)-1H -indol-3-yl)propyl]-4-(4-aminophenyl)methylpiperazine;
1-[4-(5-(1,2,4-triazol-4-yl)-1H -indol-3-yl)butyl]-4-benzylpiperazine;
1-[4-(5-(1,2,4-triazol-4-yl)-1H -indol-3-yl)butyl]-4-(pyridin-2-yl)methylpiperazine;
1-[4-(5-(1,2,4-triazol-4-yl)-1-indol-3-yl)butyl]-4-(pyridin-3-yl)methylpiperazine;
1-[3-(5-(1,2,4-triazol-4-yl)-1H-indol-3-yl)propyl]-4-[2-(4-aminophenyl)ethyl]piperazine;
1-[3-(5-(1,2,4-triazol-4-yl)-1H-indol-3-yl)propyl]-4-[2-(4-(acetylamino)phenyl)ethyl]piperazine;
1-[3-(5-(1,2,4-triazol-4-yl)-1H-indol-3-yl)propyl]-4-(imidazol-2-yl)methylpiperazine;
1-[3-(5-(1,2,4-triazol-4-yl)-1H-indol-3-yl)propyl]-4-[3-(acetylamino)phenyl]methylpiperazine;
and pharmaceutically acceptable salts thereof.

4. A compound selected from:
4-benzyl-1-[3-(5-(1,2,4-triazol-1-yl)-1H-pyrrolo[2,3-c]pyridin-3-yl)propyl]piperazine;
4-benzyl-1-[3-(5-(1,2,4-triazol-4-yl)-1H-pyrrolo[2,3-c]pyridin-3-yl)propyl]piperazine;
and pharmaceutically acceptable salts thereof.

5. A compound selected from:
1-[3-(5-(1,2,4-triazol-4-yl)-1H-indol-3-yl)propyl]-4-(2-aminopyridin-5-yl)methylpiperazine;
1-[3-(5-(1,2,4-triazol-4-yl)-1H-indol-3-yl)propyl]-4-[2-(4-(aminocarbonylamino)phenyl)ethyl]piperazine;
1-[3-(5-(1,2,4-triazol-4-yl)-1H-indol-3-yl)propyl]-4-(4-cyanophenyl)methylpiperazine;
1-[3-(5-(1,2,4-triazol-4-yl)-1H-indol-3-yl)propyl]-4-[2-(4-cyanophenyl)ethyl]piperazine;
1-[3-(5-(1,2,4-triazol-4-yl)-1H-indol-3-yl)propyl]-4-[2-(4-(1,2,4-triazol-4-yl)phenyl)ethyl]piperazine;
1-[3-(5-(1,2,4-triazol-1-yl)-1H-indol-3-yl)propyl]-4-[2-(4-(acetylamino)phenyl)ethyl]piperazine;
1-[3-(5-(1,2,4-triazol-1-yl)-1H-indol-3-yl)propyl]-4-benzylpiperazine;
1-[3-(5-(1,2,4-triazol-1-ylmethyl)-1H-indol-3-yl)propyl]-4-benzylpiperazine;
and pharmaceutically acceptable salts thereof.

6. A compound selected from:
1-[3-(5-(1,2,4-triazol-1-ylmethyl)-1H-indol-3-yl)propyl]-4-[2-(4-(acetylamino)phenyl)ethyl]piperazine;
1-[3-(5-(1,2,4-triazol-4-yl)-1H-indol-3-yl)propyl]-4-[2-(3-(acetylamino)phenyl)ethyl]piperazine;
1-[3-(5-(1,2,4-triazol-4-yl)-1H-indol-3-yl)propyl]-4-[4-(aminosulphonyl)phenyl]methylpiperazine;
1-[3-(5-(1,2,4-triazol-4-yl)-1H-indol-3-yl)propyl]-4-(furan-3-yl)methylpiperazine;
1-[3-(5-(1,2,4-triazol-4-yl)-1H-indol-3-yl)propyl]-4-(furan-2-yl)methylpiperazine;
1-[3-(5-(1,2,4-triazol-4-yl)-1H-indol-3-yl)propyl]-4-(thien-2-yl)methylpiperazine;
1-benzyl-4-[(R,S)-2-hydroxy-3-(5-(1,2,4-triazol-4-yl)-1H-indol-3-yl)propyl]piperazine;
1-[2-(4-(acetylamino)phenyl)ethyl]-4-[(R,S)-2-hydroxy-3-(5-(1,2,4-triazol-4-yl)-1H-indol-3-yl)propyl]piperazine;
1-benzyl-4-[(R,S)-2-hydroxymethyl-3-(5-(1,2,4-triazol-4-yl)-1H-indol-3-yl)propyl]piperazine;
1-[3-(5-(1,2,4-triazol-4-yl)-1H-indol-3-yl)propyl]-4-[2-(1H-tetrazol-5-yl)phenyl]methylpiperazine;
and pharmaceutically acceptable salts thereof.

7. A compound selected from:
1-[3-(5-(1,2,4-triazol-4-yl)-1H-indol-3-yl)propyl]-4-(2-phenylethyl)piperazine;
4-[2-(2-methyltetrazol-5-yl)phenyl]methyl-1-[3-(5-(1,2,4-triazol-4-yl)-1H-indol-3-yl)propyl]piperazine;
4-[2-(1-methyltetrazol-5-yl)phenyl]methyl-1-[3-(5-(1,2,4-triazol-4-yl)-1H-indol-3-yl)propyl]piperazine;
4-[2-(N-methylcarboxamido)phenyl]methyl-1-[3-(5-(1,2,4-triazol-4-yl)-1H-indol-3-yl)propyl]piperazine;
4-[2-(N,N-dimethylaminomethyl)phenyl]methyl-1-[3-(5-(1,2,4-triazol-4-yl)-1H-indol-3-yl)propyl]piperazine;
4-(but-3-enyl)-1-[3-(5-(1,2,4-triazol-4-yl)-1H-indol-3-yl)propyl]piperazine;
4-(3-methylbut-2-enyl)-1-[3-(5-(1,2,4-triazol-4-yl)-1H-indol-3-yl)propyl]piperazine;
4-(prop-2-enyl)-1-[3-(5-(1,2,4-triazol-4-yl)-1H-indol-3-yl)propyl]piperazine;
4-(prop-2-ynyl)-1-[3-(5-(1,2,4-triazol-4-yl)-1H-indol-3-yl)propyl]piperazine;
4-[(R,S)-1-(phenyl)carboxamidomethyl]-1-[3-(5-(1,2,4-triazol-4-yl)-1H-indol-3-yl)propyl]piperazine;
(+)-4-[1-(phenyl)carboxamidomethyl]-1-[3-(5-(1,2,4-triazol-4-yl)-1H-indol-3-yl)propyl]piperazine;
(-)-4-[1-(phenyl)carboxamidomethyl]-1-[3-(5-(1,2,4-triazol-4-yl)-1H-indol-3-yl)propyl]piperazine;
4-[1-(phenyl)-N-methylcarboxamidomethyl]-1-[3-(5-(1,2,4-triazol-4-yl)-1H-indol-3-yl)propyl]piperazine;
4-[1-(phenyl)-N,N-dimethylcarboxamidomethyl]-1-[3-(5-(1,2,4-triazol-4-yl)-1H-indol-3-yl)propyl]piperazine;
4-(2-methoxycarbonylamino-1-phenylethyl)-1-[3-(5-(1,2,4-triazol-4-yl)-1H-indol-3-yl)propyl]piperazine;
4-(2-dimethylamino-1-phenylethyl)-1-[3-(5-(1,2,4-triazol-4-yl)-1H-indol-3-yl)propyl]piperazine;
4-[2-(4-(acetylamino)phenyl)ethyl]-1-[3-(5-(1,2,4-triazol-1-yl)-1H-pyrrolo[2,3-c]pyridin-3-yl)propyl]piperazine;
4-[2-(4-(acetylamino)phenyl)ethyl]-1-[3-(5-(1,2,4-triazol-4-yl)-1H-pyrrolo [2,3-c]pyridin-3-yl)propyl]piperazine;
1-[3-(5-(1,2,4-triazol-4-yl)-1H-indol-3-yl)propyl]-4-(4-fluorophenyl)methylpiperazine;
4-[2-(N-methyl-N-methoxycarbonyl)amino-1-phenylethyl]-1-[3-(5-(1,2,4-triazol-4-yl)-1H-indol-3-yl)propyl]piperazine;
and pharmaceutically acceptable salts thereof.

8. A pharmaceutical composition comprising a compound as claimed in claim 1 in association with a pharmaceutically acceptable carrier.

9. A method for the treatment and/or prevention of migraine, cluster headache, chronic paroxysmal hemicrania, headache associated with vascular disorders, tension headache and pediatric migraine, for which a subtype-selective agonist of human 5-HT$_{1D}$ receptors is indicated, which method comprises administering to a patient in need of such treatment an effective amount of a compound as claimed in claim 1.

* * * * *